(12) United States Patent
Melgarejo et al.

(10) Patent No.: US 7,985,832 B2
(45) Date of Patent: Jul. 26, 2011

(54) ANTIMICROBIAL CATHELICIDIN PEPTIDES

(75) Inventors: Tonatiuh Melgarejo, Manhattan, KS (US); Frank Blecha, Manhattan, KS (US); Yongming Sang, Manhattan, KS (US); Maria Teresa Ortega, Manhattan, KS (US)

(73) Assignee: Kansas State University Research Foundation, Manhattan, KS (US)

( * ) Notice: Subject to any disclaimer, the term of this patent is extended or adjusted under 35 U.S.C. 154(b) by 0 days.

(21) Appl. No.: 12/087,228

(22) PCT Filed: Dec. 29, 2006

(86) PCT No.: PCT/US2006/049637
§ 371 (c)(1),
(2), (4) Date: Nov. 20, 2008

(87) PCT Pub. No.: WO2007/076162
PCT Pub. Date: Jul. 5, 2007

(65) Prior Publication Data
US 2009/0221483 A1 Sep. 3, 2009

Related U.S. Application Data

(60) Provisional application No. 60/754,878, filed on Dec. 29, 2005.

(51) Int. Cl.
*A61K 38/00* (2006.01)
*A61K 38/17* (2006.01)
*A61P 31/00* (2006.01)
*A01N 37/18* (2006.01)
*C07K 14/00* (2006.01)
*C07K 16/00* (2006.01)
*C07K 17/00* (2006.01)
*C07K 2/00* (2006.01)
*C07K 4/00* (2006.01)
*C07K 7/00* (2006.01)
*C07K 5/00* (2006.01)

(52) U.S. Cl. .......... 530/300; 530/324; 514/2.2; 514/2.3

(58) Field of Classification Search .................. None
See application file for complete search history.

(56) References Cited

U.S. PATENT DOCUMENTS

| | | | | |
|---|---|---|---|---|
| 5,830,993 | A * | 11/1998 | Blecha et al. | 530/300 |
| 7,173,007 | B1 * | 2/2007 | Zaiou et al. | 514/12 |
| 7,485,619 | B2 * | 2/2009 | Kim et al. | 514/2 |
| 2003/0022829 | A1 * | 1/2003 | Maury et al. | 514/12 |
| 2007/0037744 | A1 * | 2/2007 | Gallo et al. | 514/12 |
| 2007/0065908 | A1 * | 3/2007 | Gallo et al. | 435/69.1 |
| 2007/0076162 | A1 | 4/2007 | Kim | |
| 2009/0048167 | A1 * | 2/2009 | Hillman | 514/12 |
| 2009/0221483 | A1 * | 9/2009 | Melgarejo et al. | 514/12 |

FOREIGN PATENT DOCUMENTS

| | | | |
|---|---|---|---|
| CA | 2632782 A1 * | 7/2007 | |
| EP | 1966235 A2 * | 9/2008 | |
| WO | WO-2005/040192 A2 | 5/2005 | |
| WO | WO-2005/040201 A1 | 5/2005 | |
| WO | WO-2007/076162 A2 | 7/2007 | |
| WO | WO-2007/076162 A3 | 7/2007 | |
| WO | WO 2009/010968 A2 * | 1/2009 | |

OTHER PUBLICATIONS

Yang et al, Trends Immunol., 2002, 23:291-296.*
Tomasinsig et al, Current Protein and Peptide Science, 2005, 6:23-34.*
Dawson et al, Drug Development Research, 2009, 70:481-498.*
Doss et al, J. Leukoc. Biol., 2010, 87:79-92.*
Ramanathan et al, Microbes and Infection, 2002, 4:361-372.*
Sang et al, Developmental and Comparative Immunology, 2007, 31:1278-1296.*
Gombart et al, Blood, vol. 108, No. 11, Part 1, pp. 467A-468A abstract only.*
Sang et al, Developmental and Comparative Immunology, 2009, 33:334-343.*
Burgess et al, JCB, 1990, 111:2129-2138.*
Lazar et al, Molecular and Cellular Biology, 1988, 8:1247-1252.*
Creighton, In: Proteins: Structures and Molecular Properties, 1984, pp. 314-315.*
Greenspan et al, Nature Biotechnology, 1999, 17:936-937.*
Houghten et al, Vaccine 86, 1986. pp. 21-25.*
Bixler et al, Synthetic Vaccines, vol. 1, 1987, pp. 39-71.*
Bowie et al, Science, 1990, 247:1306-1310.*
Kumar et al, PNAS, USA, Feb. 1991, 87:1337-1341.*
"International Application Serial No. PCT/US2006/049637, International Search Report mailed Jun. 28, 2008", 9 pgs.
"International Application Serial No. PCT/US2006/049637, Written Opinion mailed Jun. 28, 2008", 5 pgs.
Sang, et al., "Canine Cathelicidin: cloning of a novel antimicrobal peptide", *Gene Bank*, (May 1, 2004), 1 pg.
"European application No. 06848843.6 Search report mailed Dec. 14, 2009", 4 pgs.
Sang, Y., et al., "Canine Cathelicidin: cloning of a novel antimicrobial peptide", *AY392089—Database Genebank*, (May 1, 2004).
Tomasinsig, L., et al., "The cathelicidins—structure, function and evolution", *Curr Protein Pept Sci.*, 6(1), (Feb. 2005), 23-24.
"European Application Serial No. 06848843.6, Office Action mailed Mar. 23, 2010", 1 Pg.

(Continued)

*Primary Examiner* — Nita M Minnifield
(74) *Attorney, Agent, or Firm* — Schwegman, Lundberg & Woessner, P.A.

(57) ABSTRACT

The invention relates to antimicrobial cathelicidin polypeptides related to a 38 amino acid peptide having SEQ ID NO:4. The invention provides for polypeptides having broad spectrum antimicrobial activity, nucleic acids and expression vectors encoding such polypeptides, as well as host cells and methods of reducing survival of a microbe. In addition, the invention also provides compositions, as well as articles of manufacture, that comprise a broad spectrum antimicrobial polypeptide.

14 Claims, 11 Drawing Sheets

OTHER PUBLICATIONS

"New Zealand Application Serial No. 569314, First Examiners Report mailed Apr. 23, 2010", 2 Pgs.

"Chinese Application Serial No. 200680049565.2, First Office Action mailed Jan. 4, 2011", (w/ English Translation), 9 pgs.

"Japanese Application Serial No. 2008-548779, Response and Amended Claims filed Dec. 21, 2009", (w/ English Translation of Amended Claims), 9 pgs.

* cited by examiner

A

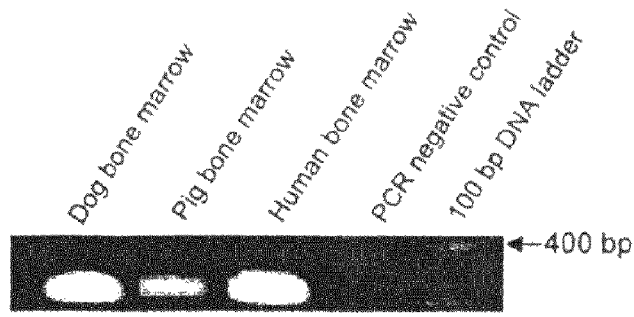

←400 bp

B

```
  1 ggagagacttgcaggctgagaggagggagacttggggaccATG GAG ACC
  1                                          M   E   T 50 CAG AAG GAC AGC CCC TCC CTG GGG CGG TGG TCA CTG TTG
  4  Q   K   D   S   P   S   L   G   R   W   S   L   L 89 CTA CTG CTG CTG GGC CTG GTG ATC ACT CCG GCT GCC TCC
 17  L   L   L   L   G   L   V   I   T   P   A   A   S 128 CGG GCC CTT AGC TAC AGG GAG GCT GTG CTC CGT GCT GTG
 30  R   A   L   S   Y   R   E   A   V   L   R   A   V 167 AAT GGC TTC AAC CAG CGG TCC TCG GAG GAG AAT CTC TAC
 43  N   G   F   N   Q   R   S   S   E   E   N   L   Y 206 CGT CTC CTG CAG CTG AAC TCA CAG CCC AAG GGA GAT GAG
 56  R   L   L   Q   L   N   S   Q   P   K   G   D   E 245 GAT CCA AAC ATC CCA AAG CCT GTG AGC TTC ACA GTG AAG
 69  D   P   N   I   P   K   P   V   S   F   T   V   K 284 GAG ACT GTG TGT CCC AAG ACG ACA CAG CAG CCT CTG GAG
 82  E   T   V   C   P   K   T   T   Q   Q   P   L   E 323 CAG TGT GGT TTC AAG GAC AAT GGG CTG GTG AAA CAG TGT
 95  Q   C   G   F   K   D   N   G   L   V   K   Q   C 362 GAA GGG ACA GTC ATC CTG GAC GAG GAC ACG GGC TAC TTT
108  E   G   T   V   I   L   D   E   D   T   G   Y   F 401 GAC CTC AAC TGT GAT TCA ATC CTG CAA GTC AAG AAA ATT
121  D   L   N   C   D   S   I   L   Q   V   K   K   I 440 GAC CGG CTG AAA GAG CTC ATC ACG ACA GGG GGG CAG AAG
134  D   R   L   K   E   L   I   T   T   G   G   Q   K 479 ATT GGC GAA AAG ATT AGG AGA ATT GGC CAG AGA ATC AAG
147  I   G   E   K   I   R   R   I   G   Q   R   I   K 518 GAT TTT TTT AAG AAT CTT CAG CCC AGG GAG GAG AAG TCC
160  D   F   F   K   N   L   Q   P   R   E   E   K   S 557 TAAgggcctgctttgccctggcttaggcttctggaccctgaaaaataaatt 608 tttgtgaaagcaaaaaaaaaaaa
```

ANTIMICROBIAL CATHELICIDIN PEPTIDES

CROSS REFERENCE TO RELATED APPLICATION

This application is a nationalization under 35 U.S.C. 371 of PCT/US2006/049637, filed Dec. 29, 2006 and published as WO2007/076162 A1, on Jul. 5, 2007, which claimed priority under 35 U.S.C. 119(e) to U.S. Provisional Application Ser. No. 60/754,878, filed Dec. 29, 2005, which applications and publication are incorporated herein by reference and made a part hereof.

STATEMENT REGARDING FEDERALLY SPONSORED RESEARCH

Work relating to this application was supported by a grant from the U.S. Government (N.I.H. grant number P20 RR016475 and P20 RR017686). Thus, the Government may have certain rights in the invention.

BACKGROUND

Antimicrobials are vital medicines for the treatment of infections in humans. Antimicrobials are also widely used in livestock, fish and plant production. In animals, antimicrobials are used for treatment of infection and prophylactically for disease prevention. In addition, subtherapeutic doses of antimicrobials are used as growth promoters. The result of such widespread use of antimicrobials is an increase in the prevalence of resistant pathogens giving rise to therapeutic failures in humans and animals. Thus, a need exists to develop new and effective antimicrobial agents.

SUMMARY OF THE INVENTION

The invention provides a purified cathelicidin polypeptide, a fragment thereof, a variant thereof or a fragment of the variant, having broad antimicrobial activity against Gram-positive and Gram-negative bacteria, as well as yeast and protozoa (a "microbe" or "microorganism" hereinafter). Thus, the purified polypeptide, variant thereof, or fragment thereof, or an isolated nucleic acid molecule encoding any thereof, can be used to inhibit or prevent growth of a microorganism. In one embodiment, the purified polypeptide, variant thereof, or fragment thereof, or an isolated nucleic acid molecule encoding any thereof, can be used to treat or prevent a disease such as a food-borne illness or a sexually-transmitted disease, e.g., by members of the genera *Trichomonas* and/or *Neisseria*. As described hereinbelow, the antimicrobial activity of a polypeptide, variant or fragment of the invention may be salt-independent. Moreover, in one embodiment, the polypeptide, variant or fragment of the invention also has minimal hemolytic activity. In one embodiment, the invention provides a purified polypeptide comprising SEQ ID NO: 4, a variant of SEQ ID NO: 4 having at least 15%, e.g., at least 20%, 30%, 40%, 50%, 70% or more, e.g., 80%, or 90%, amino acid sequence identity to SEQ ID NO: 4, or a fragment thereof having at least 15 contiguous amino acids, wherein the polypeptide, the variant thereof or the fragment thereof has antimicrobial activity.

Accordingly, the invention also provides an isolated nucleic acid molecule, as well as an expression vector, encoding an antimicrobial polypeptide, variant or fragment thereof of the invention; an isolated cell containing such a nucleic acid molecule and/or expression vector; a composition containing a nucleic acid molecule or a polypeptide, variant or fragment of the invention; and an article of manufacture containing a nucleic acid molecule, or a polypeptide, variant or fragment of the invention. The invention also provides a method of producing the antimicrobial polypeptide, variant or fragment thereof, as well as a method of reducing or inhibiting growth of a microorganism using an isolated nucleic acid molecule encoding an antimicrobial polypeptide, variant or fragment thereof, or an antimicrobial polypeptide, variant or fragment thereof, of the invention.

In one embodiment, the invention provides an isolated nucleic acid molecule which includes a nucleotide sequence having at least 70%, e.g., 80%, 90%, 95% or 100%, nucleic acid sequence identity to SEQ ID NO: 1, SEQ ID NO: 3, or a degenerate variant thereof.

In another embodiment, the invention provides an isolated nucleic acid molecule having a nucleotide sequence that hybridizes under highly stringent conditions or moderately stringent conditions to a hybridization probe having a nucleotide sequence which is the complement of the coding region of SEQ ID NO: 3 or a fragment thereof that is at least 15 nucleotides, e.g. at least 100 nucleotides, in length.

In another embodiment, the invention provides an isolated nucleic acid molecule having a nucleotide sequence that encodes a polypeptide having SEQ ID NO: 2 or SEQ ID NO: 4, or a fragment of SEQ ID NO: 2 or SEQ ID NO: 4 that is at least 15 amino acids in length and has antimicrobial activity. In some embodiments, the fragment of SEQ ID NO: 2 is at least 20, 25, 30, 35, 40, 45, 50 or more than 50 amino acids in length. In one embodiment, the fragment of SEQ ID NO: 4 is at least 20, 25, 30, more than 30 amino acids in length. In some embodiments, the fragment has antimicrobial activity, and/or it is immunogenic, immunoregulatory, or both immunogenic and immunoregulatory.

In another embodiment, the invention provides an expression vector containing a nucleic acid molecule which encodes the polypeptide, variant or fragment thereof of the invention. In another embodiment, the invention provides an isolated cell containing the nucleic acid molecule of the invention, e.g., one operably linked to an expression control sequence. In some embodiments, the isolated cell expresses the polypeptide, variant or fragment thereof of the invention. In one embodiment, the polypeptide, variant or fragment thereof is purified from the cell or the medium of the cell.

In another embodiment, the invention provides a purified polypeptide that is biologically active and has an amino acid sequence of at least 15, e.g., 20, consecutive residues of SEQ ID NO: 2, is at least 15% identical to SEQ ID NO: 4; or binds an antibody that binds specifically to SEQ ID NO: 4. In some embodiments, the polypeptide has SEQ ID NO: 2 or 4. In some embodiments, the polypeptide consists of SEQ ID NO: 2 or 4. In some embodiments, the polypeptide has 1, 2, 3, 4, 5, or 10, or more, e.g., 20, conservative amino acid substitutions relative to SEQ ID NO: 4.

In another embodiment, the invention provides a composition comprising the polypeptide, variant or fragment of the invention. In some embodiments, the composition further includes a pharmaceutically acceptable carrier or a food additive.

In another embodiment, the invention provides a method of reducing or inhibiting growth or survival of a microbe. The method includes contacting the microbe with the polypeptide, variant, or fragment, or a composition having the polypeptide, variant, or fragment or a nucleic acid molecule encoding the polypeptide, variant, or fragment, of the invention.

In another embodiment, the invention provides a method of reducing or inhibiting growth or survival of a microbe in a vertebrate such as a mammal, fish or bird, or in a medium, e.g., aqueous medium or packaging capable of supporting growth or survival of the microbe. The method includes contacting the vertebrate or medium with an effective amount of the polypeptide, variant, or fragment, or a nucleic acid molecule encoding the polypeptide, variant, or fragment, of the invention.

In another embodiment, the invention provides a method of treating a food-borne illness or a sexually transmitted disease such as syphilis, chlamydia, gonorrhoeae, trichomoniasis, or thrush. The method includes administering an effective amount of the polypeptide, variant, or fragment, or a nucleic acid molecule encoding the polypeptide, variant, or fragment of the invention to a vertebrate.

In one embodiment, the invention provides a method of reducing microbial contamination of food items or increasing the shelf life of a perishable food using an effective amount of the polypeptide, variant, or fragment, of the invention.

In another embodiment, the invention provides an article of manufacture that includes a vessel and the polypeptide, variant, or fragment, or a nucleic acid molecule encoding the polypeptide, variant, or fragment, of the invention. In one embodiment, the article of manufacture comprises packaging material and, contained within the packaging material, the polypeptide, variant or fragment, or nucleic acid molecule encoding the polypeptide, variant or fragment, of the invention, wherein the packaging material comprises a label that indicates that the polypeptide, variant, or fragment, or a nucleic acid molecule encoding the polypeptide, variant, or fragment, of the invention can be used for treating a food-borne illness or a sexually transmitted disease such as syphilis, chlamydia, gonorrhoeae, trichomoniasis, or thrush.

In another embodiment, the invention provides a purified antibody that binds specifically to SEQ ID NO: 4.

BRIEF DESCRIPTION OF DRAWINGS

FIG. 1. Identification of Canine Cathelicidin. (A) cDNA amplified from dog, human, and pig bone marrow using RT-PCR with degenerate primers. Human and porcine samples were used as positive controls. (B) Full cDNA (SEQ ID NO: 1) and predicted peptide sequence (SEQ ID NO: 2) of canine cathelicidin. Start and stop codons in the cDNA sequence are bolded. The coding region is in triple codon format, and the untranslated regions are in lower cases. Predicted signal peptide (N-terminal 29 amino acids) is italicized and indicated by an arrow.

FIG. 3. Similarity Comparison of Cathelicidins from Different Species. The cathelicidin domain is underlined; the conserved cysteine residues in cathelicidin domain are framed. The arrow indicates the predicated site for generation of C-terminal synthetic peptides. The percentages of similarity and identity to canine cathelicidin (K9CATH, SEQ ID NO: 2) are listed behind the sequence. GenBank accession numbers of related sequences are: human (Hs) LL-37, P49913 (SEQ ID NO: 33); equine (Ec) CATHL2, CAA12227 (SEQ ID NO: 34); bovine (Bt) CATHL1, NP777250 (SEQ ID NO: 35); bovine CATHL7, NP777256 (SEQ ID NO: 36); porcine (Ss) PMAP37, P49932 (SEQ ID NO: 37); and porcine PR-39, P80054 (SEQ ID NO: 38).

DETAILED DESCRIPTION OF THE INVENTION

Definitions

Figure 2:
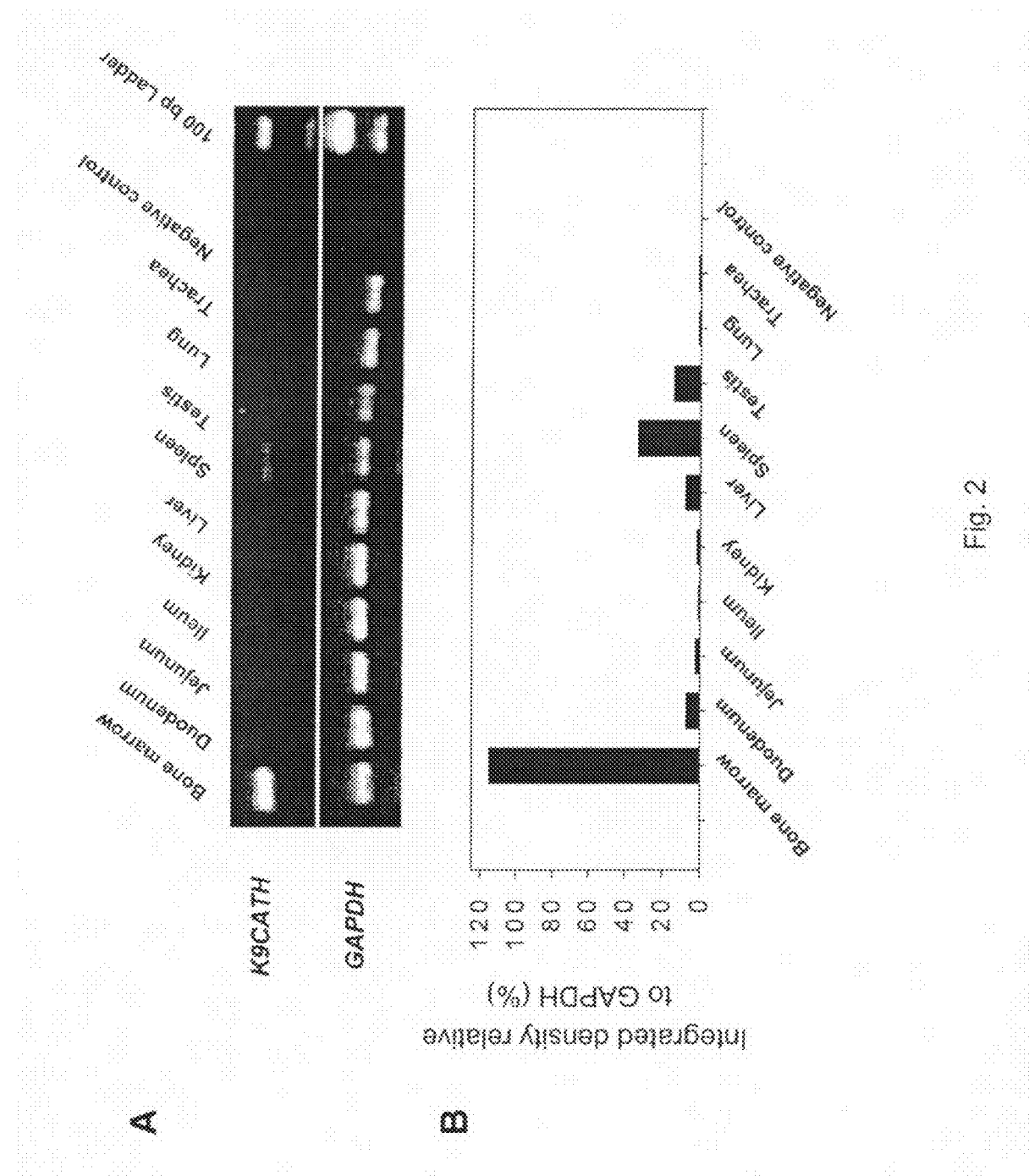
FIG. 2. Tissue Expression profile of Canine Cathelicidin. One step RT-PCR was performed using 400 ng of total RNA in 25 mL reactions for 40 cycles using gene specific primers. Complementary DNA fragments of glyceraldehyde-3-phosphate dehydrogenase (GAPDH) were amplified with the same RNA samples. Result is representative of two independent experiments with similar patterns using tissues from two dogs.

The term "nucleic acid," as used herein, refers to a polymer of deoxynucleic ribose nucleic acids, as well as ribose nucleic acids. The term includes linear molecules, as well as covalently closed circular molecules. It includes single stranded molecules, as well as double stranded molecules.

The term "isolated," as used herein with reference to a nucleic acid molecule, means that the nucleic acid molecule is free of unrelated nucleic acid sequences, i.e. nucleic acid sequences encoding other genes, or involved in the expression of such other genes, that flank it's 5' and 3' ends in the naturally-occurring genome of the organism from which the nucleic acid of the invention is derived. Accordingly, an "isolated nucleic acid" of the invention has a structure that is different from that of any naturally occurring nucleic acid or to that of any fragment of a naturally occurring genomic nucleic acid spanning more than three separate genes. Thus, the term "isolated nucleic acid molecule" includes, for example, (1) a DNA molecule that has the sequence of part of a naturally occurring genomic DNA molecule, but is not flanked by both of the coding sequences that flank that part of the molecule in the genome of the organism in which it naturally occurs; (2) a nucleic acid incorporated into a vector or into the genomic DNA of a prokaryote or eukaryote in a manner such that the resulting molecule is not identical to any naturally-occurring vector or genomic DNA; (3) a separate molecule such as a cDNA, a genomic fragment, a fragment produced by polymerase chain reaction (PCR), or a restriction fragment; and (4) a recombinant nucleotide sequence that is part of a hybrid gene, i.e. a gene encoding a fusion protein. Specifically excluded from this definition are nucleic acids present in mixtures of (1) DNA molecules, (2) transfected cells, and (3) cell clones, e.g., as these occur in a DNA library such as a cDNA or genomic DNA library.

The term "purified" with reference to a polypeptide, variant or fragment means that the polypeptide, variant or fragment is substantially free of naturally-associated components, that is components that accompany it in its natural state. A chemically synthesized polypeptide, one produced using recombinant DNA technology, or one produced in a cellular system different from the cell system from which the polypeptide of the invention naturally originates, is substantially free from its naturally associated components. The term "purified polypeptide" does not encompass the polypeptides separated in a lane of a protein gel in which multiple unrelated polypeptides have been separated. In general, a polypeptide, variant or fragment of the invention can constitute at least about 25% by weight of a sample containing the polypeptide of the invention, and usually constitutes at least about 50%, at least about 75%, at least about 85%, at least about 90% of a sample, particularly at least about 95% of the sample or 99% or more.

The phrase "biologically active fragment" as used herein in reference to a polypeptide or variant of the invention, means a fragment having at least 15 to 20 contiguous amino acids of the sequence shown in SEQ ID NO: 4, that also (1) has antimicrobial activity and/or (2) is immunogenic, immunoregulatory, or both immunogenic and immunoregulatory.

The term "polypeptide," as used herein, means a polymer composed of at least 15 amino acids, regardless of post-translational modifications such as methylation, glycosylation or phosphorylation. The phrase "antimicrobial polypeptide of the invention," or "a polypeptide of the invention," as well as the term "K9CATH," refer to a canine cathelicidin polypeptide, as well as a derivative thereof.

As used herein, the phrase "antimicrobial activity" means microbicidal and/or microbiostatic activity against one or more bacteria, fungi, viruses or protozoans. Microbicidal activity refers to the ability kill or cause irreversible damage to a target microorganism. Microbiostatic activity refers to the ability to inhibit the growth or proliferative ability of a target microorganism without necessarily killing or irreversibly damaging it.

The term "immunogenic" means that the polypeptide, variant or fragment is capable of eliciting the production of antibodies specific for a polypeptide having the amino acid sequence of SEQ ID NO: 4. The phrase "binds specifically," or the term "specific," in reference to an antibody, means that the antibody binds with at least 50% or greater affinity, preferably about 75% or greater affinity, and more preferably, about 90% or greater affinity, to a polypeptide of SEQ ID NO: 4 than to a polypeptide that has less than 80% identity to SEQ ID NO: 4.

The term "immunoregulatory" means that the polypeptide, variant or fragment does not affect or regulate the normal function, e.g. the cellularity, of the immune system in an unstimulated animal, but does affect or regulate the immune system that has been altered by a disease. Non-limiting examples of such regulation include inhibition of the delayed-type hypersensitivity (DTH) reaction, inhibition of immune cell responsiveness, and inhibition of antibody production in response to antigenic challenge.

As used herein, the term "inhibit" means a decrease in any amount including, without limitation, a 5%, 10%, 15%, 20%, 25%, 30%, 35%, 40%, 45%, 50%, 55%, 60%, 65%, 70%, 75%, 80%, 85%, 90%, 95% or more than 95% decrease, e.g. a 100% decrease.

The term "therapeutically effective amount" means an amount of a compound or combination of compounds that treats a disease; ameliorates, attenuates, or eliminates one or more symptoms of a particular disease; or prevents or delays the onset of one or more symptoms of a disease.

The phrase "a medium capable of supporting growth" of a microbe, includes a gaseous, liquid or solid material, in or upon which a bacterium, virus, fungus or protozoa can survive or propagate. Such a medium includes a tissue or bodily fluid of a vertebrate such as a human, fish, chicken or another bird; a liquid such as water or an aqueous solution such as contact lens solution or eyewash solution; a food such as a food crop and a food product such as an extract, frozen or dehydrated food or other processed food product; prepackaged food such as cheese, poultry or other meat; and an object such as the surface of an instrument used, for example, to prepare food or to perform surgery; and a gas such as that used for anesthetization in preparation for surgery.

Unless otherwise defined, all technical and scientific terms used herein have the same meaning as commonly understood by one of ordinary skill in the art to which this invention belongs. Although methods and materials similar or equivalent to those described herein can be used to practice the invention, suitable methods and materials are described below. All publications, patent applications, patents and other references mentioned herein are incorporated by reference in their entirety. Amino acid designations may include full name, three-letter, or single-letter designations as commonly understood by one of ordinary skill in the art to which this invention belongs. In case of conflict, the present specification, including definitions, will control. In addition, the materials, methods, and examples are illustrative only and not intended to be limiting.

Other features and advantages of the invention will be apparent from the following detailed description and from the claims.

Antimicrobial Polypeptides, Variant and Fragments of the Invention and Uses Thereof Cathelicidins are cationic polypeptides that have highly conserved N-terminal signal peptides and pro-regions (cathelin domains), and highly heterogeneous C-terminal antimicrobial domains (Zanetti, J. Leukoc. Biol., 75:39 (2004); Bals et al., Cell Mol. Life. Sci., 60:711 (2003); Zaiou et al., J. Invest. Dermatol., 120:810 (2003)). Cathelicidin host defense peptides are a prominent component of the antimicrobial capability of neutrophils, macrophages and mast cells (Agerberth et al., Blood, 96:3086 (2000); Larrick et al., J. Immunol., 152:231 (1994); Niyonsaba et al., Curr. Drug Targets Inflamm. Allergy, 2:224 (2003)), and are also key elements in the inherent defense mechanisms within epithelial cells of the lung, urinary bladder, gut, oral mucosa, skin, and testis (Zaiou et al., J. Mol. Med., 80:549 (2002); Gennaro et al., Biopolymers, 55:31 (2000)).

The invention is based on the discovery of a canine cathelicidin having broad spectrum antimicrobial activity including, without limitation, activity against Gram-positive and Gram-negative bacteria, protozoa, as well as yeast. Accordingly, the invention provides a canine cathelicidin antimicrobial polypeptide, a fragment thereof, a variant thereof or a fragment of the variant, an isolated nucleic acid molecule and an expression vector having the isolated nucleic acid molecule that encodes a canine cathelicidin polypeptide, a variant or a fragment of the invention, an isolated cell containing such a nucleic acid molecule and/or expression vector, a composition containing a canine cathelicidin polypeptide, variant or fragment of the invention, and an article of manufacture containing such a polypeptide, variant or fragment of the invention or a nucleic acid therefor. The invention also provides a method of producing a canine cathelicidin polypeptide, variant or fragment of the invention, a method of inhibiting growth of a microorganism using an antimicrobial polypeptide, variant or fragment, or nucleic acid molecule therefor, of the invention, and a method of treating a microbial infection in a vertebrate with an antimicrobial polypeptide, variant or fragment, or nucleic acid molecule therefore, of the invention. A polypeptide, variant or fragment of the invention can be obtained by isolation from a cell expressing the polypeptide, variant or fragment of the invention, can be chemically synthesized, or can be expressed from a recombinant nucleic acid molecule.

In one embodiment, the invention provides a polypeptide having broad spectrum antimicrobial activity. In one embodiment, the invention provides a purified canine cathelicidin polypeptide, e.g. a polypeptide having SEQ ID NO: 2 or 4. A canine cathelicidin polypeptide, variant or fragment of the invention has broad spectrum antimicrobial activity. The term "broad-spectrum," as used herein, refers to the ability to reduce or inhibit the survival or growth of various eukaryotic or prokaryotic microorganisms including, without limitation, Gram-positive and Gram-negative bacteria, yeast and protozoa. Examples of Gram-positive bacteria include, without limitation, members of the genera *Listeria* and *Staphylococcus*. Examples of Gram-negative bacteria include, without limitation, members of the genera *Escherichia, Klebsiella, Salmonella, Pseudomonas, Proteus, Treponema, Chlamydia*, and *Neisseria*. Examples of yeasts include, without limitation, members of the *Candida* genus. Examples of protozoas include, without limitation, members of the *Trichomonas* genus. The cathelicidin polypeptide of the invention has antimicrobial activity against various microorganisms including, without limitation, *Listeria monocytogenes, Staphylococcus aureus, Escherichia coli, Klebsiella pneumoniae, Salmonella typhimurium, Pseudomonas aeruginosa, Proteus mirabilis, Salmonella enteritidis, Neisseria gonorrhoeae, Ureaplasma canigenitalium* and *Ureaplasma urealyticum; Candida albicans; Treponema pallidum, Chlamydia trachomatis* and *Trichomonas vaginalis*.

A variant of a polypeptide of the invention may have certain amino acid sequence identity to SEQ ID NO: 4 and has antimicrobial activity, or is immunogenic, or both. The term "variant" includes polypeptides having an amino acid sequence that has at least 53% sequence identity to that of SEQ ID NO: 4.

As used herein, the term "% identity" or "sequence identity" refers to a relationship between two or more polypeptide sequences, as well as two or more polynucleotide sequences, namely a reference sequence and a given sequence to be compared with the reference sequence. Sequence identity is determined by comparing the given sequence to the reference sequence after the sequences have been optimally aligned to produce the highest degree of sequence similarity, as determined by the match between strings of such sequences. Upon such alignment, sequence identity is ascertained on a position-by-position basis, e.g., the sequences are "identical" at a particular position if at that position, the nucleotides or amino acid residues are identical. The total number of such position identities is then divided by the total number of nucleotides or residues in the reference sequence to give % sequence identity.

Sequence identity can be readily calculated by known methods, including but not limited to, those described in Computational Molecular Biology, Lesk, A. N., ed., Oxford University Press, New York (1988), Biocomputing: Informatics and Genome Projects, Smith, D. W., ed., Academic Press, New York (1993); Computer Analysis of Sequence Data, Part I, Griffin, A. M., and Griffin, H. G., eds., Humana Press, New Jersey (1994); Sequence Analysis in Molecular Biology, von Heinge, G., Academic Press (1987); Sequence Analysis Primer, Gribskov, M. and Devereux, J., eds., M. Stockton Press, New York (1991); and Carillo et al., Applied Math., 48:1073 (1988), the teachings of which are incorporated herein by reference.

Preferred methods to determine the sequence identity are designed to give the largest match between the sequences tested. Methods to determine sequence identity are codified in publicly available computer programs which determine sequence identity between given sequences. Examples of such programs include, but are not limited to, the GCG program package (Devereux, et al., Nucleic Acids Research, 12:387 (1984)), BLASTP, BLASTN™ and FASTA™ (Altschul et al., J. Molec. Biol., 215:403 (1990)). The BLASTX program is publicly available from NCBI and other sources (BLAST Manual, Altschul et al., NCVI NLM NIH Bethesda, MD 20894, Altschul et al., J. Molec. Biol., 215:403 (1990), the teachings of which are incorporated herein by reference). These programs optimally align sequences using default gap weights in order to produce the highest level of sequence identity between the given and reference sequences.

As an illustration, by a polypeptide having a given amino acid sequence having at least, for example, 95% sequence identity to a reference amino acid sequence, it is intended that the given amino acid sequence of the polypeptide is identical to the reference sequence except that the given polypeptide sequence may include up to 5 amino acid alterations per each 100 amino acids of the reference amino acid sequence. In other words, to obtain a given polypeptide sequence having at least 95% sequence identity with a reference amino acid sequence, up to 5% of the amino acid residues in the reference sequence may be deleted or substituted with another amino acid, or a number of amino acids up to 5% of the total number of amino acid residues in the reference sequence may be inserted into the reference sequence. These alterations of the reference sequence may occur at the amino or the carboxy terminal positions of the reference amino acid sequence or anywhere between those terminal positions, interspersed either individually among residues in the reference sequence or in the one or more contiguous groups within the reference sequence. Preferably, residue positions which are not identical differ by conservative amino acid substitutions. However, conservative substitutions are not included as a match when determining sequence identity.

A polypeptide of the invention can have an amino acid sequence that has greater than 52% identity with SEQ ID NO: 4, for example, at least 55%, at least 60%, at least 65%, at least 70%, at least 75%, at least 80%, at least 85%, at least 90%, at least 95%, or at least 97% identical to SEQ ID NO: 4.

Such variation in the sequence may be due to amino acid substitutions that do not significantly affect (a) the structure of the peptide backbone in the area of the substitution, (b) the charge or hydrophobicity of the molecule at the target site, or (c) the bulk of the side chain. Naturally-occurring amino acid residues are divided into groups based on common side-chain properties:

(1) hydrophobic: norleucine, met, ala, val, leu, ile;
(2) neutral hydrophilic: cys, ser, thr;
(3) acidic: asp, glu;
(4) basic: asn, gin, his, lys, arg;
(5) residues that influence chain orientation: gly, pro; and
(6) aromatic: trp, tyr, phe.

The replacement of one amino acid in a polypeptide sequence with another of a similar type as classified above is referred to as conservative amino acid substitution. As will be appreciated by those having skill in the art, the above classifications are not absolute. Several amino acids exhibit more than one characteristic property, and can therefore be included in more than one category. For example, tyrosine has both a nonpolar aromatic ring and a polar hydroxyl group. Thus, tyrosine has several characteristics that could be described as nonpolar or acidic. However, the nonpolar ring is dominant and so tyrosine is generally considered to be hydrophobic. Similarly, in addition to being able to form disulfide linkages, cysteine also has nonpolar character. Thus, while not strictly classified as a hydrophobic or nonpolar amino acid, in many instances cysteine can be used to confer hydrophobicity or nonpolarity to a peptide.

A polypeptide of the invention can have an amino acid sequence that corresponds to SEQ ID NO: 4 with 1 to 9 conservative amino acid substitutions as long as the polypeptide has the antimicrobial activity of SEQ ID NO: 4 and is immunogenic as defined herein.

Variations in the sequence of a polypeptide of the invention may also arise from non-conservative substitutions. Non-conservative substitutions entail exchanging a member of one of the classes described above for a member of another class. Such a variant can have amino acid substitutions at "non-essential" amino acid residues, that is, residues that can be altered or deleted in the wild-type sequence without abolishing antimicrobial activity. Such non-essential residues can be identified using methods described herein or methods known in the art, such as site specific mutagenesis or the generation of deletions/truncation mutants, followed by determination of biological activity and comparison with the wild type sequence as described below. Thus, when substitutions are introduced, the resulting variants can be tested to confirm or determine their levels of biological activity.

The term variant also includes an allelic variant of the canine cathelicidin of SEQ ID NO: 2 or 4. An allelic variant results from genetic polymorphism that naturally exists in the canine population. Genetic polymorphism and an example of a method for identifying an allelic variant of a polypeptide of the invention are described in the nucleic acids section.

A polypeptide of the invention can be a fragment of SEQ ID NO: 4, as well as a fragment of a variant of SEQ ID NO: 4, that has antimicrobial activity or is immunogenic. The term "fragment," as used to describe a polypeptide of the invention, refers to a segment of at least 15 contiguous amino acids of the reference sequence, i.e., SEQ ID NO: 4 or its variant sequence. A fragment is at least one amino acid less in length than the full-length amino acid sequence shown in SEQ ID NO: 4.

Accordingly, fragment of SEQ ID NO: 4 may have antimicrobial activity against one or more microorganisms against which SEQ ID NO: 4 is active. The antimicrobial activity may be microbicidal or microbiostatic and may be 10%, 20%, 30%, 40%, 50%, 60%, 70%, 80%, 90% or more than 90% of the activity of SEQ ID NO: 4 against one or more of, for example, *Listeria monocytogenes*, *Staphylococcus aureus*, *Escherichia coli*, *Klebsiella pneumoniae*, *Salmonella typhimurium*, *Pseudomonas aeruginosa*, *Proteus mirabilis*, *Salmonella ehteritidis*, *Neisseria gonorrhoeae*, *Ureaplasma canigenitalium*, *Ureaplasma urealyticum*, *Candida albicans*, *Treponema pallidum*, *Chlamydia trachomatis* and *Trichomonas vaginalis*.

Thus, a variant or fragment of SEQ ID NO: 4 may have the same antimicrobial activity profile as that of SEQ ID NO: 4, i.e., it has the same activity spectrum as SEQ ID NO: 4 in that it is active against the same group of organisms, in particular, *Listeria monocytogenes*, *Staphylococcus aureus*, *Escherichia coli*, *Klebsiella pneumoniae*, *Salmonella typhimurium*, *Pseudomonas aeruginosa*, *Proteus mirabilis*, *Salmonella enteritidis*, *Neisseria gonorrhoeae*, *Ureaplasma canigenitalium*, *Ureaplasma urealyticum*, *Candida albicans*, *Treponema pallidum*, *Chlamydia trachomatis* and *Trichomonas vaginalis*. Methods of determining activity against one or more microorganism are disclosed herein or known to those of skill in the art.

Non-limiting examples of fragments of SEQ ID NO: 4, as well as other polypeptides of the invention are provided in Table 1.

TABLE 1

| SEQ ID NO | Sequence |
|---|---|
| 4 | RLKELITTGGQKIGEKIRRIGQRIKDFFKNLQPREEKS |
| 6 | LKELITTGGQKIGEKIRRIGQRIKDFFKNLQPREEKS |
| 8 | KELITTGGQKIGEKIRRIGQRIKDFFKNLQPREEKS |
| 10 | ELITTGGQKIGEKIRRIGQRIKDFFKNLQPREEKS |
| 12 | LITTGGQKIGEKIRRIGQRIKDFFKNLQPREEKS |
| 14 | ITTGGQKIGEKIRRIGQRIKDFFKNLQPREEKS |
| 16 | RLKELITTGGQKIGEKIRRIGQRIKDFFKNLQP |
| 18 | RLKELITTGGQKIGEKIRRIGQRIKDFFKNLQPR |
| 20 | RLKELITTGGQKIGEKIRRIGQRIKDFFKNLQPRE |
| 22 | RLKELITTGGQKIGEKIRRIGQRIKDFFKNLQPREE |
| 24 | RLKELITTGGQKIGEKIRRIGQRIKDFFKNLQPREEK |
| 26 | DRLKELITTGGQKIGEKIRRIGQRIKDFFKNLQPREEKS |
| 28 | IDRLKELITTGGQKIGEKIRRIGQRIKDFFKNLQPREEKS |
| 30 | KIDRLKELITTGGQKIGEKIRRIGQRIKDFFKNLQPREEKS |
| 32 | KKIDRLKELITTGGQKIGEKIRRIGQRIKDFFKNLQPREEKS |

A polypeptide of the invention also includes a polypeptide that binds specifically to an antibody that binds specifically to a polypeptide having the amino acid sequence of SEQ ID NO:

4. Methods for producing an antibody that binds specifically to a polypeptide having the amino acid sequence of SEQ ID NO: 4 are known to those of skill in the art. Methods for determining whether an antibody binds to a selected antigen are known to those of skill in the art.

Derivatives

A polypeptide, variant or fragment of the invention can also be a fusion protein in which the polypeptide, variant or fragment of the invention, e.g. SEQ ID NO: 4, is further attached to an unrelated additional amino acids such as a polyhistidine tag, protein A, green fluorescent protein, glutathione-S-transferase (GST), a heterologous signal sequence for secretion (e.g. gp67, the phoA secretory signal, protein A), or other functional amino acid domain that facilitates purification, detection or other useful property. In a fusion protein of the invention, the unrelated, heterologous polypeptide may be attached to the amino- or carboxy-terminus of the antimicrobial polypeptide, variant or fragment of the invention. An example of a method for generating a fusion polypeptide is discussed in below in the nucleic acids section.

A polypeptide of the invention may include one or more non-naturally occurring amino acids, one or more proteogenic (i.e. the amino acid can be incorporated into a protein in a cell through a metabolic pathway) or non-proteogenic amino acids such that the resulting derivative polypeptide has extended stability, enhanced activity or other useful property when compared to the corresponding unmodified polypeptide.

Thus, reference herein to an amino acid includes, for example, naturally-occurring proteogenic (L)-amino acids, as well as (D)-amino acids, chemically-modified amino acids such as amino acid analogs, naturally-occurring non-proteogenic amino acids such as norleucine, and chemically-synthesized compounds having properties known in the art to be characteristic of an amino acid. The term amino acid also includes amino acids that are not encoded by the genetic code such as, for example, beta-alanine (beta-Ala), or other omega-amino acids, such as 3-aminopropionic, 2,3-diaminopropionic (2,3-diaP), 4-aminobutyric and so forth, alpha-aminoisobutyric acid (Aib), sarcosine (Sar), ornithine (Orn), citrulline (Cit), t-butylalanine (t-BuA), t-butylglycine (t-BuG), N-methylisoleucine (N-MeIle), phenylglycine (Phg), and cyclohexylalanine (Cha), norleucine (Nle), 2-naphthylalanine (2-Nal); 1,2,3,4-tetrahydroisoquinoline-3-carboxylic acid (Tic); beta-2-thienylalanine (Thi); methionine sulfoxide (MSO); homoarginine (Har); phosphoserine; phosphothreonine; phosphotyrosine; hydroxyproline; gamma-carboxyglutamate; hippuric acid; octahydroindole-2-carboxylic acid; statine; penicillamine, α-methyl-alanine, para-benzoyl-phenylalanine; hydroxyproline, carboxyglutamate and propargylglycine. Other modifications include the reduction of cysteinyl thiol groups with 2-mercaptoethanol and carboxymethylated with iodoacetamide as described by Lambden et al. (1981).

A polypeptide of the invention can also include, without limitation, a polypeptide having a chemical modification such as PEGylation (i.e. covalent coupling to polyethylene glycol), alkylation, acylation, carbamylation, iodination, esterification, amidation, reduction, protection, or any other modification known to improve its stability and/or bioavailability. Formyl-methionine, pyroglutamine and trimethyl-alanine may be substituted at the N-terminal residue of the polypeptide. Other amino-terminal modifications include aminooxypentane modifications (see Simmons et al., Science, 276:276 (1997)).

The term derivative also includes a polypeptide in which one or more amide linkages ($-CO-NH-$) have been replaced with another linkage such as $-CH_2NH-$, $-CH_2S-$, $-CH_2CH_2$, $-CH=CH-$(cis and trans), $-COCH_2-$, $-CH(OH)CH_2-$ and $-CH_2SO-$. This replacement can be made by methods known in the art (see, for example, Spatola, Vega Data Vol. 1, Issue 3, (1983); Spatola, in Chemistry and Biochemistry of Amino Acids Peptides and Proteins, Weinstein, ed., Marcel Dekker, New York, p. 267 (1983); Morley, Trends Pharm. Sci. pp. 463 468 (1980); Hudson et al., Int. J. Pept. Prot. Res., 14:177 (1979); Spatola et al., Life Sci., 38:1243 (1986); Hann, J. Chem. Soc. Perkin Trans., 1:307 (1982); Almquist et al., J. Med. Chem., 23:1392 (1980); Jennings-White et al., Tetrahedron Lett., 23:2533 (1982); Szelke et al., EP 45665 (1982); Holladay et al., Tetrahedron Lett., 24:4401 1983); and Hruby, Life Sci., 31:189 (1982)). Such a derivative polypeptide can include, without limitation, one or more modified amino acids, for example, hydroxyproline, carboxyglutamate, or those discussed above, as well as amino acids that are not linked by peptide. A derivative polypeptide also includes a polypeptide in which one or more amide linkages in the reference polypeptide ($-CO-NH-$) have been replaced with another linkage such as $-CH_2NH-$, $-CH_2S-$, $-CH_2CH_2$, $-CH=CH-$(cis and trans), $-COCH_2-$, $-CH(OH)CH_2-$ and $-CH_2SO-$. This replacement can be made by methods known in the art (see, for example, Spatola, Vega Data Vol. 1, Issue 3, (1983); Spatola, in Chemistry and Biochemistry of Amino Acids Peptides and Proteins, Weinstein, ed., Marcel Dekker, New York, p. 267 (1983); Morley, Trends Pharm. Sci. pp. 463 468 (1980); Hudson et al., Int. J. Pept. Prot. Res., 14:177 (1979); Spatola et al., Life Sci., 38:1243 (1986); Hann, J. Chem. Soc. Perkin Trans., 1:307 (1982); Almquist et al., J. Med. Chem., 23:1392 (1980); Jennings-White et al., Tetrahedron Lett., 23:2533 (1982); Szelke et al., EP 45665 (1982); Holladay et al., Tetrahedron Lett., 24:4401 (1983); and Hruby, Life Sci., 31:189 (1982)).

Methods of Making a Polypeptide, Variant or Fragment of the Invention

A polypeptide, variant or fragment of the invention may be synthesized in vitro, e.g., by the solid phase peptide synthetic method or by enzyme catalyzed peptide synthesis, or with the aid of recombinant DNA technology using a nucleic acid of the invention described below. Solid phase peptide synthetic method is an established and widely used method, which is described in references such as the following: Stewart et al., Solid Phase Peptide Synthesis, W. H. Freeman Co., San Francisco (1969); Merrifield, J. Am. Chem. Soc. 85:2149 (1963); Meienhofer in "Hormonal Proteins and Peptides," ed.; C. H. Li, Vol. 2 (Academic Press, 1973), pp. 48-267; and Bavaay and Merrifield, "The Peptides," eds. E. Gross and F. Meienhofer, Vol. 2 (Academic Press, 1980) pp. 3-285. These peptides can be further purified by fractionation on immunoaffinity or ion-exchange columns; ethanol precipitation; reverse phase HPLC; chromatography on silica or on an anion-exchange resin such as DEAE; chromatofocusing; SDS-PAGE; ammonium sulfate precipitation; gel filtration using, for example, Sephadex G-75; ligand affinity chromatography; or crystallization or precipitation from non-polar solvent or nonpolar/polar solvent mixtures. Purification by crystallization or precipitation is preferred.

Once isolated and characterized, derivatives, e.g., chemically derived derivatives, of a given recombinant polypeptide can be readily prepared using methods well known to the art. One method is to prepare derivatives which are cyclized peptides (see EPA 471,453 (amide bonds); EPA 467,701 (disulfide bonds); EPA 467,699 (thioether bonds)). Other modifications are disclosed in Jameson et al. (Nature, 368:744 (1994)); U.S. Pat. Nos. 4,992,463; and 5,091,396. For example, to cyclize peptides by oxidation of free cysteinyl thiol groups, peptide (0.1 mg mL$^{-1}$) is reacted for 1 hour at 0° C. with iodine (1 mM in methanol) and the oxidation is then quenched with sodium thiosulphate. The mixture is subjected to reverse-phase HPLC on a semi-preparative Zorbax™ C8 column, followed by gel filtration on a Zorbax™ GF250 column. Two peaks which are separated by the gel filtration step were further analyzed by mass spectroscopy, using an Applied Biosystems Biolon 20 Biopolymer plasma desorption time-of-flight Mass Analyzer. The first peak is resolved by mass analysis into two species, a partially protected monomer peptide and a dimeric peptide. The material is tested for free cysteine thiol groups with Ellman's reagent [5,5-dithiobis(2-nitrobenzoic acid); Sigma] at the highest concentration of peptide before saturation (20 mg mL$^{-1}$). This peak represents the cyclic peptide and is stored at pH 4.0 at −20° C. until used (see Tam & Lu (1989)).

Amides of the polypeptide may also be prepared by techniques well known in the art for converting a carboxylic acid group or precursor, to an amide. A preferred method for amide formation at the C-terminal carboxyl group is to cleave the peptide from a solid support with an appropriate amine, or to cleave in the presence of an alcohol, yielding an ester, followed by aminolysis with the desired amine.

N-acyl derivatives of an amino group of the polypeptide of the invention may be prepared by utilizing an N-acyl protected amino acid for the final condensation, or by acylating a protected or unprotected peptide. O-acyl derivatives may be prepared, for example, by acylation of a free hydroxy peptide or peptide resin. Either acylation may be carried out using standard acylating reagents such as acyl halides, anhydrides, acyl imidazoles, and the like. Both N-acylation and O-acylation may be carried out together, if desired.

Salts of carboxyl groups of a polypeptide of the invention may be prepared in the usual manner by contacting the polypeptide with one or more equivalents of a desired base such as, for example, a metallic hydroxide base, e.g., sodium hydroxide; a metal carbonate or bicarbonate base such as, for example, sodium carbonate or sodium bicarbonate; or an amine base such as, for example, triethylamine, triethanolamine, and the like.

Acid addition salts of the polypeptide or variant polypeptide, or of amino residues of the peptide or variant peptide, may be prepared by contacting the peptide or amine with one or more equivalents of the desired inorganic or organic acid, such as, for example, hydrochloric acid. Esters of carboxyl groups of the peptides may also be prepared by any of the usual methods known in the art.

A polypeptide of the invention can also be produced by expression from recombinant nucleic acids as described below in the section on expression vectors and host cells. When a polypeptide of the invention is expressed in a recombinant cell, it is necessary to purify the recombinant peptide from other cell proteins or polypeptides to obtain preparations that are substantially homogenous as to the recombinant polypeptide of the invention. For example, the culture medium or lysate can be centrifuged to remove particulate cell debris. The membrane and soluble protein fractions are then separated. The polypeptide of the invention may then be purified from the soluble protein fraction. Alternatively, the polypeptide of the invention may be purified from the insoluble fraction, i.e., refractile bodies (see, for example, U.S. Pat. No. 4,518,526), if necessary. The polypeptide of the invention may be purified from contaminant soluble or membrane proteins and polypeptides by fractionation on immunoaffinity or ion-exchange columns; ethanol precipitation; reverse phase HPLC; chromatography on silica or on an anion-exchange resin such as DEAE; chromatofocusing; SDS-PAGE; ammonium sulfate precipitation; gel filtration using, for example, Sephadex G-75; or ligand affinity chromatography, and the like.

If expressed as a fusion polypeptide, the fusion polypeptide may be purified by methods specific for the cathelicidin portion of the fusion polypeptide. For example, if the fusion polypeptide is a histidine tagged fusion polypeptide, Ni-NTA resin may be employed to purify the fusion polypeptide.

The polypeptide of the invention can also be prepared by in vitro transcription and translation reactions. An expression cassette can be employed to generate gene-specific transcripts which are subsequently translated in vitro so as to result in a preparation of substantially homogenous polypeptide of the invention. The construction of vectors for use in vitro transcription/translation reactions, as well as the methodologies for such reactions, are well known to the art.

Nucleic Acid Molecules of the Invention

The invention also provides isolated nucleic acid molecules that encode a canine cathelicidin polypeptide, a variant or a fragment thereof. Accordingly, a nucleic acid molecule of the invention can encode polypeptide having an amino acid sequence of SEQ ID NO: 2 or 4, an amino acid sequence of a variant of SEQ ID NO: 4, or fragment thereof. An example of a nucleic acid molecule of the invention that can encode polypeptide having an amino acid sequence of SEQ ID NO: 2 or 4 is a nucleic acid having the nucleotide sequence of SEQ ID NO: 1 or 3. Non-limiting examples of nucleic acid molecules of the invention include the following:

TABLE 2

| SEQ ID NO | Sequence |
|---|---|
| 3 | cggctgaa agagctcatc acgacagggg ggcagaagat tggcgaaaag attaggagaa ttggccagag aatcaaggat tttttaaga atcttcagcc cagggaggag aagtcctaa |
| 5 | ctgaa agagctcatc acgacagggg ggcagaagat tggcgaaaag attaggagaa ttggccagag aatcaaggat tttttaaga atcttcagcc cagggaggag aagtcctaa |
| 7 | aa agagctcatc acgacagggg ggcagaagat tggcgaaaag attaggagaa ttggccagag aatcaaggat tttttaaga atcttcagcc cagggaggag aagtcctaa |
| 9 | gagctcatc acgacagggg ggcagaagat tggcgaaaag attaggagaa ttggccagag aatcaaggat tttttaaga atcttcagcc cagggaggag aagtcctaa |
| 11 | ctcatc acgacagggg ggcagaagat tggcgaaaag attaggagaa ttggccagag aatcaaggat tttttaaga atcttcagcc cagggaggag aagtcctaa |
| 13 | atc acgacagggg ggcagaagat tggcgaaaag attaggagaa ttggccagag aatcaaggat tttttaaga atcttcagcc cagggaggag aagtcctaa |
| 15 | cggctgaa agagctcatc acgacagggg ggcagaagat tggcgaaaag attaggagaa ttggccagag aatcaaggat tttttaaga atcttcagcc c |
| 17 | cggctgaa agagctcatc acgacagggg ggcagaagat tggcgaaaag attaggagaa ttggccagag aatcaaggat tttttaaga atcttcagcc cagg |

TABLE 2-continued

| SEQ ID NO | Sequence |
|---|---|
| 19 | cggctgaa agagctcatc acgacagggg<br>ggcagaagat tggcgaaaag attaggagaa ttggccagag<br>aatcaaggat tttttttaaga atcttcagcc cagggag |
| 21 | cggctgaa agagctcatc acgacagggg<br>ggcagaagat tggcgaaaag attaggagaa ttggccagag<br>aatcaaggat tttttttaaga atcttcagcc cagggaggag |
| 23 | cggctgaa agagctcatc acgacagggg<br>ggcagaagat tggcgaaaag attaggagaa ttggccagag<br>aatcaaggat tttttttaaga atcttcagcc cagggaggag<br>aag |
| 25 | g accggctgaa agagctcatc acgacagggg<br>ggcagaagat tggcgaaaag attaggagaa ttggccagag<br>aatcaaggat tttttttaaga atcttcagcc cagggaggag<br>aagtcctaa |
| 27 | attg accggctgaa agagctcatc acgacagggg<br>ggcagaagat tggcgaaaag attaggagaa ttggccagag<br>aatcaaggat tttttttaaga atcttcagcc cagggaggag<br>aagtcctaa |
| 29 | aaaattg accggctgaa agagctcatc acgacagggg<br>ggcagaagat tggcgaaaag attaggagaa ttggccagag<br>aatcaaggat tttttttaaga atcttcagcc cagggaggag<br>aagtcctaa |
| 31 | aagaaaattg accggctgaa agagctcatc acgacagggg<br>ggcagaagat tggcgaaaag attaggagaa ttggccagag<br>aatcaaggat tttttttaaga atcttcagcc cagggaggag<br>aagtcctaa |

A nucleic acid that encodes a canine cathelicidin polypeptide variant includes a degenerate variant, as well as an allelic variant.

The term "degenerate variant," as used herein to describe a nucleic acid, means that, as a result of the degeneracy of the genetic code, the nucleic acid has a nucleotide sequence that differs from SEQ ID NO: 1 or 3, but still encodes a polypeptide having the amino acid sequence of SEQ ID NO: 2 or 4, respectively. A degenerate variant includes a nucleic acid molecule having a sequence that reflects the codon usage preference in a selected host cell expression system. Thus, a nucleic acid variant that is designed to reflect codon usage preference of a particular host cell does not exhibit alterations at the amino acid level.

The term "allelic variant," as used herein, to describe a nucleic acid of the invention, means that, as a result of genetic polymorphism, the nucleic acid that is an allelic variant of SEQ ID NO: 1 or 3 differs from the sequence of SEQ ID NO: 1 or 3 in such a way that the encoded polypeptide differs from SEQ ID NO: 2 or 4 respectively. Genetic polymorphism exists among individuals within a population, e.g. a canine population, due to natural allelic variation and leads to changes in the amino acid sequence of a particular polypeptide within a population, e.g. the canine population. Such natural allelic variation typically results in 1-5% variance in the nucleotide sequence of a given gene. As used herein, the term "gene" refers to a nucleic acid molecule that comprises an open reading frame encoding a polypeptide of the invention. An allele is one of a group of genes that occur alternatively at a given genetic locus. An allelic variant can be identified by (1) using hybridization probes of the invention (discussed above) to identify and isolate the same genetic locus in a variety of individual canines and then (2) sequencing the gene encoding canine cathelicidin in a number of different individuals in the canine population. Any and all such nucleotide variations and resulting amino acid polymorphisms or variations that are the result of natural allelic variation and that do not alter the functional activity are intended to be within the scope of the invention.

A nucleic acid variant also includes a nucleic acid that encodes a polypeptide having an amino acid sequence that is at least 53% identical to SEQ ID NO: 4. Thus, the nucleic acid variant may encode a polypeptide having an amino acid sequence that is at least 55%, at least 60%, at least 65%, at least 70%, at least 75%, at least 80%, at least 85%, at least 90%, at least 95%, or at least 97% identical to SEQ ID NO: 4.

Examples of such nucleic acid variants include those nucleic acids that have nucleotide sequences of at least 70%, preferably, at least 75%, 80%, 85%, 90%, 95% or more than 95% identity to SEQ ID NO: 1 or 3.

A nucleic acid molecule of the invention can also have a nucleotide sequence that hybridizes under highly stringent conditions or moderately stringent conditions to a nucleic acid sequence that encodes SEQ ID NO: 4 or its complement. An example of such a nucleic acid molecule is one that hybridizes under highly stringent conditions or moderately stringent conditions to a hybridization probe, the nucleotide sequence of which is the complement of SEQ ID NO: 1 or 3.

"The term "hybridize" means the formation of a stable duplex between a first nucleic acid molecule and a second nucleic acid molecule under a particular condition. The stability of the duplex depends on the hybridization condition, which is defined by temperature, ionic strength, and the presence of other compounds such as organic solvents. Generally, the lower the salt concentration and the higher the wash temperature, the more stringent is the hybridization/washing condition. Stringency may also be adjusted by changing the concentrations of salt, SDS or organic components, while maintaining the hybridization and wash temperature at 65° C. Under highly stringent or in high stringency condition, only nucleic acids that have 95% to 100% complementary bases will form stable duplexes. Under moderate stringency or in moderately stringent condition, only nucleic acids that have at least 75% complementary sequences will form stable duplexes.

Moderate and high stringency conditions refer to hybridization in 6× sodium chloride/sodium citrate (SSC) at 45° C., followed by washing in 0.2×SSC, 0.1% SDS, at 48° C. or 65° C., respectively.

A nucleic acid molecule of the invention can also be a fragment of SEQ ID NO: 1 or 3 that (1) is sufficient for use as a hybridization probe to identify nucleic acid molecules encoding a polypeptide of the invention or (2) is suitable for use as a primer for polymerase chain reaction (PCR) for the amplification or mutation of nucleic acid molecules. Such a fragment typically comprises a region of nucleotide sequence that hybridizes under stringent conditions to the sense or antisense strand of a nucleic acid having the nucleotide sequence of SEQ ID NO: 1 or 3, and will not hybridize under stringent conditions to unrelated nucleic acids as discussed above. Examples of such fragments include, without limitation, SEQ ID NO: 3, 5, 7, 9, 11, 13, 15, 17, 19, 21, 23, 25, 27, 29, 31 and 33 shown in Table 2.

A nucleic acid molecule of the invention can also be modified at the base moiety, sugar moiety, or phosphate backbone to improve, for example, the stability, hybridization, or solubility of the molecule. For example, when used as a probe or primer, nucleic acids of the invention can comprise a label group such as a radioisotope, a fluorescent compound, an enzyme or an enzyme cofactor, a hybridization-triggered cleavage agent, or a hybridization-triggered linking agent.

Such a label could be incorporated to facilitate transport across the cell membrane or to facilitate detection. Nucleic acids of the invention can also be operably linked to an expression control sequence such as described below.

Methods of Making Nucleic Acids Encoding Cathelicidins

A nucleic acid molecule of the present invention such as one having the nucleotide sequence of SEQ ID NO: 1 or 3 can be isolated using standard molecular biology techniques and the sequence information provided herein.

Sources of nucleotide sequences encoding cathelicidin, a fragment or a variant thereof, or the nucleic acid complement thereof, include RNA, or genomic DNA or cDNA from any canine tissue, e.g., from physiological fluid or tissue. Other sources of the DNA molecules of the invention include genomic or cDNA libraries derived from a canine. Moreover, the present DNA molecules also may be prepared in vitro, e.g., by synthesizing an oligonucleotide of about 215, preferably about 100, more preferably about 50, nucleotides in length, or by subcloning a portion of a DNA segment that encodes a canine cathelicidin.

A nucleic acid molecule encoding a polypeptide of the invention can be identified and isolated using standard methods, as described by Sambrook et al., Molecular Cloning: A Laboratory Manual, Cold Spring Harbor, N.Y. (1989). For example, reverse-transcriptase PCR (RT-PCR) can be employed to isolate and clone cathelicidin cDNAs. A primer which is complementary to an RNA encoding canine cathelicidin, and preferably hybridizes to the 3N two-thirds of the RNA, can be employed as a primer in a reverse transcriptase reaction to prepare first-strand cDNAs from isolated RNA which contains RNA sequences of interest. RNA can be isolated by methods known to the art, e.g., using TRIZOL™ reagent (GIBCO-BRL/Life Technologies, Gaithersburg, Md.). Resultant first-strand cDNAs are then amplified in PCR reactions.

"Polymerase chain reaction" or "PCR" refers to a procedure or technique in which amounts of a preselected fragment of nucleic acid, RNA and/or DNA, are amplified as described in U.S. Pat. No. 4,683,195. Generally, sequence information from the ends of the region of interest or beyond is employed to design oligonucleotide primers comprising at least 7-8 nucleotides. These primers will be identical or similar in sequence to opposite strands of the template to be amplified. PCR can be used to amplify specific RNA sequences, specific DNA sequences from total genomic DNA, and cDNA transcribed from total cellular RNA, bacteriophage or plasmid sequences, and the like. See generally Mullis et al., Cold Spring Harbor Symp. Quant. Biol., 51:263 (1987); Erlich, ed., PCR Technology, (Stockton Press, New York, 1989). Thus, PCR-based cloning approaches rely upon conserved sequences deduced from alignments of related gene or polypeptide sequences. However, other amplification-based methods known to the art may also be employed, including, but not limited to, self-sustained sequence-specific replication (3SR) (Gebinoga et al., Eur. J. Biochem., 235:256 (1996); Fahy et al., PCR Methods Appl, 1:25 (1991); Guatelli et al., Proc. Nat'l Acad. Sci. U.S.A., 87:1874 (1990)), nucleic acid sequence-based amplification (NASBA) (Compton, Nature, 350:91 (1991)), strand displacement amplification (SDA) (Walker et al., Proc. Nat'l Acad. Sci. U.S.A., 89:392 (1992); Walker et al., Nucl. Acid Res., 20:1691 (1992)), probe cyclization (Landgren, Trends in Gen., 9:199 (1993)), or a Q beta replicase, Sp6, T7, or T3 RNA polymerase based amplification system. See, for example, U.S. Pat. Nos. 5,622,820, 5,629,153, 5,532,126, 5,573,914 and 5,514,545.

Primers are made to correspond to highly conserved regions of peptides or nucleotide sequences which were identified and compared to generate the primers, e.g., by a sequence comparison of other cathelicidin genes. One primer is prepared which is predicted to anneal to the antisense strand, and another primer prepared which is predicted to anneal to the sense strand, of a DNA molecule which encodes canine cathelicidin.

The products of each PCR reaction are separated via an agarose gel and all consistently amplified products are gel-purified and cloned directly into a suitable vector, such as a known plasmid vector. The resultant plasmids are subjected to restriction endonuclease and dideoxy sequencing of double-stranded plasmid DNAs. Alternatively, the gel-purified fragment can be directly sequenced.

cDNA or genomic libraries can be screened using the colony hybridization procedure. Generally, each microtiter plate is replicated onto duplicate nitrocellulose filter papers and colonies are allowed to grow at 37° C. for 14-16 hours on L agar containing 50 µg/mL Amp. The colonies are lysed and DNA fixed to the filter by sequential treatment for 5 minutes with 500 mM NaOH, 1.5 M NaCl, and are washed twice for 5 minutes each time with 5× standard saline citrate (SSC). Filters are air dried and baked at 80° C. for 2 hours. The duplicate filters are prehybridized at 42° C. for 6-8 hours with 10 mL per filter of DNA hybridization buffer (5×SSC, pH 7.0, 5×Denhardt's solution (polyvinylpyrrolidine, plus Ficoll and bovine serum albumin; 1×=0.02% of each), 50 mM sodium phosphate buffer at pH 7.0, 0.2% SDS, 20 µg/mL Poly U, and 50 µg/mL denatured salmon sperm DNA).

The samples can be hybridized with kinased probe under conditions which depend on the stringency desired. Typical moderately stringent conditions employ a temperature of 42° C. for 24-36 hours with 1-5 mL/filter of DNA hybridization buffer containing probe. For higher stringencies, high temperatures and shorter times are employed. Generally, the filters are washed four times for 30 minutes each time at 37° C. with 2×SSC, 0.2% SDS and 50 mM sodium phosphate buffer at pH 7, then are washed twice with 2×SSC and 0.2% SDS, air dried, and are autoradiographed at −70° C. for 2 to 3 days.

Recovery or isolation of a given fragment of DNA from a restriction digest can employ separation of the digest on polyacrylamide or agarose gel by electrophoresis, identification of the fragment of interest by comparison of its mobility versus that of marker DNA fragments of known molecular weight, removal of the gel section containing the desired fragment, and separation of the gel from DNA. See Lawn et al., Nucleic Acids Res., 9:6103 (1981), and Goeddel et al., Nucleic Acids Res., 8, 4057 (1980).

Accordingly, using all or a portion of SEQ ID NO: 3 as a hybridization probe, a nucleic acid molecule of the invention can be isolated using standard hybridization and cloning techniques. A nucleic acid molecule of the invention can be amplified using cDNA, mRNA or genomic DNA as a template and appropriate oligonucleotide primers according to standard PCR amplification techniques. The nucleic acid so amplified can be cloned into an appropriate vector and characterized by DNA sequence analysis. Oligonucleotides corresponding to all or a portion of a nucleic acid molecule of the invention can be prepared by standard synthetic techniques, e.g. using an automated DNA synthesizer.

A nucleic acid encoding a "biologically active fragment" of a polypeptide of the invention can be prepared by isolating a portion of any of SEQ ID NO: 1, e.g. SEQ ID NO: 3, 5, 7, 9, 11, 13, 15, 17, 19, 21, 23, 25, 27, 29, 31 and 33 that encodes a polypeptide having a biological activity, expressing the encoded fragment of the polypeptide, e.g. by recombinant expression in vitro, and assessing the activity of the encoded portion of the polypeptide using methods described herein or known in the art.

Methods of Making Cathelicidin Nucleic Acid Sequence Variants

Nucleic acid molecules encoding amino acid sequence variants of canine cathelicidin are prepared by a variety of methods known in the art. These methods include, but are not limited to, isolation from a natural source (in the case of naturally-occurring amino acid sequence variants or allelic variants) or preparation by oligonucleotide-mediated (or site-directed) mutagenesis, PCR mutagenesis, and cassette mutagenesis of an earlier prepared variant or a non-variant version of canine cathelicidin.

Oligonucleotide-mediated mutagenesis is a preferred method for preparing amino acid substitution variants of canine cathelicidin. This technique is well known in the art as described by Adelman et al., DNA, 2:183 (1983). Briefly, canine cathelicidin DNA is altered by hybridizing an oligonucleotide encoding the desired mutation to a DNA template, where the template is the single-stranded form of a plasmid or bacteriophage containing the unaltered or native DNA sequence of canine cathelicidin. After hybridization, a DNA polymerase is used to synthesize an entire second complementary strand of the template that will thus incorporate the oligonucleotide primer, and will code for the selected alteration in the canine cathelicidin DNA.

Generally, oligonucleotides of at least 25 nucleotides in length are used. An optimal oligonucleotide will have 12 to 15 nucleotides that are completely complementary to the template on either side of the nucleotide(s) coding for the mutation. This ensures that the oligonucleotide will hybridize properly to the single-stranded DNA template molecule. The oligonucleotides are readily synthesized using techniques known in the art such as that described by Crea et al., Proc. Natl. Acad. Sci. U.S.A., 75:5765 (1978).

The DNA template can be generated by those vectors that are either derived from bacteriophage M13 vectors (the commercially available M13 mp18 and M13 mp19 vectors are suitable), or those vectors that contain a single-stranded phage origin of replication as described by Viera et al., Meth. Enzymol., 153:3 (1987). Thus, the DNA that is to be mutated may be inserted into one of these vectors to generate single-stranded template. Production of the single-stranded template is described in Sections 4.21-4.41 of Sambrook et al., Molecular Cloning: A Laboratory Manual (Cold Spring Harbor Laboratory Press, New York, 1989).

Alternatively, single-stranded DNA template may be generated by denaturing double-stranded plasmid (or other) DNA using standard techniques.

For alteration of the native DNA sequence (to generate amino acid sequence variants, for example), the oligonucleotide is hybridized to the single-stranded template under suitable hybridization conditions. A DNA polymerizing enzyme, usually the Klenow fragment of DNA polymerase I, is then added to synthesize the complementary strand of the template using the oligonucleotide as a primer for synthesis. A heteroduplex molecule is thus formed such that one strand of DNA encodes the mutated form of canine cathelicidin, and the other strand (the original template) encodes the native, unaltered sequence of canine cathelicidin. This heteroduplex molecule is then transformed into a suitable host cell, usually a prokaryote such as E. coli JM101. After the cells are grown, they are plated onto agarose plates and screened using the oligonucleotide primer radiolabeled with 32-phosphate to identify the bacterial colonies that contain the mutated DNA. The mutated region is then removed and placed in an appropriate vector for peptide or polypeptide production, generally an expression vector of the type typically employed for transformation of an appropriate host.

The method described immediately above may be modified such that a homoduplex molecule is created wherein both strands of the plasmid contain the mutations(s). The modifications are as follows: The single-stranded oligonucleotide is annealed to the single-stranded template as described above. A mixture of three deoxyribonucleotides, deoxyriboadenosine (dATP), deoxyriboguanosine (dGTP), and deoxyribothymidine (dTTP), is combined with a modified thiodeoxyribocytosine called dCTP-(αS) (which can be obtained from the Amersham Corporation). This mixture is added to the template-oligonucleotide complex. Upon addition of DNA polymerase to this mixture, a strand of DNA identical to the template except for the mutated bases is generated. In addition, this new strand of DNA will contain dCTP-(αS) instead of dCTP, which serves to protect it from restriction endonuclease digestion.

After the template strand of the double-stranded heteroduplex is nicked with an appropriate restriction enzyme, the template strand can be digested with ExoIII nuclease or another appropriate nuclease past the region that contains the site(s) to be mutagenized. The reaction is then stopped to leave a molecule that is only partially single-stranded. A complete double-stranded DNA homoduplex is then formed using DNA polymerase in the presence of all four deoxyribonucleotide triphosphates, ATP, and DNA ligase. This homoduplex molecule can then be transformed into a suitable host cell such as E. coli JM101.

For example, a preferred embodiment of the invention is an isolated and purified DNA molecule comprising nucleic acid encoding canine cathelicidin having SEQ ID NO:4, wherein the DNA segment comprises SEQ ID NO:3, or variants of SEQ ID NO:3, having nucleotide substitutions which are "silent". That is, when silent nucleotide substitutions are present in a codon, the same amino acid is encoded by the codon with the nucleotide substitution as is encoded by the codon without the substitution. For example, valine is encoded by the codons GTT, GTC, GTA and GTG. A variant of SEQ ID NO: 1 at the fourth codon in the prepro form of the polypeptide (GTT in SEQ ID NO:1) includes the substitution of GTC, GTA or GTG for GTT. Other "silent" nucleotide substitutions in SEQ ID NO:3 which can encode a polypeptide corresponding to SEQ ID NO:4 can be ascertained by reference to FIG. 3 and page D1 in Appendix D in Sambrook et al., Molecular Cloning: A Laboratory Manual (1989). Nucleotide substitutions can be introduced into DNA segments by methods well known to the art. See, for example, Sambrook et al., supra. Likewise, nucleic acid molecules encoding other canine cathelicidins may be modified in a similar manner. Thus, nucleic acid molecules encoding at least a portion of canine cathelicidin, or the complement thereto, may be modified so as to yield nucleic acid molecules of the invention having silent nucleotide substitutions, or to yield nucleic acid molecules having nucleotide substitutions that result in amino acid substitutions.

Expression Vectors and Host Cells

A nucleic acid of the invention can also be in the form of an expression vector in which a nucleic acid encoding a polypeptide of the invention is operably linked to an expression control sequence. The term "vector" refers to a nucleic acid molecule capable of transporting another nucleic acid to which it has been linked. An example of a vector is a "plasmid," a circular double stranded DNA molecule into which additional DNA molecules can be ligated. Another example is a viral vector in which additional DNA segments can be ligated into the viral genome. Certain vectors are capable of autonomous replication in a host cell into which they are introduced, e.g. bacterial vectors having a bacterial origin of replication and episomal mammalian vectors, while other vectors, e.g. non-episomal mammalian vectors, are integrated into the genome of a host cell upon introduction into the host cell, and thus replicate along with the host genome. Certain vectors, in particular expression vectors, are capable of directing the expression of genes to which they are operably linked.

The expression vector of the invention comprises a nucleic acid of the invention in a form suitable for expression of the nucleic acid in a host cell. The expression vector includes one or more regulatory sequences, selected based on the host cell to be used for expression, operably-linked to the nucleic acid sequence to be expressed.

The term "operably linked," as used herein, means a coding sequence and a regulatory sequence such as a promoter, operator, enhancer, or other expression control sequences are connected in such a way that permits expression from the coding sequence when the appropriate molecules such as transcriptional activator proteins are bound to the regulatory sequence. Thus, "operably linked" means that the nucleotide sequence of interest, e.g. the sequence encoding the polypeptide of the invention, is linked to the regulatory sequence(s) in a manner which allows for expression of the nucleotide sequence, for example, in a host cell when the vector is introduced into the host cell or in an in vitro transcription/translation system.

The term "regulatory sequence" includes, without limitation, promoters, operators, enhancers and other expression control elements such as polyadenylation signals. Regulatory sequences are known in the art and can direct constitutive expression of a nucleic acid of the invention in many types of host cell or only in certain host cells (e.g. the tissue-specific regulatory sequences). The choice and design of an expression vector depends on factors that include the level of expression of the polypeptide of the invention and expression system to be used, e.g. the host cell, e.g. prokaryotic or eukaryotic (mammalian, yeast), or in vitro transcription/translation using, for example, T7 system.

The invention also provides a host cell into which a recombinant expression vector has been introduced. The term "host cell" refers to a well-characterized homogenous, biologically-pure population of cells, which can be prokaryotic or eukaryotic. The eukaryotic cells may be of mammalian origin, as well as plant, insect, yeast, or fungal origin. Eukaryotic cells may be neoplastic or "immortalized" in vitro by methods known in the art, as well as primary cells. The host cell may be prokaryotic, preferably of bacterial origin. Prokaryotic hosts most frequently are represented by various strains of *E. coli*. However, other microbial strains may also be used, such as bacilli, for example, *Bacillus subtilis*, various species of *Pseudomonas*, or other bacterial strains. The term "host cell" refers to the particular cell into which the expression vector has been introduced, as well as the progeny or potential progeny of such a cell. Such a progeny may be identical to the parent cell, or may contain modifications that occur in succeeding generations due to mutations or environmental influences.

Expression vectors can be introduced into host cell using conventional transformation or transfection techniques including, without limitation, calcium phosphate or calcium chloride co-precipitation, DEAE-dextran-mediated transfection, lipofection, electroporation, or any commercially available methods for introducing nucleic acids into a cell.

"Transfected" or "transformed" is used herein to include any host cell or cell line, the genome of which has been altered or augmented by the presence of at least one preselected DNA sequence, which DNA is also referred to in the art of genetic engineering as "heterologous DNA," "recombinant DNA," "exogenous DNA," "genetically engineered," "non-native," or "foreign DNA," wherein said DNA was isolated and introduced into the genome of the host cell or cell line by the process of genetic engineering. The host cells of the present invention are typically produced by transfection with a DNA sequence in a plasmid expression vector, a viral expression vector, or as an isolated linear DNA sequence. Preferably, the transfected DNA is a chromosomally integrated recombinant DNA sequence, which comprises a gene encoding a polypeptide of the invention or its complement, which host cell may or may not express significant levels of autologous or "native" cathelicidin.

To confirm the presence of the preselected DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a polypeptide of the invention, e.g., by immunological means (ELISAs and Western blots) or by assays described herein.

Pharmaceutical Compositions and Article of Manufacture

In one embodiment, the invention provides a pharmaceutical composition comprising a polypeptide, variant or fragment thereof, or a nucleic acid molecule therefore, of the invention. To prepare such a pharmaceutical composition, a polypeptide, variant or fragment thereof, or a nucleic acid molecule therefore, of the invention is synthesized or otherwise obtained, purified as necessary or desired and then lyophilized and stabilized. The polypeptide, variant or fragment thereof, or a nucleic acid molecule therefore, can then be adjusted to the appropriate concentration and then combined with other agent(s) or pharmaceutically acceptable carrier(s). By "pharmaceutically acceptable" it is meant a carrier, diluent, excipient, and/or salt that is compatible with the other ingredients of the formulation, and not deleterious to the recipient thereof.

Pharmaceutical formulations containing a therapeutic polypeptide, variant or fragment thereof of the invention can be prepared by procedures known in the art using well-known and readily available ingredients. For example, the polypeptide can be formulated with common excipients, diluents, or carriers, and formed into tablets, capsules, solutions, suspensions, powders, aerosols and the like. Examples of excipients, diluents, and carriers that are suitable for such formulations include buffers, as well as fillers and extenders such as starch, cellulose, sugars, mannitol, and silicic derivatives. Binding agents can also be included such as carboxymethyl cellulose, hydroxymethylcellulose, hydroxypropyl methylcellulose and other cellulose derivatives, alginates, gelatin, and polyvinyl-pyrrolidone.

Moisturizing agents can be included such as glycerol, disintegrating agents such as calcium carbonate and sodium bicarbonate. Agents for retarding dissolution can also be included such as paraffin. Resorption accelerators such as quaternary ammonium compounds can also be included. Surface active agents such as cetyl alcohol and glycerol monostearate can be included. Adsorptive carriers such as kaolin and bentonite can be added. Lubricants such as talc, calcium and magnesium stearate, and solid polyethyl glycols can also be included. Preservatives may also be added. The compositions of the invention can also contain thickening agents such as cellulose and/or cellulose derivatives. They may also contain gums such as xanthan, guar or carbo gum or gum arabic, or alternatively polyethylene glycols, bentones and montmorillonites, and the like.

For oral administration, a polypeptide, variant or fragment thereof, may be present as a powder, a granular formulation, a solution, a suspension, an emulsion or in a natural or synthetic polymer or resin for ingestion of the active ingredients from a chewing gum. The active polypeptide may also be presented as a bolus, electuary or paste. The formulations may, where appropriate, be conveniently presented in discrete unit dosage forms and may be prepared by any of the methods well known to the pharmaceutical arts including the step of mixing the therapeutic agent with liquid carriers, solid matrices, semi-solid carriers, finely divided solid carriers or combinations thereof, and then, if necessary, introducing or shaping the product into the desired delivery system. The total active ingredients in such formulations comprise from 0.1 to 99.9% by weight of the formulation.

Tablets or caplets containing the polypeptide, variant or fragment thereof of the invention can include buffering agents such as calcium carbonate, magnesium oxide and magnesium carbonate. Caplets and tablets can also include inactive ingredients such as cellulose, pre-gelatinized starch, silicon dioxide, hydroxy propyl methyl cellulose, magnesium stearate, microcrystalline cellulose, starch, talc, titanium dioxide, benzoic acid, citric acid, corn starch, mineral oil, polypropylene glycol, sodium phosphate, zinc stearate, and the like. Hard or soft gelatin capsules containing at least one peptide of the invention can contain inactive ingredients such as gelatin, microcrystalline cellulose, sodium lauryl sulfate, starch, talc, and titanium dioxide, and the like, as well as liquid vehicles such as polyethylene glycols (PEGs) and vegetable oil. Moreover, enteric-coated caplets or tablets containing one or more peptides of the invention are designed to resist disintegration in the stomach and dissolve in the more neutral to alkaline environment of the duodenum.

Orally administered therapeutic polypeptide, variant or fragment thereof of the invention can also be formulated for sustained release. In this case, a peptide of the invention can be coated, micro-encapsulated (see WO 94/07529, and U.S. Pat. No. 4,962,091), or otherwise placed within a sustained delivery device. A sustained-release formulation can be designed to release the active peptide, for example, in a particular part of the intestinal or respiratory tract, possibly over a period of time. Coatings, envelopes, and protective matrices may be made, for example, from polymeric substances, such as polylactide-glycolates, liposomes, microemulsions, microparticles, nanoparticles, or waxes. These coatings, envelopes, and protective matrices are useful to coat indwelling devices, e.g., stents, catheters, peritoneal dialysis tubing, draining devices and the like.

A polypeptide, variant or fragment thereof of the invention can also be formulated as elixirs or solutions for convenient oral administration or as solutions appropriate for parenteral administration, for instance by intramuscular, subcutaneous, intraperitoneal or intravenous routes. A pharmaceutical formulation of a therapeutic peptide of the invention can also take the form of an aqueous or anhydrous solution or dispersion, or alternatively the form of an emulsion or suspension or salve.

Thus, a polypeptide, variant or fragment thereof, or a nucleic acid molecule therefore, may be formulated for parenteral administration (e.g., by injection, for example, bolus injection or continuous infusion) and may be presented in unit dose form in ampoules, pre-filled syringes, small volume infusion containers or in multi-dose containers. As noted above, preservatives can be added to help maintain the shelve life of the dosage form. The active polypeptide and other ingredients may form suspensions, solutions, or emulsions in oily or aqueous vehicles, and may contain formulatory agents such as suspending, stabilizing and/or dispersing agents. Alternatively, the active polypeptide and other ingredients may be in powder form, obtained by aseptic isolation of sterile solid or by lyophilization from solution, for constitution with a suitable vehicle, e.g., sterile, pyrogen-free water, before use.

These formulations can contain pharmaceutically acceptable carriers, vehicles and adjuvants that are well known in the art. It is possible, for example, to prepare solutions using one or more organic solvent(s) that is/are acceptable from the physiological standpoint, chosen, in addition to water, from solvents such as acetone, ethanol, isopropyl alcohol, glycol ethers such as the products sold under the name "Downanol™," polyglycols and polyethylene glycols, $C_1$-$C_4$ alkyl esters of short-chain acids, ethyl or isopropyl lactate, fatty acid triglycerides such as the products marketed under the name "Miglyol™," isopropyl myristate, animal, mineral and vegetable oils and polysiloxanes.

It is possible to add, if necessary, an adjuvant chosen from antioxidants, surfactants, other preservatives, film-forming, keratolytic or comedolytic agents, perfumes, flavorings and colorings. Antioxidants such as t-butylhydroquinone, butylated hydroxyanisole, butylated hydroxytoluene and α-tocopherol and its derivatives can be added.

In some embodiments the polypeptide, variant or fragment thereof, are formulated as a microbicide, which is administered topically or to mucosal surfaces such as the vagina, the rectum, eyes, nose and the mouth. For topical administration, the therapeutic agents may be formulated as is known in the art for direct application to a target area. Forms chiefly conditioned for topical application take the form, for example, of creams, milks, gels, dispersion or microemulsions, lotions thickened to a greater or lesser extent, impregnated pads, ointments or sticks, aerosol formulations (e.g., sprays or foams), soaps, detergents, lotions or cakes of soap. Thus, in one embodiment, a polypeptide of the invention can be formulated as a vaginal cream or a microbicide to be applied topically. Other conventional forms for this purpose include wound dressings, coated bandages or other polymer coverings, ointments, creams, lotions, pastes, jellies, sprays, and aerosols. Thus, the therapeutic peptides of the invention can be delivered via patches or bandages for dermal administration. Alternatively, the polypeptide can be formulated to be part of an adhesive polymer, such as polyacrylate or acrylate/vinyl acetate copolymer. For long-term applications it might be desirable to use microporous and/or breathable backing laminates, so hydration or maceration of the skin can be minimized. The backing layer can be any appropriate thickness that will provide the desired protective and support functions. A suitable thickness will generally be from about 10 to about 200 microns.

Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents. The active peptides can also be delivered via iontophoresis, e.g., as disclosed in U.S. Pat. Nos. 4,140,122; 4,383,529; or 4,051,842. The percent by weight of a therapeutic agent of the invention present in a topical formulation will depend on various factors, but generally will be from 0.01% to 95% of the total weight of the formulation, and typically 0.1-85% by weight.

Drops, such as eye drops or nose drops, may be formulated with one or more of the polypeptide, variant or fragment thereof, in an aqueous or non-aqueous base also comprising one or more dispersing agents, solubilizing agents or suspending agents. Liquid sprays are conveniently delivered from pressurized packs. Drops can be delivered via a simple eye dropper-capped bottle, or via a plastic bottle adapted to deliver liquid contents dropwise, via a specially shaped closure.

The polypeptide, variant or fragment thereof, may further be formulated for topical administration in the mouth or throat. For example, the active ingredients may be formulated as a lozenge further comprising a flavored base, usually sucrose and acacia or tragacanth; pastilles comprising the composition in an inert base such as gelatin and glycerin or sucrose and acacia; and mouthwashes comprising the composition of the present invention in a suitable liquid carrier.

The pharmaceutical formulations of the present invention may include, as optional ingredients, pharmaceutically acceptable carriers, diluents, solubilizing or emulsifying agents, and salts of the type that are available in the art. Examples of such substances include normal saline solutions such as physiologically buffered saline solutions and water. Specific non-limiting examples of the carriers and/or diluents that are useful in the pharmaceutical formulations of the present invention include water and physiologically acceptable buffered saline solutions such as phosphate buffered saline solutions pH 7.0-8.0.

The polypeptide, variant or fragment thereof, or a nucleic acid molecule therefore, of the invention can also be administered to the respiratory tract. Thus, the present invention also provides aerosol pharmaceutical formulations and dosage forms for use in the methods of the invention. In general, such dosage forms comprise an amount of at least one of the agents of the invention effective to treat or prevent the clinical symptoms of infection. Any statistically significant attenuation of one or more symptoms of the infection that has been treated pursuant to the method of the present invention is considered to be a treatment of such infection within the scope of the invention.

Alternatively, for administration by inhalation or insufflation, the composition may take the form of a dry powder, for example, a powder mix of the therapeutic agent and a suitable powder base such as lactose or starch. The powder composition may be presented in unit dosage form in, for example, capsules or cartridges, or, e.g., gelatin or blister packs from which the powder may be administered with the aid of an inhalator, insufflator, or a metered-dose inhaler (see, for example, the pressurized metered dose inhaler (MDI) and the dry powder inhaler disclosed in Newman, S. P. in Aerosols and the Lung, Clarke, S. W. and Davia, D. eds., pp. 197-224, Butterworths, London, England, 1984).

A polypeptide, variant or fragment thereof, or a nucleic acid molecule therefore, of the present invention can also be administered in an aqueous solution when administered in an aerosol or inhaled form. Thus, other aerosol pharmaceutical formulations may comprise, for example, a physiologically acceptable buffered saline solution containing between about 0.001 mg/in L and about 100 mg/mL of one or more of the peptides of the present invention specific for the indication or disease to be treated. Dry aerosol in the form of finely divided solid peptide or nucleic acid particles that are not dissolved or suspended in a liquid are also useful in the practice of the present invention. Polypeptides of the present invention may be formulated as dusting powders and comprise finely divided particles having an average particle size of between about 1 and 5 µm, alternatively between 2 and 3 µm. Finely divided particles may be prepared by pulverization and screen filtration using techniques well known in the art. The particles may be administered by inhaling a predetermined quantity of the finely divided material, which can be in the form of a powder. It will be appreciated that the unit content of active ingredient or ingredients contained in an individual aerosol dose of each dosage form need not in itself constitute an effective amount for treating the particular infection, indication or disease since the necessary effective amount can be reached by administration of a plurality of dosage units. Moreover, the effective amount may be achieved using less than the dose in the dosage form, either individually, or in a series of administrations.

For administration to the upper (nasal) or lower respiratory tract by inhalation, the polypeptide, variant or fragment thereof, or a nucleic acid molecule therefore, of the invention is conveniently delivered from a nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Nebulizers include, but are not limited to, those described in U.S. Pat. Nos. 4,624,251; 3,703,173; 3,561,444; and 4,635,627. Aerosol delivery systems of the type disclosed herein are available from numerous commercial sources including Fisons Corporation (Bedford, Mass.), Schering Corp. (Kenilworth, N.J.) and American Pharmoseal Colo., (Valencia, Calif). For intra-nasal administration, the therapeutic agent may also be administered via nose drops, a liquid spray, such as via a plastic bottle atomizer or metered-dose inhaler. Typical of atomizers are the Mistometer™ (Wintrop) and the Medihaler™ (Riker).

A polypeptide, variant or fragment thereof, or a nucleic acid molecule therefore, of the invention may also be used in combination with one or more known therapeutic agents, for example, a pain reliever; an antiviral agent; an antibacterial agent; an anti-cancer agent; an anti-inflammatory agent; an antihistamine; a bronchodilator and appropriate combinations thereof, whether for the conditions described or some other condition.

The invention also provides an article of manufacture comprising a pharmaceutical composition or polypeptide of the invention labeled for use in inhibiting growth of a microbe or labeled for use to treat a food-borne illness or a sexually-transmitted disease such as those described herein. Such an article of manufacture comprises a vessel containing a pharmaceutical composition or polypeptide of the invention as well as fragments, variants or derivatives thereof, and instructions for use of such composition or polypeptide for treatment of a food-borne illness or sexually-transmitted disease. The instructions could be in the form of a label included with packaging material or printed on the packaging material.

Miscellaneous Compositions and Articles of Manufacture

In one embodiment, the invention provides an article of manufacture that includes a composition containing a polypeptide, variant or fragment thereof, or a nucleic acid molecule therefore, of the invention.

Such articles may be food packaging materials. Non-limiting examples include casings; flexible plastics; rigid cardboard, paper, and wood products in boxes; flexible papers, e.g. bags; rigid metals in cans and drums; flexible metals, e.g. aluminum foils; laminates or multi-layers that combine paper, plastic and foil; glass jars and bottles; and plastic jars and bottles. A peptide or composition of the invention may be incorporated into food packaging materials during the manufacturing of the packaging materials. The peptide or composition can be incorporated into the matrix of the packing material or it may be applied as a coating to the internal surface of the packaging material.

Articles that may include a polypeptide, variant or fragment of the invention may be a fresh or processed, or prepackaged food item. Non-limiting examples include canned foods, frozen foods, dehydrated foods, prepackaged meat, partially prepared foods, ready-to-serve foods and dry mixes.

A composition comprising a polypeptide, variant or fragment thereof, or a nucleic acid molecule therefore, of the invention may be in the form of an encapsulated powder or spray solution containing a polypeptide, variant or fragment thereof, or a nucleic acid molecule therefore, of the invention. A composition comprising a polypeptide of the invention may include a food additive such as another antimicrobial agent, an antioxidant, a natural or artificial color, a natural or artificial flavor or flavor enhancer, a bleaching agent, a chelating agent, a nutrient additive, a thickening or stabilizing agent, or any combination thereof. The food additive may be calcium propionate, propyl gallate, peroxides, citric acid, malic acid, tartaric acid, thiamin, riboflavin, niacin, lecithin, acesulfame-K, acetic acid, acetone peroxide, adipic acid, agar, algin, potassium aluminum phosphate, ammonium sulfate, amylase, annatto extract, ascorbic acid, ascorbyl palmitate, aspartame, benzaldehyde,benzoyl peroxide, beta-carotene, butylated hydroxyanisole (BHA), butylated hydroxytoluene (BHT), biotin, potassium bromate, caffeine, calcium chloride, calcium caseinate, calcium iodate, calcium pantothenate, calcium phosphate, calcium propionate, calcium saccharin, calcium silicate, calcium stearoyl lactylate, calcium sulfate, carboxymethylcellulose, carob bean gum, carrageenan, carrageen, carnauba wax, cellulose gum (carboxymethyl cellulose), chlorine dioxide, citric acid, cobalamin, cyanocobalamin, corn syrup, corn syrup solids, dextrin, dextrose, glucose, diglycerides and monoglycerides, dipotassium phosphate, disodium EDTA, disodium guanylate, disodium inosinate, ethylenediamine tetraacetic acid, tartrazine (FD & C yellow # 5), FD & C yellow # 6, ferric lactate, ferric oxide, ferric phosphate, ferric sodium, ferric sulphate, fluoride, folacin or folic acid, fructose (levulose), fumaric acid, fungaryl protease, furcelleran, gelatin, glucose, glycerin/glycerol, glycerol monostearate, guar gum, gum Arabic, heptyl paraben, high fructose, hydrochloric acid, hydrogen peroxide, hydrolyzed vegetable protein, invertase, invert sugar, iodine, isopropyl citrate, L cysteine, lactalbumin, lactic acid, lactobacillus bulgaricus, lactose, lecithin, levulose, licorice, locust bean gum, magnesium carbonate, malic acid, mannitol, methyl anthranilate, monocalcium phosphate, monoglycerides, monosodium glutamate, monostearate, nitrates and nitrites, nutmeg, oxystearin, pantothenyl alcohol, menthyl parabens, propyl parabens, heptyl parabens, petrolatum, phosphoric acid, polydextrose, polysorbate 60, polysorbate 80, potassium aluminum sulfate, potassium bisulfite, potassium bromate, potassium carbonate, potassium citrate, potassium iodate, potassium metabisulfite, potassium phosphate, potassium sorbate, propionates, propionic acid, propyl gallate, propylene glycol, pyrophosphates, quinine, saccharin, sodium chloride, saltpeter, silicon dioxide sodium acid pyrophosphate, sodium alginate, sodium aluminum phosphate, sodium ascorbate, sodium benzoate, sodium bicarbonate, sodium bisulfite, sodium caseinate, sodium citrate, sodium erythorbate, sodium metabisulfite, sodium nitrates/nitrites, sodium phosphate, sodium propionate, sodium pyrophosphate, sodium silicoaluminate, sodium stearoyl lactylate, sodium sulfite and bisulfite, sodium stearoyl fumarate, sodium tripolyphosphate, sorbates/sorbic acid, sorbitol, soy protein, stannous chloride, starch, modified starch, sucrose, sucrose polyester, sulfites, sugar, sulfur dioxide, tannin, tannic acid, tartaric acid, textured vegetable protein, titanium dioxide, tocopherols, tragacanth gum, tricalcium phosphate, vanilla, vanillin, ethyl vanillin, vinegar, vitamin C, vitamin D, vitamin E, whey, xanthan gum, or any combination thereof.

Other articles of manufacturing may include a therapeutically useful device such as a vaginal ring, a condom, a bandage or a similar therapeutic device. The device holds a therapeutically effective amount of a pharmaceutical composition for controlling the growth or survival of the microorganism. The device may be packaged in a kit along with instructions for use. The pharmaceutical composition includes at least one polypeptide, variant or fragment of the present invention, in a therapeutically effective amount such that infection is controlled.

Methods of the Invention

A nucleic acid molecule and/or host cell of the invention can be used to produce a polypeptide, variant or fragment thereof, of the invention. Accordingly, the invention provides a method for producing a polypeptide, variant or fragment thereof, using the nucleic acid molecule and host cell of the invention. The method comprises culturing a host cell into which a nucleic acid molecule of the invention has been introduced in a suitable medium such that the polypeptide, variant or fragment is produced. The method may further involve purifying the polypeptide, variant or fragment from the medium or the host cell.

Other uses of a nucleic acid molecule of the invention include use as hybridization probes or primers for detecting, identifying or generating a nucleic acid encoding a polypeptide of the invention. Methods of detecting, identifying and generating a nucleic acid of the invention are known in the art and also described herein. These methods include, without limitation, nucleic hybridization techniques, e.g. southern, northern hybridization, plaque or colony hybridization in library screening; PCR amplification and nucleic acid sequencing.

A polypeptide, variant or fragment thereof of the invention can also be used as an immunogen to generate specific antibody. The term "antibody" refers to an immunoglobin molecule, e.g. a monoclonal antibody, and an immunologically active portion of an immunoglobulin molecule. A monoclonal antibody is a population of antibody molecules that binds specifically with a particular antigen epitope. Immunologically active portions of immunoglobulin molecules include F(ab) and F(ab')2 fragments. Both the full-length polypeptide of SEQ ID NO: 2 or a biologically active fragment such as SEQ ID NO: 4 can be used to generate a specific antibody. An antibody directed against a polypeptide of the invention is a specific antibody, and as such, it will bind with at least 50% or greater affinity, preferably about 75% or greater affinity, and more preferably, about 90% or greater affinity, to a polypeptide of SEQ ID NO: 4 than to a polypeptide having less than 10% identity to SEQ ID NO: 4.

The immunogenic polypeptide, variant or fragment thereof of the invention comprises at least 20, preferably 30, 40, 50, 60 or more than 60, contiguous amino acid residues of the amino acid sequence of SEQ ID NO: 2 or 4 that encompass an epitope of the polypeptide such that an antibody raised against the epitope forms a specific immune complex with the polypeptide.

Methods to generate antibodies are well known in the art. For example, a polyclonal antibody can be prepared by immunizing a suitable mammal with a purified polypeptide of the invention or an immunogenic fragment thereof. The mammal can be, for example, a rabbit, goat, or mouse. The polypeptide or antigenic fragment may be expressed using recombinant DNA technology, prepared by chemical synthesis, or purified using standard protein purification techniques. At the appropriate time after immunization, antibody molecules can be isolated from the mammal, e.g. from the blood or other fluid of the mammal, and further purified using standard techniques that include, without limitation, precipitation using ammonium sulfate, gel filtration chromatography, ion exchange chromatography or affinity chromatography using protein A. In addition, the antibody-producing cells of the mammal can be isolated and used to prepare hybridoma cells that secrete monoclonal antibodies specific to a polypeptide of the invention. Techniques for preparing monoclonal antibody-secreting hybridoma cells are known in the art. See, for example, Kohler and Milstein, Nature, 256:495 (1975) and Kozbor et al. Immunol Today, 4:72 (1983). Monoclonal antibodies can also be prepared using other methods known in the art, such as, for example, expression from a recombinant DNA molecule, or screening of a recombinant combinatorial immunoglobulin library using a polypeptide of the invention. Accordingly, the invention also provides a method of making an antibody comprising immunizing a non-human animal with an immunogenic fragment of SEQ ID NO: 2 or 4.

Antibodies so generated can be used to identify and purify polypeptides of the invention, including identifying the polypeptides of the invention that are allelic variants of SEQ ID NO: 2 or 4.

A polypeptide, variant or fragment thereof, or a nucleic acid molecule therefore, of the invention can be used as a microbicidal or microbiostatic agent as described above. It can be used to reduce or inhibit the survival or growth of a microorganism. The term "inhibit" includes a decrease in any detectable amount, for example, 5%, 10%, 20%, 40% or more than 40%, and can be determined by count, such as a bacterial culture or viral titer, or by evaluation of one or more symptoms associated with infection by a microorganism. Symptoms associated with infection by a microorganism such as a bacterium, yeast or protozoa are known to those in the art. Such symptoms are unique to a particular infectious microorganism and the resulting condition. Conditions against which a polypeptide of the invention may be used include, without limitation, food-borne illnesses and sexually transmitted disease (STD).

Microorganisms against which a polypeptide of the invention is active include prokaryotic and eukaryotic cells such as Gram-negative and Gram-positive bacteria, yeast and protozoa. Non-limiting examples include *Listeria monocytogenes, Staphylococcus aureus, Escherichia coli, Klebsiella pneumoniae, Salmonella typhimurium, Pseudomonas aeruginosa, Proteus mirabilis, Salmonella enteritidis, Neisseria gonorrhoeae, Ureaplasma canigenitalium, Ureaplasma urealyticum, Candida albicans, Trichomonas vaginalis, Treponema pallidum* or *Chlamydia trachomatis*, or a spoilage organism. Examples of minimum inhibitory concentrations (MIC) of a polypeptide of the invention against *Neisseria gonorrhoeae* (ATCC10150) and *Ureaplasma* canigenitalium (ATCC51252) are MIC's of at least about 0.25 µM, more preferably at least about 0.10 µM, and most preferably at least about 0.06 µM. Other examples of the MIC's of a polypeptide of the invention against various microorganisms are summarized in Table 4. MIC antimicrobial activity refers to complete inhibition of the growth of a microorganism, as judged by the naked eye, after a selected period of incubation. The method used to determine MIC is that set forth in Sang et al., Infection and Immunity, 2611-20 (May, 2005).

A "vertebrate" includes, without limitation, a fish, an amphibian, a bird as well as a mammal. Thus, a vertebrate can be a dog, cat, cow, horse, sheep, monkey, chimp, gorilla, mouse, pig, chicken, fish and human. Thus, in one embodiment, the invention provides a method of limiting the transmission of a microbial infection among vertebrates. In another embodiment, the invention provides method for treating a microbial infection in a vertebrate. The microbial infection could result in a skin infection, a food borne illness or a sexually-transmitted disease. Non-limiting examples include gonorrhoeae, syphilis, *Chlamydia*, food-poisoning, Candidiasis, pneumonia, bronchitis, oral lesions, Trichomoniasis, or oral or vaginal thrush. Thus, the invention also provides a method for treating disease conditions associated with infection by any of the above identified microorganism.

Methods of reducing or inhibiting survival or growth of a microorganism involve contacting the microorganism with an effective amount of a polypeptide, variant or fragment thereof, or a nucleic acid molecule therefore, of the invention. A composition that can support growth or survival of the microorganism may be contacted with an effective amount of the polypeptide, variant or fragment thereof, or a nucleic acid molecule therefore, of the invention in a variety of ways. For example, if the composition is a food item, the polypeptide of the invention may be added directly to the food, it may be incorporated into the matrix of the packaging material or it may be coated onto the packaging material, in which case the polypeptide may be released during storage, upon dissolution of the encapsulation material, contact with moisture or at a predetermined temperature. If the composition is a body fluid, the polypeptide of the invention may be added directly to the body fluid.

A vertebrate may be contacted with the polypeptide, variant or fragment thereof, or a nucleic acid molecule therefore, in a variety of ways including, without limitation, administration using the following route: oral, parenteral (including subcutaneous, intravenous, intramuscular and intraperitoneal), rectal, vaginal, dermal, transdermal (topical), transmucosal, intrathoracic, intrapulmonary and intranasal (respiratory) routes. The means of administration may be by injection, using a pump or any other appropriate mechanism.

A polypeptide, variant or fragment thereof, or a nucleic acid molecule therefore, of the invention may be administered to a vertebrate in a single dose, in multiple doses, in a continuous or intermittent manner, depending, for example, upon the recipient's physiological condition, whether the purpose of the administration is therapeutic or prophylactic, and other factors known to skilled practitioners. The administration of the peptides of the invention may be essentially continuous over a pre-selected period of time or may be in a series of spaced doses. Both local and systemic administration is contemplated.

The dosage to be administered to a vertebrate may be any amount appropriate to reduce or prevent infection or to treat at least one symptom associated with the infection. Some factors that determine appropriate dosages are well known to those of ordinary skill in the art and may be addressed with routine experimentation. For example, determination of the physicochemical, toxicological and pharmacokinetic properties may be made using standard chemical and biological assays and through the use of mathematical modeling techniques known in the chemical, pharmacological and toxicological arts. The therapeutic utility and dosing regimen may be extrapolated from the results of such techniques and through the use of appropriate pharmacokinetic and/or pharmacodynamic models. Other factors will depend on individual patient parameters including age, physical condition, size, weight, the condition being treated, the severity of the condition, and any concurrent treatment. The dosage will also depend on the agent chosen and whether prevention or treatment is to be achieved, and if the agent is chemically modified. Such factors can be readily determined by the clinician.

The precise amount to be administered to a vertebrate will be the responsibility of the attendant physician. However, to achieve the desired effect(s), an agent of the invention, or a combination thereof, may be administered as single or divided dosages, for example, of at least about 0.01 mg/kg to about 500 to 750 mg/kg, of at least about 0.01 mg/kg to about 300 to 500 mg/kg, at least about 0.1 mg/kg to about 100 to 300 mg/kg or at least about 1 mg/kg to about 50 to 100 mg/kg of body weight, although other dosages may provide beneficial results.

The absolute weight of a given polypeptide, variant or fragment thereof of the invention included in a unit dose can vary widely. For example, about 0.01 to about 2 g, or about 0.1 to about 500 mg, of at least one polypeptide of the invention, or a plurality of polypeptides can be administered. Alternatively, the unit dosage can vary from about 0.01 g to about 50 g, from about 0.01 g to about 35 g, from about 0.1 g to about 25 g, from about 0.5 g to about 12 g, from about 0.5 g to about 8 g, from about 0.5 g to about 4 g, or from about 0.5 g to about 2 g.

Daily doses of the polypeptide, variant or fragment thereof, of the invention can vary as well. Such daily doses can range, for example, from about 0.1 g/day to about 50 g/day, from about 0.1 g/day to about 25 g/day, from about 0.1 g/day to about 12 g/day, from about 0.5 g/day to about 8 g/day, from about 0.5 g/day to about 4 g/day, and from about 0.5 g/day to about 2 g/day.

A polypeptide, variant or fragment thereof, or a nucleic acid molecule therefore, of the invention may be used alone or in combination with a second medicament. The second medicament can be a known antibacterial agent such as a β-lactam, macrolide or other antibiotics, e.g. Azithromycin, Doxycycline, Tetracycline, and Erythromycin; an antifungal agent such as clotrimazole, nystatin, fluconazole, ketoconazole, amphotericin B, caspofungin, or voriconazole; an agent effective against a protozoan such as, for example, Metronidazole or timidazole. The second medicament may also be an antiviral agent such as Abacavir, Acyclovir, Amantadine, Didanosine, Emtricitabine, Enfuvirtide, Entecavir, Ganciclovir, Gardasil, Lamivudine, Nevirapine, Nelfinavir, Oseltamivir, Ribavirin, Rimantadine, Ritonavir, Stavudine, Valaciclovir, Vidarabine, Zalcitabine, and Zidovudine. The effective amount of the second medicament will follow the recommendations of the second medicament manufacturer, the judgment of the attending physician and will be guided by the protocols and administrative factors for amounts and dosing as indicated in the PHYSICIAN-S DESK REFERENCE.

The effectiveness of the method of treatment can be assessed by monitoring the vertebrate for signs or symptoms of the microbial infection as discussed above, as well as determining the presence and/or amount of microorganism present in the blood, e.g. the cell count, using methods known in the art including, without limitation, polymerase chain reaction, transcription mediated amplification or cell culturing.

The invention is further described in the following examples, which do not limit the scope of the invention described in the claims.

EXAMPLES

Example 1

Identification and Cloning of K9CATH Gene

The cDNA identification of K9CATH was established by mining the National Center for Biotechnology Information GenBank™. Complementary DNA sequences of human hCAP18/LL-37 (GenBank™ accession Number NM004345), bovine cathelicidin 1 (NM174825), and porcine PR-39 (L23825), were aligned, and a degenerate primer pair was designed to specifically target the conserved sequence encoding the pre-proregion of the corresponding polypeptides. Primers (forward, 5'-TCACTGKTGCTYCTGCTGCT-3' (SEQ ID NO: 39), and reverse, 5'-TGGCCTGGTYSARG-GTSACTGT-3' (SEQ ID NO: 40); where Y=C or T, K=G or T, S=C or G, and R=A or G) correspond to positions 40-59 and 241-262, respectively (Table 3), relative to the translation start codon of the human gene.

TABLE 3

RACE and RT-PCR primers for K9CATH

| Primer name | Sequence (SEQ ID NO) | Location in cDNA (nt) | Product size (bp) | GenBank ™ accession number |
|---|---|---|---|---|
| RACE primers | | | | |
| Sense outer primer | 5'-TCACTGKTGCTYCTGCTGCT-3' (SEQ ID NO: 39) | 180-199 | | NM004345 |
| Antisense outer primer | 5'-TGGCCTGGTYSARGGTSACTGT-3' (SEQ ID NO: 40) | 493-472 | 293 | NM004345 |
| Sense inner primer | 5'-CCTTAGCTACAGGGAGGCTGTG-3' (SEQ ID NO: 41) | 133-154 | | AY392089 |
| Antisense inner primer | 5'-GACTGTCCCTTCACACTGTTTCAC-3' (SEQ ID NO: 42) | 373-350 | 241 | AY392089 |

Using the designed primers and total RNA from the screened tissues as template, a one-step RT-PCR reaction (AccessQuick™ RT-PCR system, Promega) was performed producing a fragment of K9CATH cDNA. The amplification product was sequenced with an ABI 3700 DNA Analyzer at the K-State Sequencing and Genotyping Facility (Manhattan, Kans.) and confirmed to encode an open reading frame (ORF) with homology to known cathelicidins. To obtain the full-length cDNA, a modified rapid amplification of cDNA ends (RACE) protocol, which selects for non-truncated 5'-capped mRNAs (Ambion, FirstChoice™ RLM-RACE kit) was used. 5'-RACE was obtained by reverse transcription of total RNA (from bone marrow, spleen and testes independently) followed by two rounds of PCR with nested primers corresponding to the 5'-end adapter sequence and two nested antisense primers (i.e., the above mentioned reverse primer, and the inner reverse primer 5'-GACTGTCCCTTCACACT-GTTTCAC-3' (SEQ ID NO: 42)).

A similar strategy was used for 3'-RACE with nested primers corresponding to the 3'-end adapter and two nested sense primers (i.e. the above mentioned forward primer and the inner forward primer 5'-CCTTAGCTACAGGGAGGCT-GTG-3' (SEQ ID NO: 41)) (Table 3). Nested PCR products were purified by a column-based PCR purification kit (Qiagen), and cloned into plasmids using the pGEM®-T Easy Vector System (Promega). A 5'- or 3'-cDNA RACE sequence was generated from sequencing at least five clones. The full-length cDNA was then generated by ligation of 5'- and 3'-sequences and deletion of the adaptor and overlapped region. The efficiency of the RT procedure was standardized by assurance of comparable levels of the house-keeping gene GAPDH, amplified with PCR.

Based on the highly conserved cathelin-domain sequences, a set of primers was designed using the aligned sequences of human, bovine and porcine cathelicidins. This set of primers successfully amplified cathelicidin sequences from human, porcine, and canine bone marrow cells. The amplified band from canine bone marrow displayed a similar size range as the bands for human LL-37 and porcine PR-39 (FIG. 1A). The sequence of the cDNA amplicon from canine bone morrow mRNA showed more than 80% similarity to the related regions in equine, porcine and human cathelicidins (Agerberth et al., Blood, 96:3086 (2000); Scocchi et al., FEBS Lett., 417:311(1997); Scott et al., J. Immunol., 169:3883 (2002)). Using gene-specific primers based on the canine cDNA sequence, the full-length cDNA sequence of the putative canine cathelicidin was identified. The complete cDNA sequence and the translated peptide of the canine cathelicidin are shown in FIG. 1B. The canine cDNA molecule spans 630 by with short 5'- and 3'-untranslated regions, and is mainly occupied by a 519 bp-coding region. The cDNA encodes a predicted peptide of 172 amino acid residues. Computational predication with Signal IP and PSORT (ExPASy™, website au.expasy.org/tools/#proteome) indicates that a 29-amino acid signal peptide is located at its N-terminus.

Example 2

Tissue Expression of K9CATH

To determine mRNA expression of K9CATH, tissue samples were collected from clinically healthy dogs following procedures approved by the Kansas State University Institutional Animal Care and Use Committee. All samples were placed in liquid nitrogen immediately after collection and stored at −135° C. until use. All dogs had a thorough clinical examination and routine screening including hematology, blood chemistry, and urinalysis prior to tissue collection. All clinical laboratory results were within normal limits. Human bone marrow RNA was purchased from Clontech (Palo Alto, Calif.), and porcine bone marrow RNA was obtained (Wu et al., Infect. Immun., 68:5552 (2000)). Total RNA was extracted with TRI Regent (Sigma-Aldrich, St. Louis, Mo.) after grinding the frozen tissues in liquid nitrogen.

A one-step RT-PCR was used to detect expression of K9CATH mRNA [30]. Briefly, total RNA was treated with RQ1 RNase-free DNAse I (Promega) to remove any genomic DNA contamination. RNA samples (250 ng) were then used in a 25 µL RT-PCR reaction mixture with a 0.1 µM concentration of each sense and antisense primer (i.e. nested gene-specific primers used in RACE reactions). Conventional one-step RT-PCR was performed using an AccessQuick™ RT-PCR System kit (Promega). Complementary-DNA synthesis and pre-denaturation were performed for 1 cycle at 48° C. for 45 minutes and 95° C. for 3 minutes; amplification was carried out for 40 (K9CATH) or 25 (glyceraldehyde 3-phosphate dehydrogenase, GAPDH) cycles at 95° C. for 30 seconds, 55° C. for 30 seconds, and 72° C. for 30 seconds, with a final extension performed at 72° C. for 10 minutes in a 25 µL reaction mixture. After amplification, 10 µL of each reaction mixture was analyzed by 1.5% agarose gel electrophoresis, and the bands were visualized after ethidium bromide staining.

Thus, the expression of K9CATH mRNA in healthy canine tissues was evaluated by semi-quantitative RT-PCR analysis. As shown in FIG. 2, canine cathelicidin was predominately expressed in myeloid precursor cells (bone marrow), and to a lower extent in spleen, liver and testis. Minimal K9CATH expression was detected in healthy lung, kidney and intestinal tissues. The RT-PCR amplicons from bone marrow, spleen, liver, and testes were cloned into pGEM®-T Easy Vector, as described previously for RACE products, and sequenced. All amplified bands were confirmed to be the same cathelicidin molecule as in Example 1.

Example 3

Organization of the Canine CatheK9CATH Gene

The deduced amino acid sequence of K9CATH was used to search translated canine genomic sequences in the nonredundant (NR), high throughput genomic sequence (HTG), and whole genome shortgun sequence (WGS) databases in GenBank by using the TBLASTN program (Altschul et al., J. Mol. Biol., 215:403 (1990)) with default settings on the National Center for Biotechnology Information (NCBI) website (ncbi.nlm.nih.gov/BLAST). To derive the K9CATH gene structure, genomic sequences containing the canine gene were retrieved from GenBank and compared with its cDNA sequence by using the Spidey Program on the NCBI website (http://www.ncbi.nlm.nih.gov/IEB/Research/Ostell/Spidey). The chromosomal location of the K9CATH gene was revealed by using the Map Viewer Program (ncbi.nlm.nih.gov/BLAST).

Figure 4:
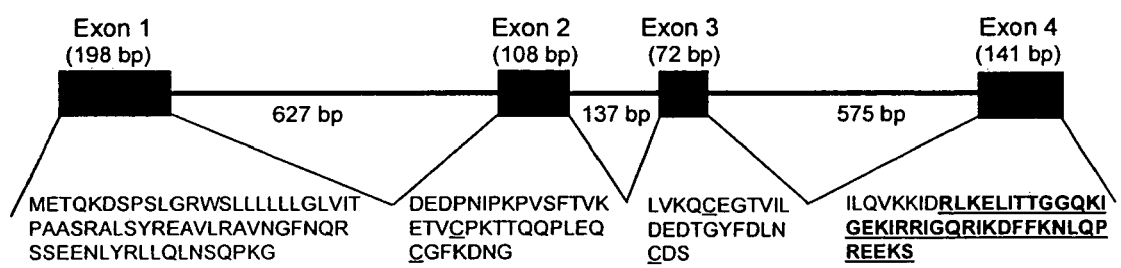
FIG. 4. Structural Organization of the Canine Cathelicidin gene. K9CATH is composed of four exons separated by three introns. The length of each exon and intron is indicated. The amino acid sequences encoded by each exon (SEQ ID NO: 43-46) are also shown. Four cysteines in the cathelin pro-region are underlined, and the mature peptide sequence is also underlined and in bold.

A search of the predicted K9CATH peptide sequence through all canine genome sequences currently available in GenBank identified two WGS sequences: AAEX02021310, which contained the entire K9CATH sequence and AACN010698115, which only included amino acid residues 67 through 126. The WGS sequence AAEX02021310 was therefore used for alignment with the full-length K9CATH cDNA sequence to obtain the gene structure using the Spidey Program. As shown in FIG. 4, the open reading frame for K9CATH was separated by three introns of 627, 137, and 575 bp, respectively, which is reminiscent of other mammalian cathelicidin genes (Niyonsaba et al., Curr. Drug Targets Inflamm. Allergy, 2:224 (2003); Niyonsaba et al., Immunology, 106:20 (2002); Gennaro et al., Biopolymers, 55:31 (2000)). The putative mature sequence is encoded by the last exon, while the first three exons encode the signal and pro-sequences. This gene organization is well conserved among all mammalian species investigated (Tomasinsig et al., Curr. Protein Pept. Sci., 6:23 (2005); Gennaro et al., Biopolymers, 55:31 (2000)). The K9CATH gene was located on chromosome 20 using the Map Viewer Program (ncbi.nlm.nih.gov/mapview). The length of each exon and intron is indicated in FIG. 4; amino acid sequences encoded by each exon are also shown. Four cysteines in the cathelin pro-region are underlined and the mature antimicrobial peptide sequence is underlined in bold. The nucleotide sequence of canine cathelicidin has been registered in the GenBank™ Database with accession number AY392089. It is noted that the exon-intron boundaries of cathelicidins are also highly conserved among mammalian species (data not shown).

Example 4

Synthesis of K9CATH Polypeptide

A peptide consisting of the C-terminal 38-amino acids of the mature K9CATH was chemically synthesized (BioMer Technology, Concord Calif.). The sequence of this peptide, designated SEQ ID NO: 4, is as follows: RLKELITTG-GQKIGEKIRRIGQRIKDFFKNLQPREEKS. The synthetic molecule eluted in a single peak on RP-HPLC and was confirmed by mass spectroscopy. Final purity of the peptide was >99% with a molecular weight of 4512.1. The peptide was lyophilized and dissolved in 0.01% acetic acid at 2 mg/mL (about 0.5 mM) as a stock solution and stored at −135° C. until use. Peptide concentration was determined by using the BCA protein assay kit (Pierce Inc., Rockford, Ill.). Sterile human serum albumin (Sigma Aldrich) was added to the peptide solution to achieve a final concentration of 0.1% prior to antimicrobial assays.

Example 5

Structural Analysis of K9CATH

Figure 5:
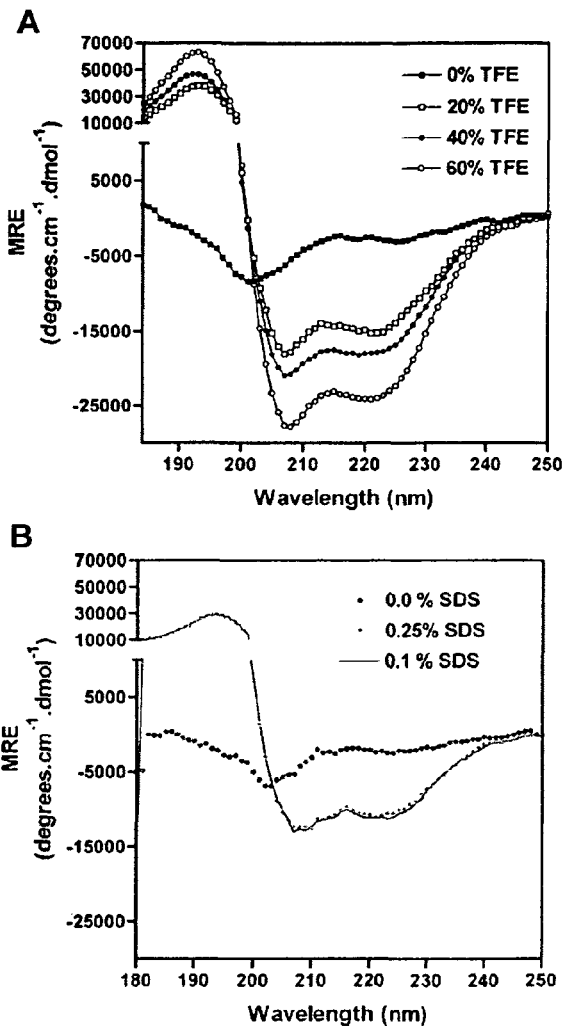
FIG. 5. Circular Dichroism Analysis—Effect of TFE (A) and SDS (B) on the secondary structure of Canine cathelicidin. Note that the peptide becomes highly α-helical in the presence of TFE or SDS.

To determine the secondary structure of K9CATH in membrane-mimetic environments, circular dichroism experiments were performed in a Jasco-715spectropolarimeter. Spectra were acquired using a 0.1 cm path-length cell over the 190-250 nm range Soulages et al., J. Biol. Chem., 276:34162 (2001)). Spectra were collected at 25° C. every 1nm with a 2 second averaging time per point and a 1 nm band pass. The peptide was measured in 50 mM potassium phosphate buffer with different concentrations of trifluoroethanol (TFE) (10%, 20%, 40%, and 60%) or SDS micelles (0.25% and 0.5%) as well as without TFE. Mean residue ellipticity (MRE) was expressed as $[\theta]_{MRE}$ (deg.cm$^2$.dmol$^{-1}$). The α-helix content was estimated from the dichroic minimum at 222 nm (Chen et al., Biochemistry, 13:3350 (1974)). CD spectroscopy measurements revealed that K9CATH adopted a completely random coiled conformation without any α-helical structure in aqueous solution. The peptide, however, showed enhancement of helical conformation with increasing concentrations of the helix-inducing agent TFE, exhibiting 72% helicity in 60% TFE (FIG. 5). Similarly, in a lipid-mimicking environment, K9CATH adopted a structure with a 30% helical content in the presence of 0.1% SDS.

Structural models also were generated for the cathelicidin peptide via homology modeling. The target structure was predicted via alignment to an NMR solution structure of CAP18 (Chen et al., FEBS Lett., 370:46 (1995). Initial sequence alignment for these two systems was performed via the Clustal-W program (Thompson et al., Nucleic Acids Res., 22:4673 (1994)), using the Blosum 30 substitution matrix, with a gap-opening penalty of 10 and a gap-extension penalty of 0.1. The resulting alignment and corresponding three-dimensional CAP18 peptide structure were then processed via the Modeller program (Sanchez et al., Meth. Mol. Biol., 143:97 (2000) to yield a structural prediction for the cathelicidin target. Modeller's default simulated annealing cycles were used for structural refinement. Analysis of the peptide secondary structure and surface characteristics was carried out on the resulting structures via SYBYL (SYBYL®6.9.2, TRIPOS Inc., St. Louis, Mo.), and the secondary structure prediction was validated using the PSIPRED program (McGuffin et al., Bioinformatics, 16:404 (2000)).

Figure 6:
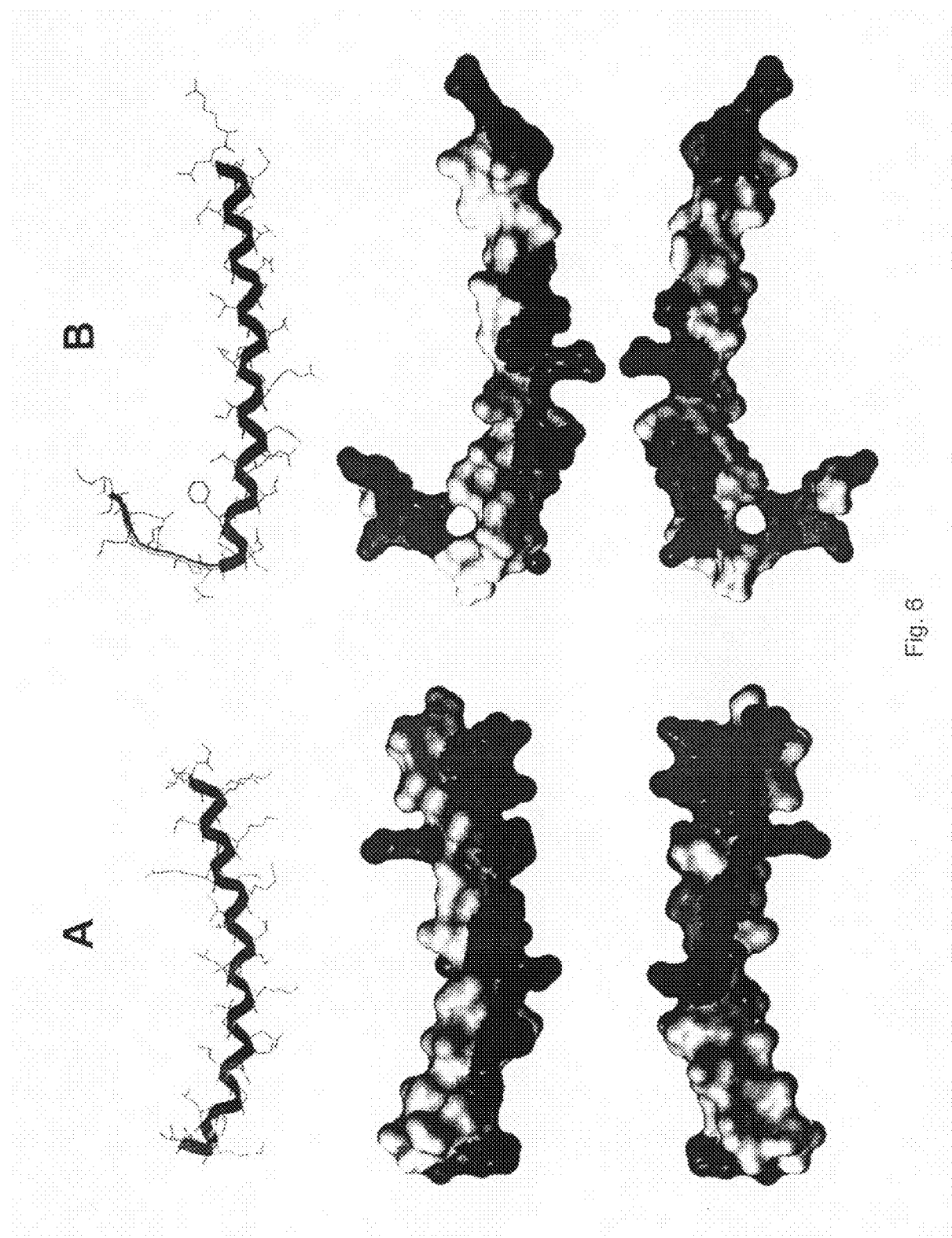
FIG. 6. Three Dimensional Structure Assignment and Surface Analysis for K9CATH. The leftmost column depicts ribbon diagrams showing α-helix (purple), and coil (cyan) secondary structure elements for the four peptides (no β-sheet elements are present). The two rightmost columns depict front and back views of peptide solvent accessible surfaces. Acidic (anionic) residues are colored red, basic (cationic) are colored blue, and hydrophobic are yellow.

The structure of K9CATH was predicted through alignment with a NMR solution structure of Cap18 (PDB ID: 1lyp). The key motifs are preserved in the sequence alignment of the rabbit and K9CATH structures, particularly towards the central portion of the observed α-helix in the rabbit sequence (FIG. 6A). This provides reasonable confidence that much of the canine structure should adopt a similar helical structure (FIG. 6B), approximating that shown in FIG. 6A top panel. A comparison of rabbit and canine surface models is shown through a three-dimensional representation in FIGS. 6 A and B. It was also noted that within the aligned helical portions of the rabbit and canine cathelicidins, there is a substantial difference in the net electrostatic profiles: the rabbit structure has 13 basic residues and only one acid (net charge of +12 at pH=7), whereas the canine peptide has nine basic residues and three acids (net charge of only +6). This distinction could lead to appreciable differences in environmental preferences and potential intermolecular associations of these two cathelicidins. Finally, for the canine cathelicidin structure represented in FIGS. 6 A and B, one observes that the 7 C-terminal residues (QPREEKS) not present in the observed rabbit model do not retain the hydrophobic/polar oscillation pattern, but rather are collectively very polar. Taken together, K9CATH showed features common to a variety of antimicrobial peptides such as a positive charge at a neutral pH and a α-helical structure.

In sum, structural analysis of K9CATH was performed using circular dichroism (CD) and computational 3-dimensional structural analysis. The folding of K9CATH assumes a α-helical conformation, which is the most common spatial arrangement among natural antimicrobial peptides (Gennaro et al., Biopolymers, 55:31 (2000)), including the cathelicidin peptides. Supporting this contention is the characteristic oscillation between hydrophobic and polar residues with a frequency commensurate with the 10/3 α-helical twist. As shown in the three dimensional representation depicted in FIG. 6, this oscillation leads to formation of juxtaposed hydrophobic and polar sides of the helix: a structural feature that suggests that lipophilic/hydrophobic interactions may drive these peptides to either aggregate with similar molecules or at a membrane surface, using their hydrophobic sides for intermolecular binding and facing their polar sides outwards for favorable solvent interactions. Preliminary analysis suggests that K9CATH would be more amenable to such behavior by virtue of a hydrophobic surface that is more pure and continuous than that of the rabbit. It is possible, however, that the one residue which most obviously disrupts hydrophobic continuity in the rabbit cathelicidin (i.e., the lysine in position 14) may instead actually participate in an associative intermolecular salt bridge, that is not available to the canine cathelicidin. A unique structural feature of K9CATH is the presence of seven extra amino acid residues located in the C-terminal. Because these amino acids are collectively very polar, there is no obvious evidence to suggest that these residues should perpetuate the helical structure present in the first 31 residues of the structure; it is more reasonable to assume that the C-terminus will be solvent exposed and likely somewhat disordered (FIG. 6B). Previous CD studies have shown that the helical content of α-helical cathelicidin peptides ranges from 30-90%, depending on the microenvironment (e.g., the presence of a helix-inducing agent) and the origin of the peptide [12]. Similarly, the present CD studies showed a α-helical content of K9CATH ranging from 42% to 72% in the presence of 20% and 60% TFE respectively. In addition, in an environment approximating a physiological state (i.e., lipid-mimicking), the α-helical content of K9CATH was lower, yet still within the range of that reported from other mammalian cathelicidins. Combining the results from the three-dimensional structural analysis and the CD studies it can thus be concluded that K9CATH possesses an inducible α-helical structure. Since most linear cathelicidins are predominantly α-helical in nature, this suggests that the broad antimicrobial spectrum of these peptides is directly related to the α-helical structure, which may facilitate these endogenous antimicrobial peptides' interaction with bacterial membranes, thus resulting in rapid elimination of pathogenic microorganisms (Zanetti, J. Leukoc. Biol., 75:39 (2004); Gennaro et al., Biopolymers, 55:31 (2000); Zanetti et al., Curr. Pharm. Des., 8:779 (2002); Ramanathan et al., Microbes Infect., 4:361 (2002); Oren et al., Biopolymers, 47:451 (1998)).

Example 6

K9CATH Antimicrobial Activity

Antimicrobial activity of K9CATH against a broad spectrum of microorganisms was evaluated. The K9CATH peptide used for the antimicrobial assays represents the predicted amino acid sequence from the entire mature peptide encoded by the exon 4 region (the cleavage site in the human cathelicidin was used to predict the cleavage site of the canine cathelicidin).

Microorganisms evaluated were: *Candida albicans* ATCC 11006 and 14053, *Escherichia coli* ATCC 25922, 700336, 700378, and BAA-457, *Klebsiella pneumoniae* ATCC 10031, *Listeria monocytogenes* ATCC 19155, *Proteus mirabilis* ATCC 12453, *Pseudomonas aeruginosa* ATCC 10145, *Salmonella Enteritidis* ATCC 13076, *Salmonella Typhimurium* ATCC 13311, *Staphylococcus aureus* ATCC 10832, *Ureaplasma canigenitalium* ATCC 51252, and *Ureaplasma urealyticum* ATCC 27619. *C. albicans* was grown overnight (35° C.) on potato dextrose agar and managed according to NCCSL standards (Pfaller et al., Manual NCCLS #M27-A2, 6th ed., Wayne, Pa. (2002)). U. canigenitalium and U urealyticum were stored at −20° C. in urea broth 10B (per ATCC specifications) and thawed at 5° C. the night prior to assay. All other bacteria were maintained on trypticase soy agar (Difco, Detroit, Mich.) plates at 37° C. Mid-logarithmic phase bacteria were grown by transferring single cell colonies into trypticase soy broth (Difco), followed by incubation and homogenization for 3 hours at 37° C. Bacterial pellets were obtained after centrifugation for 10 minutes at 4° C. at 900×g, and washed once, followed by suspension in 10 mM sodium phosphate buffer (PB, pH 7.4, [Na+]=17.83 mM). Initial bacterial concentrations were determined (Ferraro et al., Manual NCCLS #M7-A6, 6th ed., Wayne, Pa. (2003)). Initial bacterial populations of $10^8$ CFU/mL were obtained at an optical density (OD) of 0.1 at 600 nm. *C. albicans* were suspended in 10 mM PB to a McFarland standard of 0.5 for an initial $10^8$ CFU/ml following NCCLS standards (Pfaller et al., Manual NCCLS #M27-A2, 6th ed., Wayne, Pa. (2002)), except that the recommended 0.85% saline solution was replaced with 10 mM PB. All microbial serial dilutions were performed in 10 mM PB to obtain $10^3$ CFU/mL working dilutions.

A modified broth microdilution method (Pfaller et al., Manual NCCLS #M27-A2, 6th ed., Wayne, Pa. (2002); Ferraro et al., Manual NCCLS #M7-A6, 6th ed., Wayne, Pa. (2003)) was used to determine the antimicrobial activity of K9CATH (Sang et al., Infect. Immun., 73:2611 (2005)). Briefly, 50 µL of the K9CATH working stocks were added to the wells of a microtiter plate in which 25 µL of 30 mM sodium PB (pH 7.4, [Na+]=53.49 mM), 25 µL $H_2O$, and 50 µL of the microbial suspension had been previously combined. Microtiter plates were incubated at 37° C. for 2 hours in a shaking incubator (100 RPM), followed by the addition of 150 µL of the corresponding nutritive broth. Antimicrobial activity was determined by establishing the minimal inhibitory concentrations (MIC), defined as the lowest concentration in which microbial growth was prevented, as indicated by the lack of turbidity or color change in the medium (urea broth 10B) after 24 hours of incubation at 37° C. Treated gonorrheal suspension (50 µL) was spot-plated on chocolate agar, and the MIC was defined as the lowest concentration in which no colonies developed after 24 hours of incubation at 37° C. in 5% $CO_2$. This was done because *N. gonorrhoeae* does not show turbidity as evidence of growth in GC broth and also because of its high autolytic activity in liquid medium. To determine the effect of salt on K9CATH antimicrobial activity, two representative bacteria were used, including the Gram negative *E coli* ATCC 25922 and the Gram positive *L. monocytogenes* ATCC 19115. The final sodium concentration of the bactericidal mixture was adjusted to 15, 30, 50, 140, and 300 mM with NaCl. In addition, the effect of lipopolysaccharides (*E. coli* 0111:B4 LPS; Sigma) on the K9CATH anti *E. coli* activity was evaluated at 0.01, 0.1, 1, and 10 µg/mL. The effect of fetal bovine serum (FBS) at 10, 20, 30, 40, 50, and 75% was assessed at 140 mM NaCl. All assays were performed in triplicate.

Thus, to determine the antimicrobial activity of K9CATH, a 38 amino acid peptide corresponding to the full-length mature predicted amino acid sequence was chemically synthesized and used for all antimicrobial assays. K9CATH effectively killed Gram-positive and Gram-negative bacteria, yeast, and *Ureaplasma* spp. Its broad antimicrobial activity was comparable to that reported for other synthetic or natural cathelicidin peptides (Bals et al., Proc. Natl. Acad. Sci. USA, 95; 9541 (1998); Skerlavaj et al., J. Biol. Chem., 271:28375 (1996); Yu et al., J. Pept. Res., 60:1 (2002); Murakami et al., J. Immunol., 172:3070 (2004); Shin et al., Biochem. Biophys. Res. Commun., 285:1046 (2001)) (Table 4).

TABLE 4

Antimicrobial Activity of K9CATH

| Microorganism | ATCC | MIC (µM) |
| --- | --- | --- |
| *Candida albicans* | 11006 | 44.33 |
| *Candida albicans* (hematogenous) | 14053 | 11.08 |
| *Escherichia coli* | 25922 | 1.11 |
| *Escherichia coli* | 700336 | 1.11 |
| *Escherichia coli* | 700378 | 1.11 |
| *Escherichia coli* | BAA-457 | 1.11 |
| *Klebsiella pneumoniae* | 10031 | 1.11 |
| *Proteus mirabilis* | 12453 | 1.11 |
| *Pseudomonas aeruginosa* | 10145 | 1.11 |
| *Salmonella Enteritidis* | 13076 | 0.44 |
| *Salmonella Typhimurium* | 13311 | 1.11 |
| *Neisseria gonorrhoeae* | 10150 | 0.06 |
| *Staphylococcus aureus* | 10832 | 44.33 |
| *Listeria monocytogenes* | 19115 | 0.44 |
| *Ureaplasma canigenitalium* | 51252 | 0.06 |
| *Ureaplasma urealyticum* | 27619 | 44.33 |

The MIC was determined with a broth microdilution method adapted from NCCLS

The MIC of K9CATH for C. albicans was higher than those reported for bovine and ovine cathelicidins, BMAP-27 and SMAP-29 [16,49] respectively, and less than that reported for human LL-37 (Gennaro et al., Biopolymers, 55:31 (2000); Murakami et al., J. Immunol., 172:3070 (2004)). Likewise, synthetic canine cathelicidin was more effective in killing *C. albicans* isolated from hematogenous origin compared to isolate from the vaginal epithelium, strongly suggesting that K9CATH exerts its broad antimicrobial effects at a systemic level. Interestingly, the two sexually transmitted disease bacteria *N. gonorrhoeae* and *Ureaplasma canigenitalium* were killed with the lowest concentration documented of any antimicrobial peptide reported to date (0.0625 μM), including the recently identified testisderived β-defensins in dogs (Sang et al., Infect. Immun., 73:2611 (2005)). *Salmonella typhimurium* and *enteritidis* (bacteria commonly implicated in cases of food-poisoning) were also effectively killed by K9CATH. In this regard, the antimicrobial activity of K9CATH was in agreement to that of its mammalian congeners (Gennaro et al., Biopolymers, 55:31 (2000); Skerlavaj et al., J. Biol. Chem., 271:28375 (1996); Yu et al., J. Pept. Res., 60:1 (2002); Shin et al., Biochem. Biophys. Res. Commun., 285:1046 (2001)). The sensitivity of *P. aeruginosa* to K9CATH was comparable to murine (Yu et al., J. Pept. Res., 60:1 (2002)), bovine (Skerlavaj et al., J. Biol. Chem., 271:28375 (1996)), and ovine (Shin et al., Biochem. Biophys. Res. Commun., 285:1046 (2001)) cathelicidins, but threefold more active than that of the human LL-37.

Conversely, *S. aureus*, an important epidermal pathogen, was inhibited at a higher concentration (50 μM) which suggests that K9CATH antimicrobial activity focuses on the systemic level and to a lesser extent at the surface of the skin. Nevertheless, human cathelicidin (LL-37) inhibited skin *S. aureus* at a comparable concentration (>64 μM) (Murakami et al., J. Immunol., 172:3070(2004); Murakami et al., J. Dent. Res, 81:845 (2002)).

Figure 7:
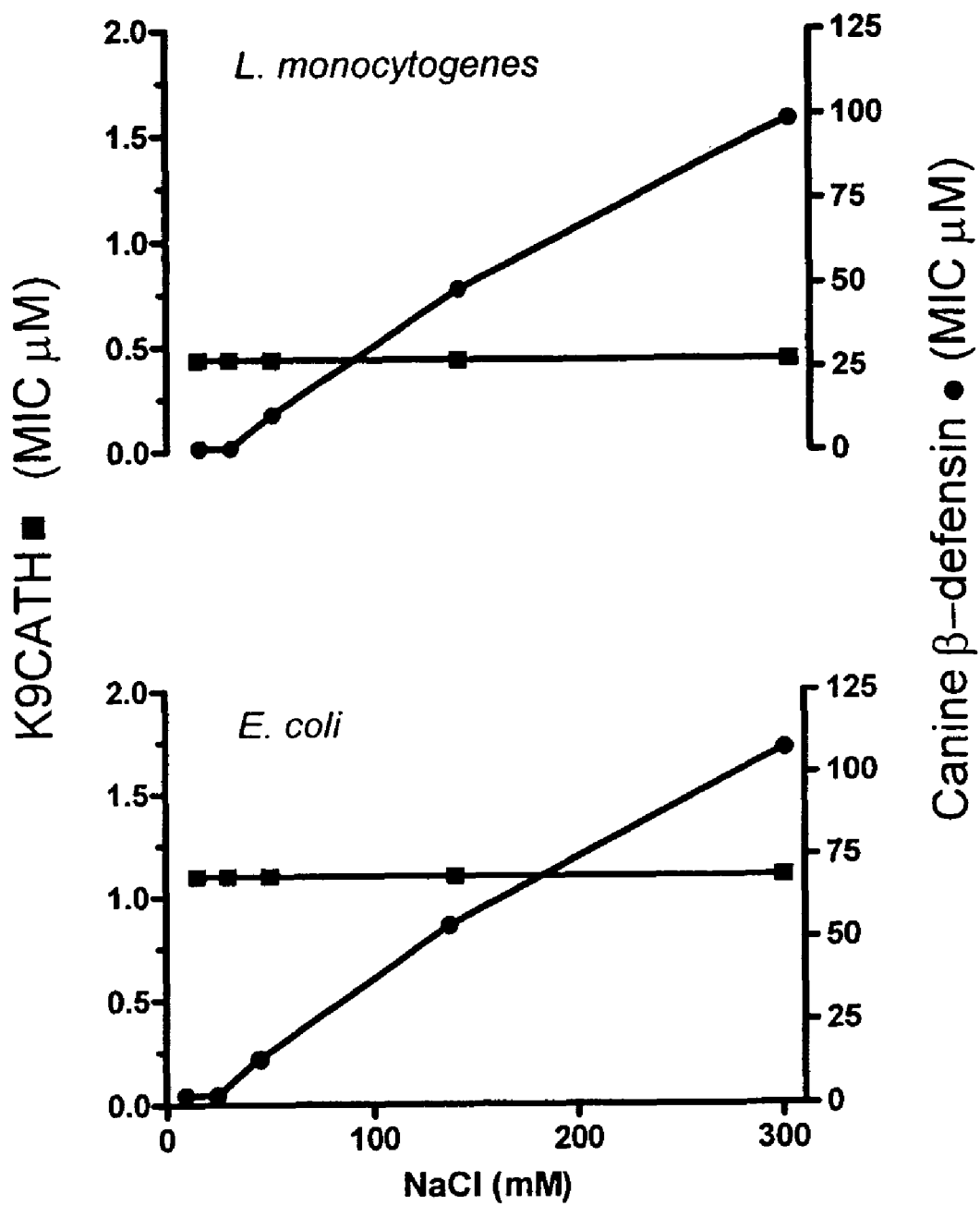
FIG. 7. Effect of Sodium Chloride on Antimicrobial Activity of K9CATH. A broth microdilution method was used to determine the MIC of cBD against two strains of bacteria, Gram-negative E. coli (ATCC 25922) and Gram-positive L. monocytogenes (ATCC 19115), in various salt concentrations. The final sodium concentration of the bactericidal mixture was adjusted to 15, 30, 50, 140, and 300 mM with NaCl. Canine β-defensin, a salt-sensitive antimicrobial peptide, was used for comparison. All assays were performed in triplicate.

The bactericidal activity of K9CATH was independent of the salt concentration (15 to 300 μM) of the microenvironment used in the in vitro assay against *E. coli* and *L. monocytogenes* (FIG. 7). This finding contrasts the reported salt-sensitive activities of cathelicidins from human (LL-37) and cow (BMAP-27) (Gennaro et al., Biopolymers, 55:31 (2000); Skerlavaj et al., J. Biol. Chem., 271:28375 (1996); Yu et al., J. Pept. Res., 60:1 (2002); Murakami et al., J. Immunol., 172: 3070 (2004)). Furthermore, the present data showed that serum (fetal bovine serum) diminishes 20 to 150 fold the K9CATH activity against *E. Coli* over a range of 5 to 75% FBS (Table 5).

TABLE 5

Susceptibility of *E. coli* to K9CATH Under Different Serum Concentration

| FBS[a] (%) | MIC[b] (μM) *E. coli* ATCC 25922 |
|---|---|
| 0 | 1.25 |
| 5 | 12.5 |
| 10 | 12.5 |
| 20 | 50 |
| 30 | 200 |
| 50 | 200 |
| 75 | 200 |

[a] Fetal bovine serum
[b] MIC: Minimal inhibitory concentration: lowest concentration in which the microorganism growth was prevented LPS did not affect the anti *E. coli* activity at a lower concentration (0.01 μg/mL), but the MIC increased 60-fold when LPS was used in a range from 0.1 to 10 μg/mL (Table 6).

TABLE 6

Susceptibility of *E. coli* to K9CATH Under the Influence of LPS[a]

| LPS[a] (μg/ml) | MIC[b] (μM) *E. coli* ATCC 25922 |
|---|---|
| 0 | 1.25 |
| 0.01 | 1.25 |
| 0.1 | 75 |
| 1 | 75 |
| 10 | 75 |

[a] LPS: Lipopolisaccharides from *E. coli* O111:B84
[b] MIC: Minimal inhibitory concentration: lowest concentration in which the microorganism growth was prevented Example 7

LPS Binding Assay

Binding of LPS to K9CATH was measured by the kinetic chromogenic *Limulus* amoebocyte lysate (LAL) assay (Kinetic-QCL 1000 kit; BioWhittaker, Walkersville, Md.) (Turner et al., Antimicrob. Agents Chemother., 42:2206 (1998); Tack et al., Eur. J. Biochem., 269:1181 (2002)). Briefly, 25 μL of serially diluted peptide was added in duplicate to 25 μL of *E. coli* O111:B4 lipopolysaccharide (LPS) containing 0.5 endotoxin units/mL, and incubated for 30 minutes at 37° C. Following addition of 50 μL of the amoebocyte lysate reagent and 100 μL of the chromogenic substrate, Ac-Ile-Glu-Ala-Arg-p-nitroanilide, optical density at 405 nm was measured at 10 and 16 minutes with a microplate reader (Model Elx800, Bio-Tek, Winooski, Vt.) following incubation. Percent LPS binding was calculated as ([$\Delta D1-(\Delta D2-\Delta D3)$]/$\Delta D1$)×100, where $\Delta D1$ represents the difference in the optical density between 10 and 16 min for the sample containing LPS only, $\Delta D2$ represents the difference in the optical density between 10 and 16 minutes for the samples containing LPS and different concentrations of K9CATH, and $\Delta D3$ represents the difference in the optical density between 10 and 16 minutes for the samples containing different concentrations of peptide with no LPS. Hill plots were performed (Turner et al., Antimicrob. Agents Chemother., 42:2206 (1998); Tack et al., Eur. J. Biochem., 269:1181 (2002)) by plotting $\log_{10}$ K9CATH concentration against $\log_{10}$ [$F_1/(1.0-F_1)$], where $F_1$ was the fractional inhibition of LPS binding activity.

Figure 8:
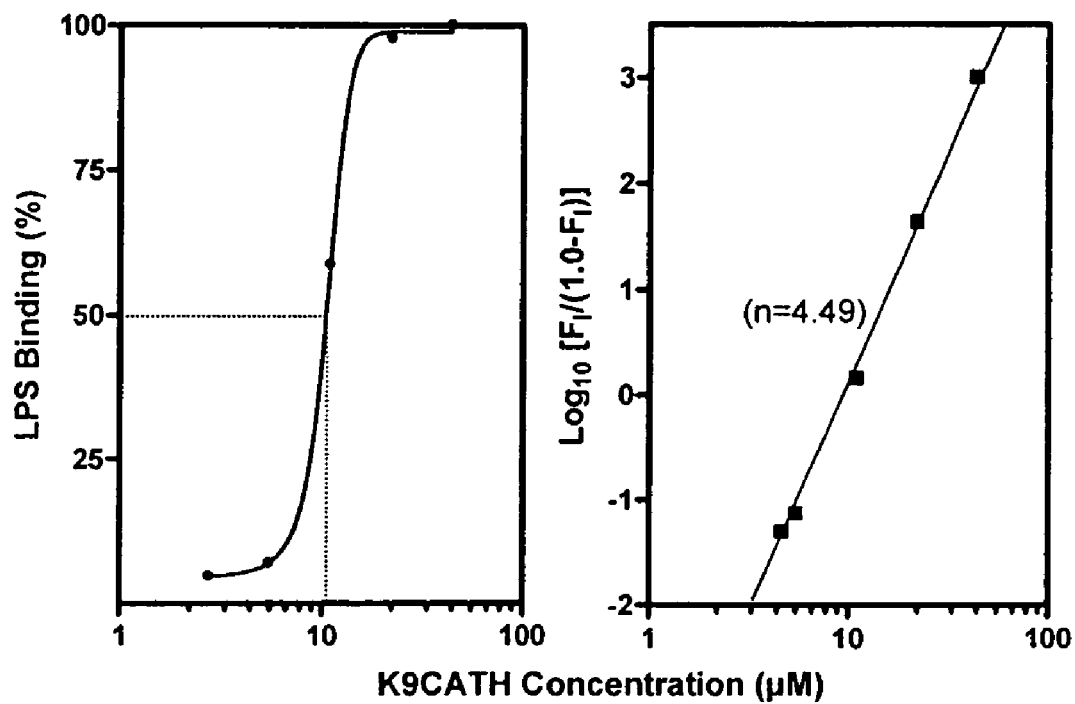
FIG. 8. Binding of LPS by Canine Cathelicidin. The assays were performed by using a quantitative chromogenic Limulus amoebocyte lysate (LALA) assay kit (QCL-1000 kit, Bio-Whittaker, Walkersville, Md., USA) as previously described (47). Right panel—The data was graphed also on a Hill plot which showed a coefficient of 4.49. The data represent the mean of duplicate values from two independent experiments.

Results indicate that K9CATH was capable of binding LPS with 50% binding occurring at approximately 10.6 μM (FIG. 8, left panel). The typical sigmoidal shape of the canine cathelicidin binding isotherm indicates cooperativity. When the data were graphed on a Hill plot, which showed a coefficient of 4.49 (FIG. 8, right panel), binding of LPS to K9CATH is highly supportive. This characteristic has also been found in a few other cathelicidins, such as human LL-37/hCAP-18 (Turner et al., Antimicrob. Agents Chemother., 42:2206 (1998)) and sheep SMAP-29 (Tack et al., Eur. J. Biochem., 269:1181 (2002)).

Example 8

K9CATH Hemolytic Activity

Hemolytic activity of K9CATH was determined (Skerlavag, FEBS Lett., 463:58 (1999); Yu et al., J. Pept. Res., 60:1 (2002)). Briefly, 4 mL of canine blood was collected in EDTA-containing blood collection tubes (Becton Dickinson, Franklin Lakes, N.J.). Whole blood was then centrifuged at 10,000×g for 1 minute at room temperature. Plasma was discarded (supernatant) and erythrocytes were washed twice with PBS, re-suspended to a 0.5% (vol/vol) solution in PBS, and 90 μL dispensed into 96-well microtiter plates. Different concentrations of K9CATH dissolved in 0.01% acetic acid were added in duplicate to dog cells and incubated at 37° C. for 2 hours. Following centrifugation at 8000×g for 10 minutes, supernatants were transferred to new 96-well microtiter plates and monitored by measuring the absorbance at 405 nm for released hemoglobin. Controls for 0 and 100% hemolysis consisted of cells suspended in PBS only and in 1.0% Triton X-100, respectively. Percentage of hemolysis (%) was calculated as $[(OD_{415\ nm,\ peptide\ solution} - OD_{415\ nm,\ PBS\ only})/(OD_{415\ nm,\ 1\%\ Triton\ X-100} - OD\ 415\ nm,\ PBS\ only)] \times 100$. The N-terminal 18 amino acid segment of bovine myeloid antimicrobial peptide 28 (BMAP-$28_{(1-18)}$) (Skerlavaj et al., J. Biol. Chem., 271:28375 (1996); Yu et al., J. Pept. Res., 60:1 (2002); Risso et al., Cell. Immunol., 189:107 (1998)) was used as a positive control. To evaluate the in vitro hemolytic activity of K9CATH across species, red blood cells from chicken and humans were treated with K9CATH following the same protocol listed above.

Figure 9:
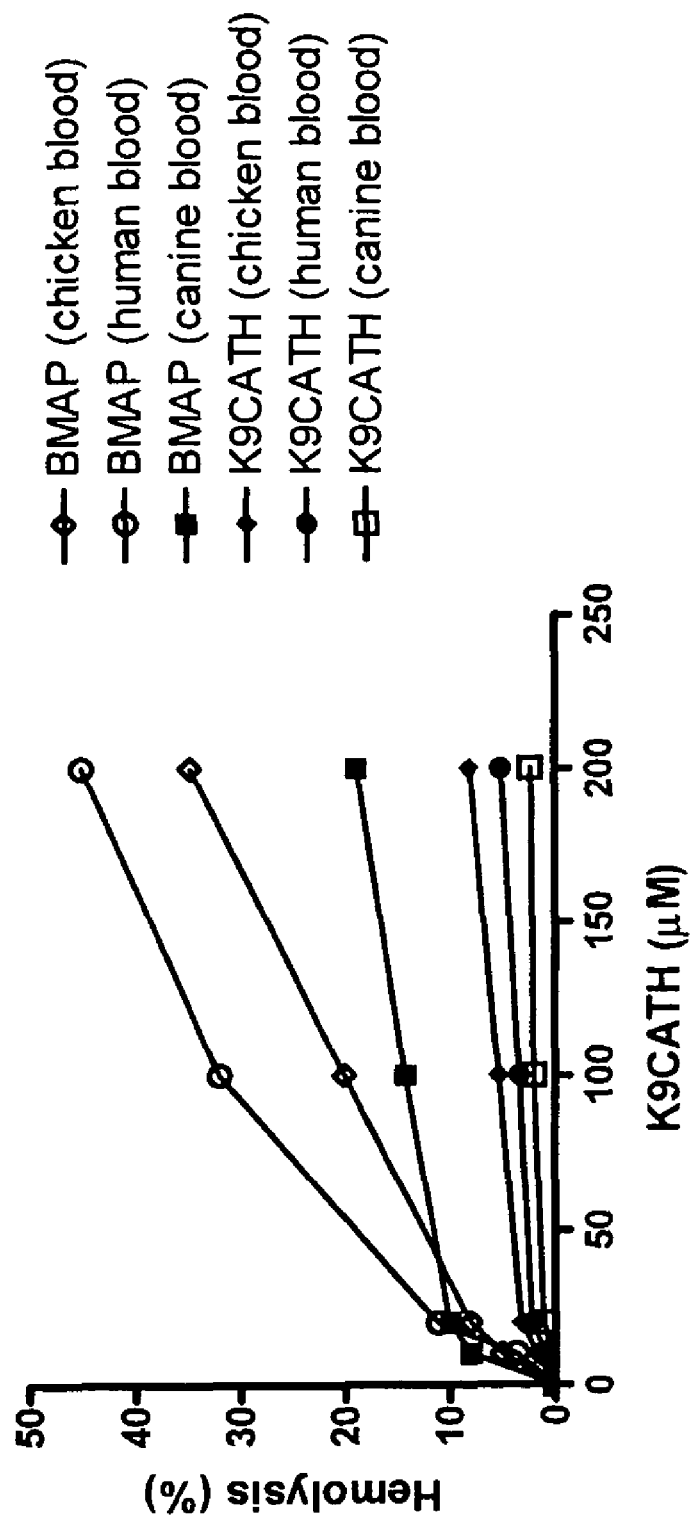
FIG. 9. Hemolytic Activity of Canine Cathelicidin. The assays were performed with chicken red blood cells as previously described (49). The data shown represent the mean of duplicate values from two independent experiments.

The hemolytic activity of K9CATH was determined using dog, human, and chicken erythrocytes. As shown in FIG. 9, K9CATH displayed a negligible hemolytic activity, lysing <5% of erythrocytes at 100 μM in these three species. BMAP-$28_(1-18)$ (i.e. the N-terminal peptide of bovine cathelicidin BMAP-28) was used as a control and hemolyzed approximately 20%, 25% and 30% of chicken, dog, and human erythrocytes at 100 μM respectively, which is consistent with previous reports (Skerlavaj et al., J. Biol. Chem., 271:28375 (1996)). K9CATH exhibited a 10-20 fold lower in vitro hemolytic activity against dog and chicken erythrocytes when compared to BMAP-18.

Example 9

Alignment of K9CATH with Other Cathelicidins

Figure 3:
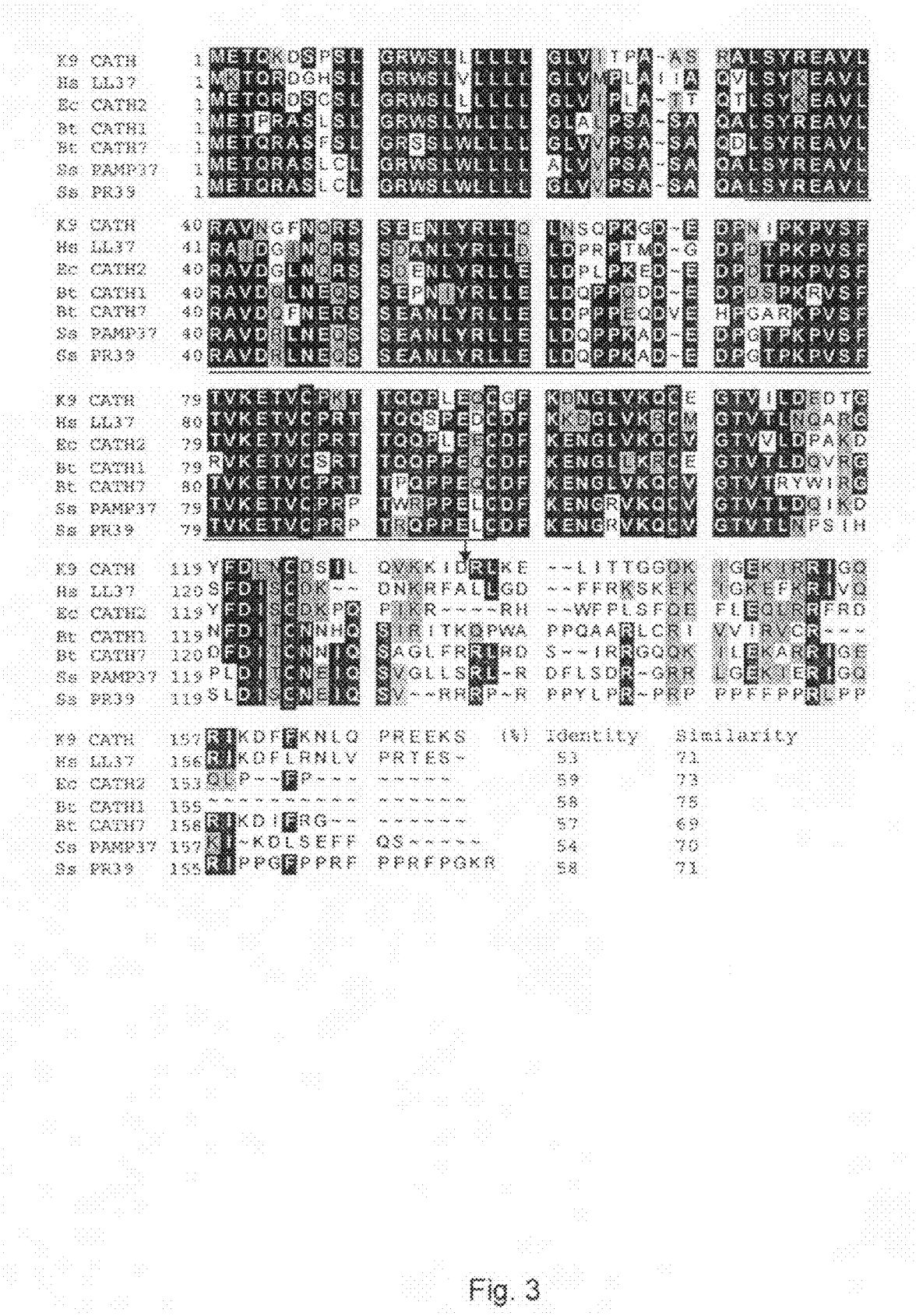

Using CLUSTAL-W, the predicted amino acid sequence of K9CATH was aligned to six mammalian cathelicidins from different species with a highly conserved preproregion (FIG. 3).

Canine cathelicidin, K9CATH, has a signal peptide, a cathelin domain, and a mature peptide of 29, 103, and 38 amino acid residues, respectively. K9CATH also has preserved the presence and identical position of four cysteines embedded within the proregion sequence, which is a highly conserved characteristic of the cathelicidin peptide family. This four-cysteine classical motif is thought to stabilize to the cathelin domain by the two disulfide bonds between the cysteine residues C85-C96 and C107-C124 (see FIG. 3).

Canine cathelicidin displayed a similarity of >80% when compared to the N-terminal cathelin-domain region of all listed cathelicidins. In addition, the overall similarity among these mammalian cathelicidins was approximately 70%; however, the antimicrobial C-terminal mature peptide region of all listed cathelicidins displayed a highly variable sequence. The putative mature peptide of K9CATH (SEQ ID NO: 4) shows the greatest similarity to human LL-37 (SEQ ID NO: 33) at 46%, and a much lower (<10%) identity to those of other species (SEQ ID NO: 33-38). Unlike porcine PR-39 (SEQ ID NO: 38) or bovine CATH2 (SEQ ID NO: 34), which are antimicrobial peptides rich in proline, K9CATH possesses only one proline in its antimicrobial sequence (Pestonjamasp et al., Peptides, 22:1643 (2001); Castiglioni et al., Cytogenet. Cell Genet., 75:240 (1996); Zhang et al., Vet. Res., 31:277 (2000)).

Example 10

Phylogenetic Analysis

Figure 10:
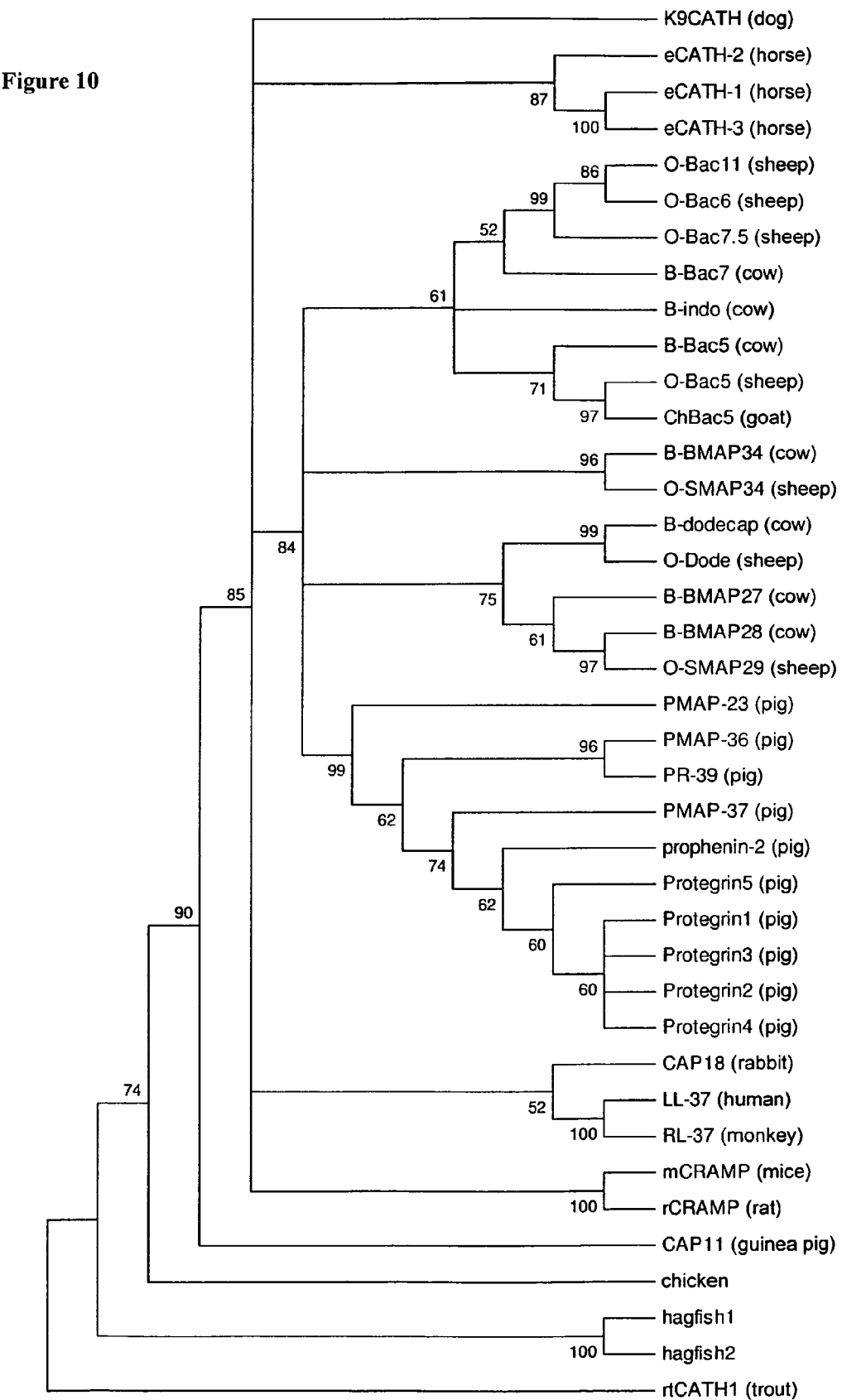
FIG. 10. Molecular Phylogeny of Cathelicidins. Bootstrap values are indicated on the branches. Only topology is displayed. Note that K9CATH is separated from all other mammalian sequences. MEGA version 3.1 software (The Pennsylvania State University, University Park, Pa.) was used for analysis.

A neighbor-joining condensed tree (FIG. 10) was constructed from Poisson correction distances of preproregion cDNA sequences obtained from 39 reported cathelicidins. Branches of low significance (Bootstrap values from 1000 replicates less than 50%) were eliminated to form the multifurcating condensed tree. MEGA (version 3.1, The Pennsylvania State University, University Park, Pa.) was used in the study.

A condensed multifurcating tree was generated that emphasized the reliable portion of pattern branches without considering the exact distance between each peptide. The branch lengths of the condensed tree are not proportional to the number of nucleotide or amino acids substitutions as the present analysis was based on topology. In this fashion, the phylogenetic reconstruction placed K9CATH in a distinct gene cluster separated from all other mammalian sequences. Because K9CATH appears to be a single cathelicidin gene, it can be suggested that dogs belong to the monocathelicidin species where there have not been duplication of this ancestral gene in the evolutionary history of these carnivores. All monocathelicidin species studied thus far, express the single cathelicidin gene as an α-helix (Taomasinsig et al., Curr. Protein Pept. Sci., 6:23 (2005)).

Example 11

Effect of K9CATH on *Trichomonas*

*Trichomonas vaginalis* strain T1 (clinical isolate reported by Tai in 1993, was grown in TYM medium supplemented with 10% heat inactivated horse serum, 10 U penicillin, 10 μg streptomycin, 180 μM ferrous ammonium sulfate and 28 μM sulfosalicylic acid. Parasites were passaged daily (about 1×10⁶ parasites into 10 mL TYM medium).

Figure 11:
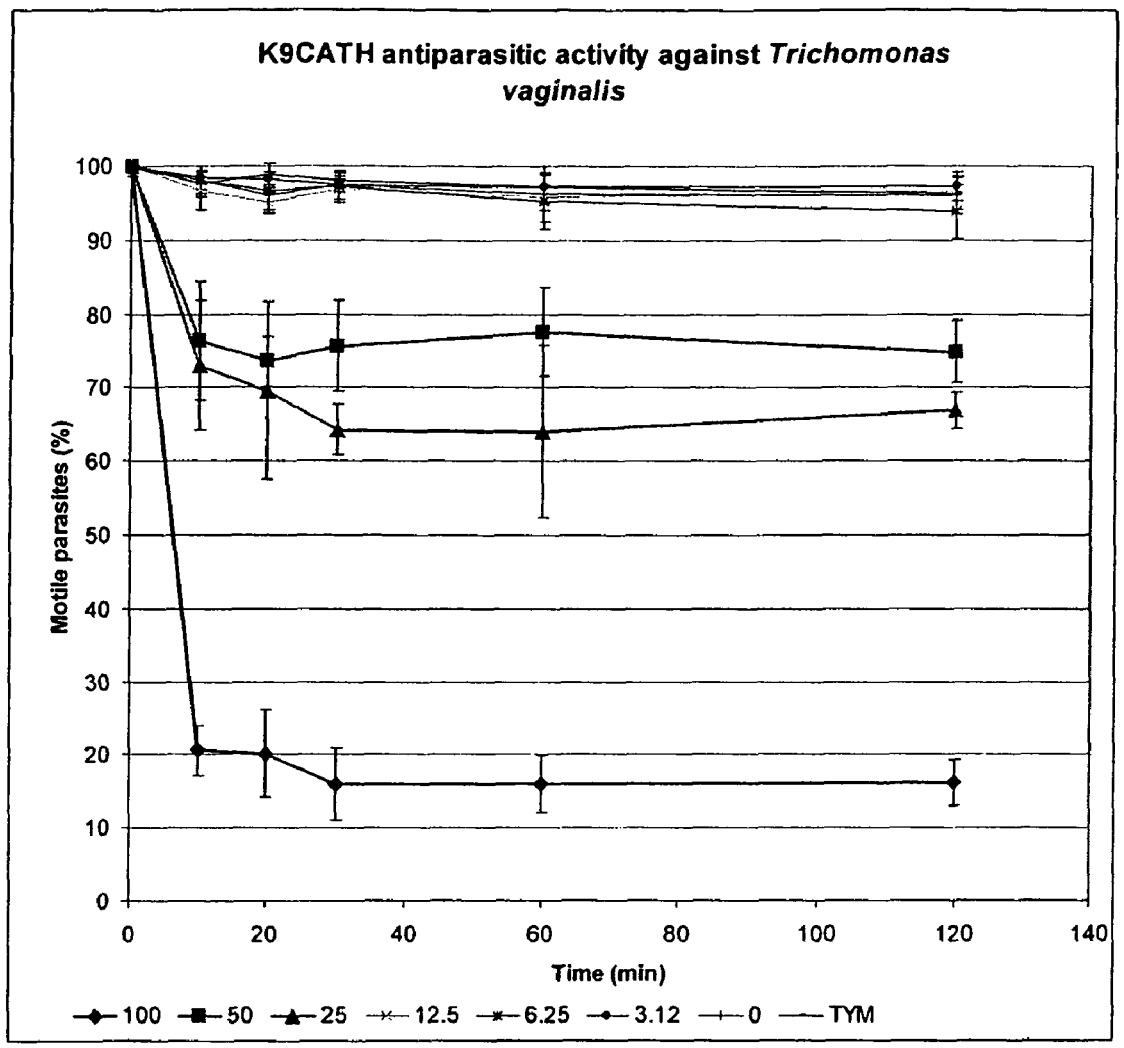
FIG. 11. Antiparasitic effect of K9CATH. The antiparasitic effect of K9CATH is stable over time. There is an inverse relationship between K9CATH concentration and parasite motility (lower motility is indicative of higher parasite mortality) indicating that antiparasitic effect is concentration dependent. At 100 µM K9CATH, the highest concentration tested, about 80% of the parasite cultures were killed (shown on figure as 20% motile parasites).

Treatment of the parasites with canine cathelicidin (K9CATH) resulted in an immediate, as well as stable effect on parasite motility and viability (FIG. 11). At the highest concentration tested (100 μM K9CATH), about 80% of the parasite cultures were killed. K9CATH at 50 μM and 25 μM had a modest effect on parasite viability, while K9CATH at 12.5 μM or lower had negligible effect on parasite viability.

Example 12

Summary

K9CATH effectively kills bacteria responsible for STDs with the highest potency reported for any natural or synthetic antimicrobial peptide, including all protegrin analogs studied to date (Ostberg et al., Peptides, 26:197 (2005)). STDs of bacterial origin have been documented only sporadically in dogs, and connection between reported pathogens and clinical disease remains controversial (Carmichael et al., Cornell Vet., 78:63 (1988); Doig et al., Can. J. Comp. Med., 45:233 (1981); Harasawa et al., Int. J. Syst. Bacteriol., 43:640 (1993)). These findings clearly show a superior antimicrobial capability of the newly identified K9CATH against common pathogens of STDs in humans. *N. gonorrhoeae* downregulates expression of the human antimicrobial peptide LL-37

(Bergman et al., Cell Microbiol., 7:1009 (2005)) and has been reported to be resistant to cationic antimicrobial peptides such as polymyxin B (Tzeng et al., J. Bacteriol., 187:5387 (2005)). The antimicrobial activity of K9CATH against N. gonorrhoeae is approximately 4-8 times greater than that of the most potent natural cathelicidin reported (including all synthetic analogs) (Ostberg et al., Peptides, 26:197 (2005)). Similar activity was observed against Ureaplasma canigenitalium, which has been implied as one of the causative agents in canine STD.

The antimicrobial activity of K9CATH showed no salt-dependency (FIG. 7), which may be another feature by which this canine cathelicidin ensures a higher degree of potency by enhancing the resiliency of the peptide towards different environmental conditions. K9CATH was also unaffected by LPS treatment at 0.01 μg/mL, whereas an increase in MIC to 60 μM was noted at 0.1 and 10 μg/mL, suggesting that the peptide neutralizes endotoxin by an apparent irreversible binding. A speculative scenario could be that the C-terminal seven amino acid highly polar non-coiled portion of K9CATH (FIG. 6B) may function as a physicochemical anchor to trap and secure endotoxin leading to elimination of potentially injurious microbial components. Consistent with other reports (Bartlett et al., Int. J. Antimicrob. Agnets, 23:606 (2004); Ciomei et al., Antimicrob. Agents Chemother., 49:2845 (2005)), a significant decrease in K9CATH activity against E. coli was detected with increasing serum concentrations (Table 5). This may be a mechanism by which the cells of the host animal are ensured protection against potential cytotoxic effects due to the presence of cathelicidin in the blood.

A unique feature of K9CATH is a remarkably low hemolytic activity across three species (dog, human and chicken). SMAP-29, one of the most potent cathelicidin peptides identified to date (Gennaro et al., Biopolymers, 55:31 (2000); Travis et al., Infect. Immunol., 68:2748 (2000)) causes 67% hemolysis of human RBCs at a concentration of 80 μM (Skerlavaj et al., FEBS Lett., 463:58 (1999)). In contrast, the present studies showed that K9CATH exhibits only minimum hemolysis (<5%) of human erythrocytes at the same concentration. Despite the fact that other cathelicidins (e.g. CRAMP-18) (Shin et al., Biochem. Biophys. Res. Commun., 275:904 (2000) have shown only minimal hemolytic activity, it is unknown whether this feature persists across different species as is the case with the K9CATH peptide (FIG. 9).

In sum, a novel mammalian cathelicidin peptide, K9CATH, from canine myeloid precursor cells was identified. K9CATH displays broad antimicrobial activity not only against Gram-positive bacteria (Listeria monocytogenes, and Staphylococcus aureus), Gram-negative bacteria (Escherichia coli, Klebsiella pneumoniae, Salmonella serotype Typhimurium, Pseudomonas aeruginosa, Proteus mirabilis, Salmonella serotype Enteritidis, and Neisseria gonorrhoeae), and yeast (Candida albicans), but also towards a parasite (i.e., Trichomona vaginalis). The antimicrobial activity of K9CATH was particularly potent against pathogens associated with STD, specifically Neisseria gonorrhoeae, which could provide a useful in vivo model for more profound mechanistic studies relevant to the role of these host defense molecules in the innate defense system. The present data suggest that K9CATH may be a central effector molecule involved in innate defense mechanisms in the canine. Furthermore, the specific characteristics of this antimicrobial peptide may point towards even wider applications given the breadth of the compound's killing capacity and its unique resistance towards different micro-environmental biochemical conditions.

REFERENCES

[1] Zanetti M. Cathelicidins, multifunctional peptides of the innate immunity. J Leukoc Biol 2004; 75:39-48.

[2] Boman H G. Antibacterial peptides: basic facts and emerging concepts. J Intern Med 2003; 254:197-215.

[3] Tomasinsig L, Zanetti M. The cathelicidins—structure, function and evolution. Curr Protein Pept Sci 2005; 6:23-34.

[4] Zaiou M, Gallo R. Cathelicidins, essential gene-encoded mammalian antibiotics. Journal of Molecular Medicine 2002; 80:549-61.

[5] Bals R, Wilson J M. Cathelicidins—a family of multifunctional antimicrobial peptides. Cell Mol Life Sci 2003; 60:711-20.

[6] Zanetti M, Del Sal G, Storici P, et al. The cDNA of the neutrophil antibiotic Bac5 predicts a pro-sequence homologous to a cysteine proteinase inhibitor that is common to other neutrophil antibiotics. J Biol Chem 1993; 268:522-6.

[7] Zaiou M, Nizet V, Gallo R L. Antimicrobial and protease inhibitory functions of the human cathelicidin (hCAP18/LL-37) prosequence. J Invest Dermatol 2003; 120:810-6.

[8] Agerberth B, Charo J, Werr J, et al. The human antimicrobial and chemotactic peptides LL-37 and alpha-defensins are expressed by specific lymphocyte and monocyte populations. Blood 2000; 96:3086-93.

[9] Larrick J W, Hirata M, Zheng H, et al. A novel granulocyte-derived peptide with lipopolysaccharide-neutralizing activity. J Immunol 1994; 152:231-40.

[10] Niyonsaba F, Hirata M, Ogawa H, et al. Epithelial cell-derived antibacterial peptides human beta-defensins and cathelicidin: multifunctional activities on mast cells. Curr Drug Targets Inflamm Allergy 2003; 2:224-31.

[11] Niyonsaba F, Iwabuchi K, Someya A, et al. A cathelicidin family of human antibacterial peptide LL-37 induces mast cell chemotaxis. Immunology 2002; 106:20-6.

[12] Gennaro R, Zanetti M. Structural features and biological activities of the cathelicidin-derived antimicrobial peptides. Biopolymers 2000; 55:31-49.

[13] Zhao C, Nguyen T, Boo L M, et al. RL-37, an alpha-helical antimicrobial peptide of the rhesus monkey. Antimicrob Agents Chemother 2001; 45:2695-702.

[14] Bals R, Lang C, Weiner D J, et al. Rhesus monkey (Macaca mulatta) mucosal antimicrobial peptides are close homologues of human molecules. Clin Diagn Lab Immunol 2001; 8:370-5.

[15] Bals R, Wang X, Zasloff M, et al. The peptide antibiotic LL-37/hCAP-18 is expressed in epithelia of the human lung where it has broad antimicrobial activity at the airway surface. Proc Natl Acad Sci USA 1998; 95:9541-6.

[16] Skerlavaj B, Gennaro R, Bagella L, et al. Biological characterization of two novel cathelicidin-derived peptides and identification of structural requirements for their antimicrobial and cell lytic activities. J Biol Chem 1996; 271: 28375-81.

[17] Scocchi M, Wang S, Zanetti M. Structural organization of the bovine cathelicidin gene family and identification of a novel member. FEBS Lett 1997; 417:311-5.

[18] Shamova O, Brogden K A, Zhao C, et al. Purification and properties of proline-rich antimicrobial peptides from sheep and goat leukocytes. Infect Immun 1999; 67:4106-11.

[19] Bagella L, Scocchi M, Zanetti M. cDNA sequences of three sheep myeloid cathelicidins. FEBS Lett 1995; 376: 225-8.

[20] Zanetti M, Storici P, Tossi A, et al. Molecular cloning and chemical synthesis of a novel antibacterial peptide derived from pig myeloid cells. J Biol Chem 1994; 269:7855-8.

[21] Vunnam S, Juvvadi P, Merrifield R B. Synthesis and antibacterial action of cecropin and proline-arginine-rich peptides from pig intestine. J Pept Res 1997; 49:59-66.

[22] Scocchi M, Bontempo D, Boscolo S, et al. Novel cathelicidins in horse leukocytes (1). FEBS Lett 1999; 457:459-64.

[23] Skerlavaj B, Scocchi M, Gennaro R, et al. Structural and functional analysis of horse cathelicidin peptides. Antimicrob Agents Chemother 2001; 45:715-22.

[24] Pestonjamasp V K, Huttner K H, Gallo R L. Processing site and gene structure for the murine antimicrobial peptide CRAMP. Peptides 2001; 22:1643-50.

[25] Termen S, Tollin M, Olsson B, et al. Phylogeny, processing and expression of the rat cathelicidin rCRAMP: a model for innate antimicrobial peptides. Cell Mol Life Sci 2003; 60:536-49.

[26] Nagaoka I, Hirota S, Niyonsaba F, et al. Cathelicidin family of antibacterial peptides CAP18 and CAP11 inhibit the expression of TNF-alpha by blocking the binding of LPS to CD14(+) cells. J Immunol 2001; 167:3329-38.

[27] Levy O, Weiss J, Zarember K, et al. Antibacterial 15-kDa protein isoforms (p15s) are members of a novel family of leukocyte proteins. J Biol Chem 1993; 268:6058-63.

[28] Zanetti M. The Role of Cathelicidins in the Innate Host Defenses of Mammals. Current Issues in Molecular Biology 2005; 7:179-96.

[29] Wu H, Zhang G, Minton J E, et al. Regulation of cathelicidin gene expression: induction by lipopolysaccharide, interleukin-6, retinoic acid, and *Salmonella enterica* serovar typhimurium infection. Infect Immun 2000; 68:5552-8.

[30] Sang Y, Ortega M T, Blecha F, et al. Molecular Cloning and Characterization of Three {beta}-Defensins from Canine Testes. Infection and Immunity 2005; 73:2611-20.

[31] Altschul S F, Gish W, Miller W, et al. Basic local alignment search tool. J Mol Biol 1990; 215:403-10.

[32] Soulages J L, Arrese E L, Chetty P S, et al. Essential role of the conformational flexibility of helices 1 and 5 on the lipid binding activity of apolipophorin-III. J Biol Chem 2001; 276:34162-6.

[33] Chen Y H, Yang J T, Chau K H. Determination of the helix and beta form of proteins in aqueous solution by circular dichroism. Biochemistry 1974; 13:3350-9.

[34] Chen C, Brock R, Luh F, et al. The solution structure of the active domain of CAP18—a lipopolysaccharide binding protein from rabbit leukocytes. FEBS Lett 1995; 370:46-52.

[35] Thompson J D, Higgins D G, Gibson T J. CLUSTAL W: improving the sensitivity of progressive multiple sequence alignment through sequence weighting, position-specific gap penalties and weight matrix choice. Nucleic Acids Res 1994; 22:4673-80.

[36] Sanchez R, Sali A. Comparative protein structure modeling. Introduction and practical examples with modeller. Methods Mol Biol 2000; 143:97-129.

[37] McGuffin L J, Bryson K, Jones D T. The PSIPRED protein structure prediction server. Bioinformatics 2000; 16:404-5.

[38] Pfaller M A, Chaturvedi V, Espinel-Ingroff A, et al. Manual NCCLS. Reference Method for Broth Dilution Antifungal Susceptibility Testing of Yeasts; Approved Standard-Second Edition. NCCLS document M27-A2 [ISBN 1-56238-469-4]. NCCLS, 940 West Valley Road, Suite 1400, Wayne, Pa. 19087-1898, USA. NCCLS 2002; 22.

[39] Ferraro M J, Wikler M A, Craig W A, et al. Manual NCCLS. Methods for Dilution Antimicrobial Susceptibility Tests for Bacteria That Grow Aerobically; Approved Standard-Sixth Edition. NCCLS document M7-A6 [ISBN 1-56238-486-4]. NCCLS, 940 West Valley Road, Suite 1400, Wayne, Pa. 19087-1898 USA, 2003. NCCLS 2003; 23.

[40] Turner J, Cho Y, Dinh N N, et al. Activities of LL-37, a cathelin-associated antimicrobial peptide of human neutrophils. Antimicrob Agents Chemother 1998; 42:2206-14.

[41] Tack B F, Sawai M V, Kearney W R, et al. SMAP-29 has two LPS-binding sites and a central hinge. Eur J Biochem 2002; 269:1181-9.

[42] Skerlavaj B, Benincasa M, Risso A, et al. SMAP-29: a potent antibacterial and antifungal peptide from sheep leukocytes. FEBS Lett 1999; 463:58-62.

[43] Yu K, Park K, Kang S W, et al. Solution structure of a cathelicidin-derived antimicrobial peptide, CRAMP as determined by NMR spectroscopy. J Pept Res 2002; 60:1-9.

[44] Risso A, Zanetti M, Gennaro R. Cytotoxicity and apoptosis mediated by two peptides of innate immunity. Cell Immunol 1998; 189:107-15.

[45] Scott M G, Davidson D J, Gold M R, et al. The human antimicrobial peptide LL-37 is a multifunctional modulator of innate immune responses. J Immunol 2002; 169: 3883-91.

[46] Castiglioni B, Scocchi M, Zanetti M, et al. Six antimicrobial peptide genes of the cathelicidin family map to bovine chromosome 22q24 by fluorescence in situ hybridization. Cytogenet Cell Genet. 1996; 75:240-2.

[47] Zhang G, Ross C R, Blecha F. Porcine antimicrobial peptides: new prospects for ancient molecules of host defense. Vet Res 2000; 31:277-96.

[48] Murakami M, Lopez-Garcia B, Braff M, et al. Postsecretory processing generates multiple cathelicidins for enhanced topical antimicrobial defense. J Immunol 2004; 172:3070-7.

[49] Shin S Y, Park E J, Yang S T, et al. Structure-activity analysis of SMAP-29, a sheep leukocytes-derived antimicrobial peptide. Biochem Biophys Res Commun 2001; 285:1046-51.

[50] Murakami M, Ohtake T, Dorschner R A, et al. Cathelicidin antimicrobial peptides are expressed in salivary glands and saliva. J Dent Res 2002; 81:845-50.

[51] Ostberg N, Kaznessis Y. Protegrin structure-activity relationships: using homology models of synthetic sequences to determine structural characteristics important for activity. Peptides 2005; 26:197-206.

[52] Zanetti M, Gennaro R, Skerlavaj B, et al. Cathelicidin peptides as candidates for a novel class of antimicrobials. Curr Pharm Des 2002; 8:779-93.

[53] Ramanathan B, Davis E G, Ross C R, et al. Cathelicidins: microbicidal activity, mechanisms of action, and roles in innate immunity. Microbes Infect 2002; 4:361-72.

[54] Oren Z, Shai Y. Mode of action of linear amphipathic alpha-helical antimicrobial peptides. Biopolymers 1998; 47:451-63.

[55] Sorensen O E, Follin P, Johnsen A H, et al. Human cathelicidin, hCAP-18, is processed to the antimicrobial peptide LL-37 by extracellular cleavage with proteinase 3. Blood 2001; 97:3951-9.

[56] Carmichael L E, Joubert J C. Transmission of *Brucella canis* by contact exposure. Cornell Vet 1988; 78:63-73.

[57] Doig P A, Ruhnke H L, Bosu W T. The genital *Mycoplasma* and *Ureaplasma* flora of healthy and diseased dogs. Can J Comp Med 1981; 45:233-8.

[58] Harasawa R, Imada Y, Kotani H, et al. *Ureaplasma canigenitalium* sp. nov., isolated from dogs. Int J Syst Bacteriol 1993; 43:640-4.

[59] Bergman P, Johansson L, Asp V, et al. *Neisseria gonorrhoeae* down-regulates expression of the human antimicrobial peptide LL-37. Cell Microbiol 2005; 7:1009-17.

[60] Tzeng Y L, Ambrose K D, Zughaier S, et al. Cationic antimicrobial peptide resistance in *Neisseria meningitidis*. J Bacteriol 2005; 187:5387-96.

[61] Bartlett K H, McCray P B, Jr., Thorne P S. Reduction in the bactericidal activity of selected cathelicidin peptides by bovine calf serum or exogenous endotoxin. Int J Antimicrob Agents 2004; 23:606-12.

[62] Ciornei C D, Sigurdardottir T, Schmidtchen A, et al. Antimicrobial and chemoattractant activity, lipopolysaccharide neutralization, cytotoxicity, and inhibition by serum of analogs of human cathelicidin LL-37. Antimicrob Agents Chemother 2005; 49:2845-50.

[63] Travis S M, Anderson N N, Forsyth W R, et al. Bactericidal activity of mammalian cathelicidin-derived peptides. Infect Immun 2000; 68:2748-55.

[64] Shin S Y, Kang S W, Lee D G, et al. CRAMP analogues having potent antibiotic activity against bacterial, fungal, and tumor cells without hemolytic activity. Biochem Biophys Res Commun 2000; 275:904-9.

All patents and publications referenced or mentioned herein are hereby incorporated by reference to the same extent as if it had been incorporated by reference in its entirety individually or set forth herein in its entirety.

The specific methods and compositions described herein are representative and are not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention.

What is claimed is:

1. A purified polypeptide consisting of SEQ ID NO: 4, a variant of SEQ ID NO: 4 having at least 80% amino acid sequence identity to SEQ ID NO: 4, or a fragment thereof having at least 15 contiguous amino acids of SEQ ID NO: 4 or the variant thereof.

2. The purified polypeptide of claim 1 wherein the variant has at least 90% amino acid sequence identity to SEQ ID NO: 4.

3. The purified polypeptide of claim 1 wherein the variant has 1 to 4 conservative amino acid substitutions.

4. The purified polypeptide of claim 1 wherein the fragment comprises at least 25 contiguous amino acids of SEQ ID NO: 4.

5. A composition comprising the polypeptide, the variant or the fragment of claim 1.

6. The composition of claim 5 further comprising a pharmaceutically acceptable carrier or a food additive.

7. A method of inhibiting microbial growth comprising contacting the microorganism with an effective amount of the polypeptide, the variant or the fragment of claim 1.

8. The method of claim 7 wherein the growth of a Gram-positive bacterium, a Gram-negative bacterium, a yeast or a protozoan is inhibited.

9. The method of claim 7 wherein the microbe is the causative agent of a food-borne illness or a sexually transmitted disease.

10. The method of claim 9 wherein the disease is syphilis, chlamydia, gonorrhoeae, trichomoniasis, or thrush.

11. The method of claim 7 wherein the microbe is *Listeria monocytogenes, Staphylococcus aureus, Escherichia coli, Klebsiella pneumoniae, Salmonella typhimurium, Pseudomonas aeruginosa, Proteus mirabilis, Salmonella enteritidis, Neisseria gonorrhoeae, Ureaplasma canigenitalium, Ureaplasma urealyticum, Candida albicans,* or *Trichomonas vaginalis*.

12. An article of manufacture comprising the polypeptide, the variant or the fragment of claim 1.

13. The purified polypeptide of claim 1, wherein the variant or fragment has a deletion at the amino or the carboxy terminus.

14. The purified polypeptide of claim 1, having a sequence consisting of any of SEQ ID NOs: 4, 6, 8, 10, 12, 14, 16, 18, 20, 22, 24, 26, 28, 30, 32, or a combination thereof.

* * * * *

SEQUENCE LISTING

```
<160> NUMBER OF SEQ ID NOS: 46

<210> SEQ ID NO 1
<211> LENGTH: 630
<212> TYPE: DNA
<213> ORGANISM: Canis familiaris

<400> SEQUENCE: 1
ggagagactt gcaggctgag aggagggaga cttggggacc atggagaccc agaaggacag      60
cccctccctg gggcggtggt cactgttgct actgctgctg ggcctggtga tcactccggc     120
tgcctcccgg gcccttagct acaggaggc tgtgctccgt gctgtgaatg gcttcaacca     180
gcggtcctcg gaggagaatc tctaccgtct cctgcagctg aactcacagc ccaagggaga     240
tgaggatcca aacatcccaa agcctgtgag cttcacagtg aaggagactg tgtgtcccaa     300
gacgacacag cagcctctgg agcagtgtgg tttcaaggac aatgggctgg tgaaacagtg     360
tgaagggaca gtcatcctgg acgaggacac gggctacttt gacctcaact gtgattcaat     420
cctgcaagtc aagaaaattg accggctgaa agagctcatc acgacagggg ggcagaagat     480
tggcgaaaag attaggagaa ttggccagag aatcaaggat tttttttaaga atcttcagcc     540 cagggaggag aagtcctaag ggcctgcttt gccctggctt aggcttctgg accctgaaaa     600
ataaattttt gtgaaagcaa aaaaaaaaaa                                      630

<210> SEQ ID NO 2
<211> LENGTH: 172
<212> TYPE: PRT
<213> ORGANISM: Canis familiaris

<400> SEQUENCE: 2

Met Glu Thr Gln Lys Asp Ser Pro Ser Leu Gly Arg Trp Ser Leu Leu
1               5                   10                  15

Leu Leu Leu Leu Gly Leu Val Ile Thr Pro Ala Ala Ser Arg Ala Leu
            20                  25                  30

Ser Tyr Arg Glu Ala Val Leu Arg Ala Val Asn Gly Phe Asn Gln Arg
        35                  40                  45

Ser Ser Glu Glu Asn Leu Tyr Arg Leu Leu Gln Leu Asn Ser Gln Pro
    50                  55                  60
```

Lys Gly Asp Glu Asp Pro Asn Ile Pro Lys Pro Val Ser Phe Thr Val
65                  70                  75                  80

Lys Glu Thr Val Cys Pro Lys Thr Thr Gln Gln Pro Leu Glu Gln Cys
                85                  90                  95

Gly Phe Lys Asp Asn Gly Leu Val Lys Gln Cys Glu Gly Thr Val Ile
            100                 105                 110

Leu Asp Glu Asp Thr Gly Tyr Phe Asp Leu Asn Cys Asp Ser Ile Leu
        115                 120                 125

Gln Val Lys Lys Ile Asp Arg Leu Lys Glu Leu Ile Thr Thr Gly Gly
    130                 135                 140

Gln Lys Ile Gly Glu Lys Ile Arg Arg Ile Gly Gln Arg Ile Lys Asp
145                 150                 155                 160

Phe Phe Lys Asn Leu Gln Pro Arg Glu Glu Lys Ser
                165                 170

<210> SEQ ID NO 3
<211> LENGTH: 117
<212> TYPE: DNA
<213> ORGANISM: Canis familiaris

<400> SEQUENCE: 3
cggctgaaag agctcatcac gacagggggg cagaagattg gcgaaaagat taggagaatt     60
ggccagagaa tcaaggattt ttttaagaat cttcagccca gggaggagaa gtcctaa      117

<210> SEQ ID NO 4
<211> LENGTH: 38
<212> TYPE: PRT
<213> ORGANISM: Canis familiaris

<400> SEQUENCE: 4

Arg Leu Lys Glu Leu Ile Thr Thr Gly Gly Gln Lys Ile Gly Glu Lys
1               5                   10                  15

Ile Arg Arg Ile Gly Gln Arg Ile Lys Asp Phe Phe Lys Asn Leu Gln
                20                  25                  30

Pro Arg Glu Glu Lys Ser
        35

<210> SEQ ID NO 5
<211> LENGTH: 114
<212> TYPE: DNA
<213> ORGANISM: Canis familiaris

<400> SEQUENCE: 5
ctgaaagagc tcatcacgac agggggcag aagattggcg aaaagattag gagaattggc      60
cagagaatca aggattttt taagaatctt cagcccaggg aggagaagtc ctaa           114

<210> SEQ ID NO 6
<211> LENGTH: 37
<212> TYPE: PRT
<213> ORGANISM: Canis familiaris

<400> SEQUENCE: 6

Leu Lys Glu Leu Ile Thr Thr Gly Gly Gln Lys Ile Gly Glu Lys Ile
1               5                   10                  15

Arg Arg Ile Gly Gln Arg Ile Lys Asp Phe Phe Lys Asn Leu Gln Pro
                20                  25                  30

Arg Glu Glu Lys Ser
        35

```
<210> SEQ ID NO 7
<211> LENGTH: 111
<212> TYPE: DNA
<213> ORGANISM: Canis familiaris

<400> SEQUENCE: 7
aaagagctca tcacgacagg ggggcagaag attggcgaaa agattaggag aattggccag      60
agaatcaagg attttttaa gaatcttcag cccagggagg agaagtccta a              111

<210> SEQ ID NO 8
<211> LENGTH: 36
<212> TYPE: PRT
<213> ORGANISM: Canis familiaris

<400> SEQUENCE: 8

Lys Glu Leu Ile Thr Thr Gly Gly Gln Lys Ile Gly Glu Lys Ile Arg
1               5                   10                  15

Arg Ile Gly Gln Arg Ile Lys Asp Phe Phe Lys Asn Leu Gln Pro Arg
            20                  25                  30

Glu Glu Lys Ser
        35

<210> SEQ ID NO 9
<211> LENGTH: 108
<212> TYPE: DNA
<213> ORGANISM: Canis familiaris

<400> SEQUENCE: 9
gagctcatca cgacaggggg gcagaagatt ggcgaaaaga ttaggagaat tggccagaga      60
atcaaggatt ttttaagaa tcttcagccc agggaggaga agtcctaa                  108

<210> SEQ ID NO 10
<211> LENGTH: 35
<212> TYPE: PRT
<213> ORGANISM: Canis familiaris

<400> SEQUENCE: 10

Glu Leu Ile Thr Thr Gly Gly Gln Lys Ile Gly Glu Lys Ile Arg Arg
1               5                   10                  15

Ile Gly Gln Arg Ile Lys Asp Phe Phe Lys Asn Leu Gln Pro Arg Glu
            20                  25                  30

Glu Lys Ser
        35

<210> SEQ ID NO 11
<211> LENGTH: 105
<212> TYPE: DNA
<213> ORGANISM: Canis familiaris

<400> SEQUENCE: 11
ctcatcacga caggggggca agagattggc gaaaagatta ggagaattgg ccagagaatc      60
aaggattttt taagaatct tcagcccagg gaggagaagt cctaa                     105

<210> SEQ ID NO 12
<211> LENGTH: 34
<212> TYPE: PRT
<213> ORGANISM: Canis familiaris

<400> SEQUENCE: 12

Leu Ile Thr Thr Gly Gly Gln Lys Ile Gly Glu Lys Ile Arg Arg Ile
1               5                   10                  15
```

Gly Gln Arg Ile Lys Asp Phe Phe Lys Asn Leu Gln Pro Arg Glu Glu
            20                  25                  30

Lys Ser

<210> SEQ ID NO 13
<211> LENGTH: 102
<212> TYPE: DNA
<213> ORGANISM: Canis familiaris

<400> SEQUENCE: 13
atcacgacag gggggcagaa gattggcgaa aagattagga gaattggcca gagaatcaag      60
gattttttta agaatcttca gcccagggag gagaagtcct aa                       102

<210> SEQ ID NO 14
<211> LENGTH: 33
<212> TYPE: PRT
<213> ORGANISM: Canis familiaris

<400> SEQUENCE: 14

Ile Thr Thr Gly Gly Gln Lys Ile Gly Glu Lys Ile Arg Arg Ile Gly
1               5                   10                  15

Gln Arg Ile Lys Asp Phe Phe Lys Asn Leu Gln Pro Arg Glu Glu Lys
            20                  25                  30

Ser

<210> SEQ ID NO 15
<211> LENGTH: 99
<212> TYPE: DNA
<213> ORGANISM: Canis familiaris

<400> SEQUENCE: 15
cggctgaaag agctcatcac gacagggggg cagaagattg gcgaaaagat taggagaatt      60
ggccagagaa tcaaggattt ttttaagaat cttcagccc                            99

<210> SEQ ID NO 16
<211> LENGTH: 33
<212> TYPE: PRT
<213> ORGANISM: Canis familiaris

<400> SEQUENCE: 16

Arg Leu Lys Glu Leu Ile Thr Thr Gly Gly Gln Lys Ile Gly Glu Lys
1               5                   10                  15

Ile Arg Arg Ile Gly Gln Arg Ile Lys Asp Phe Phe Lys Asn Leu Gln
            20                  25                  30

Pro

<210> SEQ ID NO 17
<211> LENGTH: 102
<212> TYPE: DNA
<213> ORGANISM: Canis familiaris

<400> SEQUENCE: 17
cggctgaaag agctcatcac gacagggggg cagaagattg gcgaaaagat taggagaatt      60
ggccagagaa tcaaggattt ttttaagaat cttcagccca gg                       102

<210> SEQ ID NO 18
<211> LENGTH: 34
<212> TYPE: PRT
<213> ORGANISM: Canis familiaris

<400> SEQUENCE: 18

Arg Leu Lys Glu Leu Ile Thr Thr Gly Gly Gln Lys Ile Gly Glu Lys
1               5                   10                  15

Ile Arg Arg Ile Gly Gln Arg Ile Lys Asp Phe Phe Lys Asn Leu Gln
            20                  25                  30

Pro Arg

<210> SEQ ID NO 19
<211> LENGTH: 105
<212> TYPE: DNA
<213> ORGANISM: Canis familiaris

<400> SEQUENCE: 19
cggctgaaag agctcatcac gacaggggg cagaagattg gcgaaaagat taggagaatt     60
ggccagagaa tcaaggattt ttttaagaat cttcagccca gggag                   105

<210> SEQ ID NO 20
<211> LENGTH: 35
<212> TYPE: PRT
<213> ORGANISM: Canis familiaris

<400> SEQUENCE: 20

Arg Leu Lys Glu Leu Ile Thr Thr Gly Gly Gln Lys Ile Gly Glu Lys
1               5                   10                  15

Ile Arg Arg Ile Gly Gln Arg Ile Lys Asp Phe Phe Lys Asn Leu Gln
            20                  25                  30

Pro Arg Glu
        35

<210> SEQ ID NO 21
<211> LENGTH: 108
<212> TYPE: DNA
<213> ORGANISM: Canis familiaris

<400> SEQUENCE: 21
cggctgaaag agctcatcac gacaggggg cagaagattg gcgaaaagat taggagaatt     60
ggccagagaa tcaaggattt ttttaagaat cttcagccca gggaggag                108

<210> SEQ ID NO 22
<211> LENGTH: 36
<212> TYPE: PRT
<213> ORGANISM: Canis familiaris

<400> SEQUENCE: 22

Arg Leu Lys Glu Leu Ile Thr Thr Gly Gly Gln Lys Ile Gly Glu Lys
1               5                   10                  15

Ile Arg Arg Ile Gly Gln Arg Ile Lys Asp Phe Phe Lys Asn Leu Gln
            20                  25                  30

Pro Arg Glu Glu
        35

<210> SEQ ID NO 23
<211> LENGTH: 111
<212> TYPE: DNA
<213> ORGANISM: Canis familiaris

<400> SEQUENCE: 23
cggctgaaag agctcatcac gacaggggg cagaagattg gcgaaaagat taggagaatt     60
ggccagagaa tcaaggattt ttttaagaat cttcagccca gggaggagaa g             111

-continued

<210> SEQ ID NO 24
<211> LENGTH: 37
<212> TYPE: PRT
<213> ORGANISM: Canis familiaris

<400> SEQUENCE: 24

Arg Leu Lys Glu Leu Ile Thr Thr Gly Gly Gln Lys Ile Gly Glu Lys
1               5                   10                  15

Ile Arg Arg Ile Gly Gln Arg Ile Lys Asp Phe Phe Lys Asn Leu Gln
            20                  25                  30

Pro Arg Glu Glu Lys
        35

<210> SEQ ID NO 25
<211> LENGTH: 120
<212> TYPE: DNA
<213> ORGANISM: Canis familiaris

<400> SEQUENCE: 25
gaccggctga aagagctcat cacgacaggg gggcagaaga ttggcgaaaa gattaggaga      60
attggccaga gaatcaagga ttttttaag aatcttcagc ccaggagga gaagtcctaa      120

<210> SEQ ID NO 26
<211> LENGTH: 39
<212> TYPE: PRT
<213> ORGANISM: Canis familiaris

<400> SEQUENCE: 26

Asp Arg Leu Lys Glu Leu Ile Thr Thr Gly Gly Gln Lys Ile Gly Glu
1               5                   10                  15

Lys Ile Arg Arg Ile Gly Gln Arg Ile Lys Asp Phe Phe Lys Asn Leu
            20                  25                  30

Gln Pro Arg Glu Glu Lys Ser
        35

<210> SEQ ID NO 27
<211> LENGTH: 123
<212> TYPE: DNA
<213> ORGANISM: Canis familiaris

<400> SEQUENCE: 27
attgaccggc tgaaagagct catcacgaca ggggggcaga gattggcga aaagattagg      60 agaattggcc agagaatcaa ggattttttt aagaatcttc agcccaggga ggagaagtcc    120
taa                                                                  123

<210> SEQ ID NO 28
<211> LENGTH: 40
<212> TYPE: PRT
<213> ORGANISM: Canis familiaris

<400> SEQUENCE: 28

Ile Asp Arg Leu Lys Glu Leu Ile Thr Thr Gly Gly Gln Lys Ile Gly
1               5                   10                  15

Glu Lys Ile Arg Arg Ile Gly Gln Arg Ile Lys Asp Phe Phe Lys Asn
            20                  25                  30

Leu Gln Pro Arg Glu Glu Lys Ser
        35                  40

<210> SEQ ID NO 29
<211> LENGTH: 126

```
<212> TYPE: DNA
<213> ORGANISM: Canis familiaris

<400> SEQUENCE: 29
aaaattgacc ggctgaaaga gctcatcacg acagggggc agaagattgg cgaaaagatt      60
aggagaattg ccagagaat caaggatttt tttaagaatc ttcagcccag ggaggagaag     120
tcctaa                                                               126

<210> SEQ ID NO 30
<211> LENGTH: 41
<212> TYPE: PRT
<213> ORGANISM: Canis familiaris

<400> SEQUENCE: 30

Lys Ile Asp Arg Leu Lys Glu Leu Ile Thr Thr Gly Gly Gln Lys Ile
1               5                   10                  15

Gly Glu Lys Ile Arg Arg Ile Gly Gln Arg Ile Lys Asp Phe Phe Lys
                20                  25                  30

Asn Leu Gln Pro Arg Glu Glu Lys Ser
            35                  40

<210> SEQ ID NO 31
<211> LENGTH: 129
<212> TYPE: DNA
<213> ORGANISM: Canis familiaris

<400> SEQUENCE: 31
aagaaaattg accggctgaa agagctcatc acgacagggg ggcagaagat tggcgaaaag      60
attaggagaa ttggccagag aatcaaggat tttttaaga atcttcagcc cagggaggag     120
aagtcctaa                                                            129

<210> SEQ ID NO 32
<211> LENGTH: 42
<212> TYPE: PRT
<213> ORGANISM: Canis familiaris

<400> SEQUENCE: 32

Lys Lys Ile Asp Arg Leu Lys Glu Leu Ile Thr Thr Gly Gly Gln Lys
1               5                   10                  15

Ile Gly Glu Lys Ile Arg Arg Ile Gly Gln Arg Ile Lys Asp Phe Phe
                20                  25                  30

Lys Asn Leu Gln Pro Arg Glu Glu Lys Ser
            35                  40

<210> SEQ ID NO 33
<211> LENGTH: 170
<212> TYPE: PRT
<213> ORGANISM: Homo sapiens

<400> SEQUENCE: 33

Met Lys Thr Gln Arg Asp Gly His Ser Leu Gly Arg Trp Ser Leu Val
1               5                   10                  15

Leu Leu Leu Leu Gly Leu Val Met Pro Leu Ala Ile Ile Ala Gln Val
                20                  25                  30

Leu Ser Tyr Lys Glu Ala Val Leu Arg Ala Ile Asp Gly Ile Asn Gln
                35                  40                  45

Arg Ser Ser Asp Ala Asn Leu Tyr Arg Leu Leu Asp Leu Asp Pro Arg
        50                  55                  60

Pro Thr Met Asp Gly Asp Pro Asp Thr Pro Lys Pro Val Ser Phe Thr
```

```
                65                  70                  75                  80
Val Lys Glu Thr Val Cys Pro Arg Thr Thr Gln Gln Ser Pro Glu Asp
                    85                  90                  95

Cys Asp Phe Lys Lys Asp Gly Leu Val Lys Arg Cys Met Gly Thr Val
                100                 105                 110

Thr Leu Asn Gln Ala Arg Gly Ser Phe Asp Ile Ser Cys Asp Lys Asp
            115                 120                 125

Asn Lys Arg Phe Ala Leu Leu Gly Asp Phe Phe Arg Lys Ser Lys Glu
        130                 135                 140

Lys Ile Gly Lys Glu Phe Lys Arg Ile Val Gln Arg Ile Lys Asp Phe
145                 150                 155                 160

Leu Arg Asn Leu Val Pro Arg Thr Glu Ser
                165                 170

<210> SEQ ID NO 34
<211> LENGTH: 157
<212> TYPE: PRT
<213> ORGANISM: Equus caballus

<400> SEQUENCE: 34

Met Glu Thr Gln Arg Asp Ser Cys Ser Leu Gly Arg Trp Ser Leu Leu
1               5                   10                  15

Leu Leu Leu Leu Gly Leu Val Ile Pro Leu Ala Thr Thr Gln Thr Leu
                20                  25                  30

Ser Tyr Lys Glu Ala Val Leu Arg Ala Val Asp Gly Leu Asn Gln Arg
            35                  40                  45

Ser Ser Asp Glu Asn Leu Tyr Arg Leu Leu Glu Leu Asp Pro Leu Pro
    50                  55                  60

Lys Glu Asp Glu Asp Pro Asp Thr Pro Lys Pro Val Ser Phe Thr Val
65                  70                  75                  80

Lys Glu Thr Val Cys Pro Arg Thr Thr Gln Gln Pro Leu Glu Glu Cys
                85                  90                  95

Asp Phe Lys Glu Asn Gly Leu Val Lys Gln Cys Val Gly Thr Val Val
                100                 105                 110

Leu Asp Pro Ala Lys Asp Tyr Phe Asp Ile Ser Cys Asp Lys Pro Gln
            115                 120                 125

Pro Ile Lys Arg Arg His Trp Phe Pro Leu Ser Phe Gln Glu Phe Leu
        130                 135                 140

Glu Gln Leu Arg Arg Phe Arg Asp Gln Leu Pro Phe Pro
145                 150                 155

<210> SEQ ID NO 35
<211> LENGTH: 155
<212> TYPE: PRT
<213> ORGANISM: Bos taurus

<400> SEQUENCE: 35

Met Glu Thr Pro Arg Ala Ser Leu Ser Leu Gly Arg Trp Ser Leu Trp
1               5                   10                  15

Leu Leu Leu Leu Gly Leu Ala Leu Pro Ser Ala Ser Ala Gln Ala Leu
                20                  25                  30

Ser Tyr Arg Glu Ala Val Leu Arg Ala Val Asp Gln Leu Asn Glu Gln
            35                  40                  45

Ser Ser Glu Pro Asn Ile Tyr Arg Leu Leu Glu Leu Asp Gln Pro Pro
    50                  55                  60

Gln Asp Asp Glu Asp Pro Asp Ser Pro Lys Arg Val Ser Phe Arg Val
65                  70                  75                  80
```

```
Lys Glu Thr Val Cys Ser Arg Thr Thr Gln Gln Pro Pro Glu Gln Cys
                85                  90                  95

Asp Phe Lys Glu Asn Gly Leu Leu Lys Arg Cys Glu Gly Thr Val Thr
            100                 105                 110

Leu Asp Gln Val Arg Gly Asn Phe Asp Ile Thr Cys Asn Asn His Gln
        115                 120                 125

Ser Ile Arg Ile Thr Lys Gln Pro Trp Ala Pro Gln Ala Ala Arg
    130                 135                 140

Leu Cys Arg Ile Val Val Ile Arg Val Cys Arg
145                 150                 155

<210> SEQ ID NO 36
<211> LENGTH: 165
<212> TYPE: PRT
<213> ORGANISM: Bos taurus

<400> SEQUENCE: 36

Met Glu Thr Gln Arg Ala Ser Phe Ser Leu Gly Arg Ser Ser Leu Trp
1               5                   10                  15

Leu Leu Leu Leu Gly Leu Val Val Pro Ser Ala Ser Ala Gln Asp Leu
            20                  25                  30

Ser Tyr Arg Glu Ala Val Leu Arg Ala Val Asp Gln Phe Asn Glu Arg
        35                  40                  45

Ser Ser Glu Ala Asn Leu Tyr Arg Leu Leu Glu Leu Asp Pro Pro Pro
    50                  55                  60

Glu Gln Asp Val Glu His Pro Gly Ala Arg Lys Pro Val Ser Phe Thr
65                  70                  75                  80

Val Lys Glu Thr Val Cys Pro Arg Thr Thr Pro Gln Pro Pro Glu Gln
                85                  90                  95

Cys Asp Phe Lys Glu Asn Gly Leu Val Lys Gln Cys Val Gly Thr Val
            100                 105                 110

Thr Arg Tyr Trp Ile Arg Gly Asp Phe Asp Ile Thr Cys Asn Asn Ile
        115                 120                 125

Gln Ser Ala Gly Leu Phe Arg Arg Leu Arg Asp Ser Ile Arg Arg Gly
    130                 135                 140

Gln Gln Lys Ile Leu Glu Lys Ala Arg Arg Ile Gly Glu Arg Ile Lys
145                 150                 155                 160

Asp Ile Phe Arg Gly
                165

<210> SEQ ID NO 37
<211> LENGTH: 167
<212> TYPE: PRT
<213> ORGANISM: Sus scrofa

<400> SEQUENCE: 37

Met Glu Thr Gln Arg Ala Ser Leu Cys Leu Gly Arg Trp Ser Leu Trp
1               5                   10                  15

Leu Leu Leu Leu Ala Leu Val Val Pro Ser Ala Ser Ala Gln Ala Leu
            20                  25                  30

Ser Tyr Arg Glu Ala Val Leu Arg Ala Val Asp Arg Leu Asn Glu Gln
        35                  40                  45

Ser Ser Glu Ala Asn Leu Tyr Arg Leu Leu Glu Leu Asp Gln Pro Pro
    50                  55                  60

Lys Ala Asp Glu Asp Pro Gly Thr Pro Lys Pro Val Ser Phe Thr Val
65                  70                  75                  80
```

```
Lys Glu Thr Val Cys Pro Arg Pro Thr Trp Arg Pro Glu Leu Cys
                85                  90                  95
Asp Phe Lys Glu Asn Gly Arg Val Lys Gln Cys Val Gly Thr Val Thr
            100                 105                 110
Leu Asp Gln Ile Lys Asp Pro Leu Asp Ile Thr Cys Asn Glu Ile Gln
        115                 120                 125
Ser Val Gly Leu Leu Ser Arg Leu Arg Asp Phe Leu Ser Asp Arg Gly
    130                 135                 140
Arg Arg Leu Gly Glu Lys Ile Glu Arg Ile Gly Gln Lys Ile Lys Asp
145                 150                 155                 160
Leu Ser Glu Phe Phe Gln Ser
                165
```

```
<210> SEQ ID NO 38
<211> LENGTH: 172
<212> TYPE: PRT
<213> ORGANISM: Sus scrofa

<400> SEQUENCE: 38

Met Glu Thr Gln Arg Ala Ser Leu Cys Leu Gly Arg Trp Ser Leu Trp
1               5                   10                  15
Leu Leu Leu Leu Gly Leu Val Val Pro Ser Ala Ser Ala Gln Ala Leu
            20                  25                  30
Ser Tyr Arg Glu Ala Val Leu Arg Ala Val Asp Arg Leu Asn Glu Gln
        35                  40                  45
Ser Ser Glu Ala Asn Leu Tyr Arg Leu Leu Glu Leu Asp Gln Pro Pro
    50                  55                  60
Lys Ala Asp Glu Asp Pro Gly Thr Pro Lys Pro Val Ser Phe Thr Val
65                  70                  75                  80
Lys Glu Thr Val Cys Pro Arg Pro Thr Arg Gln Pro Pro Glu Leu Cys
                85                  90                  95
Asp Phe Lys Glu Asn Gly Arg Val Lys Gln Cys Val Gly Thr Val Thr
            100                 105                 110
Leu Asn Pro Ser Ile His Ser Leu Asp Ile Ser Cys Asn Glu Ile Gln
        115                 120                 125
Ser Val Arg Arg Arg Pro Arg Pro Tyr Leu Pro Arg Pro Arg Pro
    130                 135                 140
Pro Pro Phe Phe Pro Pro Arg Leu Pro Pro Arg Ile Pro Pro Gly Phe
145                 150                 155                 160
Pro Pro Arg Phe Pro Arg Phe Pro Gly Lys Arg
                165                 170
```

```
<210> SEQ ID NO 39
<211> LENGTH: 20
<212> TYPE: DNA
<213> ORGANISM: Artificial Sequence
<220> FEATURE:
<223> OTHER INFORMATION: a synthetic primer
<220> FEATURE:
<221> NAME/KEY: misc_difference
<222> LOCATION: 7
<223> OTHER INFORMATION: n = G or T
<220> FEATURE:
<221> NAME/KEY: misc_difference
<222> LOCATION: 12
<223> OTHER INFORMATION: n = C or T

<400> SEQUENCE: 39
tcactgntgc tnctgctgct                                                   20
```

```
<210> SEQ ID NO 40
<211> LENGTH: 22
<212> TYPE: DNA
<213> ORGANISM: Artificial Sequence
<220> FEATURE:
<223> OTHER INFORMATION: a synthetic primer
<220> FEATURE:
<221> NAME/KEY: misc_difference
<222> LOCATION: 10
<223> OTHER INFORMATION: n = C or T
<220> FEATURE:
<221> NAME/KEY: misc_difference
<222> LOCATION: 11
<223> OTHER INFORMATION: n = C or G
<220> FEATURE:
<221> NAME/KEY: misc_difference
<222> LOCATION: 13
<223> OTHER INFORMATION: n = A or G
<220> FEATURE:
<221> NAME/KEY: misc_difference
<222> LOCATION: 17
<223> OTHER INFORMATION: n = C or G

<400> SEQUENCE: 40
tggcctggtn nanggtnact gt                                              22

<210> SEQ ID NO 41
<211> LENGTH: 22
<212> TYPE: DNA
<213> ORGANISM: Canis familiaris

<400> SEQUENCE: 41
ccttagctac agggaggctg tg                                              22

<210> SEQ ID NO 42
<211> LENGTH: 24
<212> TYPE: DNA
<213> ORGANISM: Canis familiaris

<400> SEQUENCE: 42
gactgtccct tcacactgtt tcac                                            24

<210> SEQ ID NO 43
<211> LENGTH: 66
<212> TYPE: PRT
<213> ORGANISM: Canis familiaris

<400> SEQUENCE: 43

Met Glu Thr Gln Lys Asp Ser Pro Ser Leu Gly Arg Trp Ser Leu Leu
1               5                   10                  15

Leu Leu Leu Leu Gly Leu Val Ile Thr Pro Ala Ala Ser Arg Ala Leu
            20                  25                  30

Ser Tyr Arg Glu Ala Val Leu Arg Ala Val Asn Gly Phe Asn Gln Arg
        35                  40                  45

Ser Ser Glu Glu Asn Leu Tyr Arg Leu Leu Gln Leu Asn Ser Gln Pro
    50                  55                  60

Lys Gly
65

<210> SEQ ID NO 44
<211> LENGTH: 36
<212> TYPE: PRT
<213> ORGANISM: Canis familiaris

<400> SEQUENCE: 44

Asp Glu Asp Pro Asn Ile Pro Lys Pro Val Ser Phe Thr Val Lys Glu
1               5                   10                  15
```

```
Thr Val Cys Pro Lys Thr Thr Gln Gln Pro Leu Glu Gln Cys Gly Phe
            20                  25                  30

Lys Asp Asn Gly
        35

<210> SEQ ID NO 45
<211> LENGTH: 24
<212> TYPE: PRT
<213> ORGANISM: Canis familiaris

<400> SEQUENCE: 45

Leu Val Lys Gln Cys Glu Gly Thr Val Ile Leu Asp Glu Asp Thr Gly
1               5                   10                  15

Tyr Phe Asp Leu Asn Cys Asp Ser
            20

<210> SEQ ID NO 46
<211> LENGTH: 46
<212> TYPE: PRT
<213> ORGANISM: Canis familiaris

<400> SEQUENCE: 46

Ile Leu Gln Val Lys Lys Ile Asp Arg Leu Lys Glu Leu Ile Thr Thr
1               5                   10                  15

Gly Gly Gln Lys Ile Gly Glu Lys Ile Arg Arg Ile Gly Gln Arg Ile
            20                  25                  30

Lys Asp Phe Phe Lys Asn Leu Gln Pro Arg Glu Glu Lys Ser
            35                  40                  45
```